(12) United States Patent
Sun et al.

(10) Patent No.: US 8,263,074 B2
(45) Date of Patent: Sep. 11, 2012

(54) FIBROBLAST GROWTH FACTOR RECEPTOR-1 INHIBITORS AND METHODS OF TREATMENT THEREOF

(75) Inventors: Haijun Sun, New York, NY (US); Juqun Shen, Flushing, NY (US); James Robert Tonra, Skillman, NJ (US)

(73) Assignee: ImClone LLC, New York, NY (US)

( * ) Notice: Subject to any disclaimer, the term of this patent is extended or adjusted under 35 U.S.C. 154(b) by 0 days.

(21) Appl. No.: 13/328,147

(22) Filed: Dec. 16, 2011

(65) Prior Publication Data

US 2012/0121609 A1 May 17, 2012

Related U.S. Application Data

(63) Continuation of application No. 10/575,977, filed as application No. PCT/US2004/034970 on Oct. 18, 2004, now abandoned.

(60) Provisional application No. 60/512,255, filed on Oct. 16, 2003.

(51) Int. Cl.
*A61K 39/395* (2006.01)
*C07K 16/28* (2006.01)

(52) U.S. Cl. ............... 424/130.1; 424/143.1; 530/387.1; 530/388.22

(58) Field of Classification Search .......................... None
See application file for complete search history.

(56) References Cited

U.S. PATENT DOCUMENTS 7,288,251 B2 * 10/2007 Bedian et al. .............. 424/153.1

FOREIGN PATENT DOCUMENTS

WO 2005/037235 4/2005

OTHER PUBLICATIONS

Abath and Simpson, "A Simple Method for the Recovery of Purified Recombinant Peptides Cleaved from Glutathione-S-Transferase-Fusion Proteins," Peptide Research, 3(4):167-168 (1990).
Ausubel et al., "Short Protocols in Molecular Biology", Current Protocols in Molecular Biology, 1:2.20.3, Green Publishing Associates, Inc., and John Wiley & Sons, Inc, New York (1989).
Bayes et al., "Gateways to Clinical Trials," Methods and Findings in Experimental and Clinical Pharmacology, 25 (6):483-506 at 491, Prous, Barcelona, Spain (Jul. 2003).
Blanckaert et al., "Partial characterization of endothelial FGF receptor functional domain by monoclonal antibody VBS-1," Hybridoma and Hybridomics, 21(3): 153-159 (Jun. 2002).
Boerner et al., "Production of Antigen-Specific Human Monoclonal Antibodies from in vitro-primed human splenocytes1," J. Immunol, 147(1):86-95 (1991).
Dieckmann and Tzagoloff, "Assembly of the Mitochondrial Membrane System," J. Biol. Chem., 260:1513-1520 (1985).
Fishwild et al., "High-avidity human IgGK monoclonal antibodies from a novel strain of minilocus transgenic mice," Nature Biotechnology, 14:845-51 (1996).
Smith, et al., "Single-step purification of polypeptides expressed in *Escherichia coli* as fusions with glutathione S-transferase," Gene, 67:31-40 (1988).
Hoogenboom and Winter, "By-passing Immunisation Human Antibodies from Synthetic Repertoires of Germline VH Gene Segments Rearranged in Vitro," J. Mol Biol., 227:381 (1991).
Johnson et al., "The human fibroblast growth factor receptor genes: a common structural arrangement underlies the mechanisms for generating receptor forms that differ in their third immunoglobulin domain," Molecular and Cellular Biology, 11(9): 4627-4634 (Sep. 1991).
Kaufmann and Sharp, "Amplification and Expression of Sequences Cotransfected with a Modular Dihydorfolate Reductase Complementary DNA Gene," J. Mol. Biol., 159:601-621 (1982).
Kostrzewa et al., "Genomic structure and complete sequence of the human FGFR4 gene," Mammalian Genome: Official Journal of the International Mammalian Genome Society, 9(2):131-135 (Feb. 1998).
Lonberg and Huszar, "Human Antibodies from Transgenic Mice," Intern Rev. Immunol, 13:65-93 (1995).
Lonberg et al., "Antigen-specific human antibodies from mice comprising four distinct genetic modifications", Nature, 368:856-859 (1994).
Marks et al., "By-passing Immunization Human Antibodies from V-gene Libraries Displayed on Phage," J. Mol. Biol., 222:581 (1991).
Morrison, "Success in specification," Nature, 368:812-813 (1994).
Neuberger, "Generating high-avidity human Mabs in mice," Nature Biotechnology, 14:826 (1996).
Partridge et al., "Overexpression of a secretory form of FGF-1 promotes MMP-1-mediated endothelial cell migration," Journal of Cellular Biochemistry, 78(3):487-499 (Jun. 6, 2000).
Powers et al., "Fibroblast growth factors, their receptors and signaling," Endocrine Related Cancer, 7:165-197 at 165-197 (2000).
Skaper et al., "The FGFR1 inhibitor PD 173074 selectively and potently antagonizes FGF-2 neurotrophic and neurotropic effects," Journal of Neurochemistry, 75(4):1520-1527 (Oct. 2000). Southern and Berg, "Transformation of Mammalian Cells to Antibiotic Resistance with a Bacterial Gene Under Control of the SV40 Early Region Promoter," J. Mol. Appl. Genet., 1:327-341 (1982).
Steger et al., "Localization of fibroblast growth factor 2 (FGF-2) protein and the receptors FGFR 1-4 in normal human seminiferous epithelium." Histochemistry and Cell Biology, 110(1):57-62, Germany (1998).
Sun et al., "Monoclonal antibody antagonists of hypothalamic FGFR1 cause potent but reversible hypophagia and weight loss in rodents and monkeys." American Journal of Physiology, Endocrinology and Metabolism, 292(3):E964-E976 (Mar. 2007).

* cited by examiner

*Primary Examiner* — Elizabeth C Kemmerer
*Assistant Examiner* — Regina M Deberry
(74) *Attorney, Agent, or Firm* — Alejandro Martinez; Cynthia Lan Martin

(57) ABSTRACT

The present invention is directed to an antibody or fragments thereof that are specific for a fibroblast growth factor receptor (FGFR)-1(IIIb), FGFR-1(IIIc), and/or FGFR-4. Also, provided herein, are vectors and host cells comprising the nucleic acids encoding those antibodies. The present invention further provides methods of antagonizing FGFR-1 or FGFR-4 as a treatment for obesity, diabetes, or a condition related thereto, and methods of reducing food intake.

6 Claims, 52 Drawing Sheets

Fig. 1A DNA and Amino Acid Sequence of Variable Region of FR1-H7 Heavy Chain

Heavy chain variable region sequence (cDNA)

ATGGCCGAGGTGCAGCTGGTGCAGTCTGGGGCTGAGGTGAAGAAGCCTGGG
GCCTCAGTGAAGGTTTCCTGCAAGGTTTCTGGATACACCTTCACCGACTACTA
CATGCACTGGGTGCAACAGGCCCCTGGAAAAGGGCTTGAGTGGATGGGACTT
GTTGATCCTGAAGATGGTGAAACAATCTACGCAGAGAAGTTCCAGGGCAGAG
TCACCATAACCGCGGACACGTCTACAGACACAGCCTACATGGAGCTGAGCAG
CCTGAGATCTGAGGACACGGCCGTGTATTACTGTGCGAGAGATGACTACATG
GACGTCTGGGGCAAAGGCACCCTGGTCACCGTCTCAAGCGCCTCCACCAAGG
GCCCA

Heavy chain variable region sequence (amino acid)

MAEVQLVQSGAEVKKPGASVKVSCKVSGYTFTDYYMHWVQQAPGKGLEWMG
LVDPEDGETIYAEKFQGRVTITADTSTDTAYMELSSLRSEDTAVYYCARDDYMD
VWGKGTLVTVSSASTKGP

Fig. 1B DNA and Amino Acid Sequence of Variable Region of FR1-H7 light Chain

Light chain variable region sequence (cDNA)

CTTGAAACGACACTCACGCAGTCTCCAGACACCCTGTCTTTGTCTCCAGGAGA
AGGAGCCACCCTCTCCTGTAGGGCCAGTCAGAGTGTTAGCGGCAGTGCGTTG
GCCTGGTACCAGCAGAAACCTGGCCAGGCTCCCAGACTCCTCATCTATGATG
CATCCAGTAGGGCCACTGGCGTCCCAGACAGGTTCAGTGGCAGTGGGTCTGG
GGCAGACTTCAGTCTCACCATCAGCAGACTGGAGCCTGAAGATTTTGCAGTG
TATTCCTGTCAGCAATATGGTAGCTCACCTCTCACTTTCGGCCCTGGGACCAA
AGTGGATGTCAAACGAACTGTGGCTGCACCATCTGTCTTCATCTTCCCGCCAT
CTGATGAGCAGTTGAAATCTGGAACTGCCTCTGTTGTGTGCCTGCTGAATAAC
TTCTATCCCAGAGAGGCCAAAGTACAGTGGAAGGTGGATT

Light chain variable region sequence (amino acid)

LETTLTQSPDTLSLSPGEGATLSCRASQSVSGSALAWYQQKPGQAPRLLIYDASS
RATGVPDRFSGSGSGADFSLTISRLEPEDFAVYSCQQYGSSPLTFGPGTKVDVKR
TVAAPSVFIFPPSDEQLKSGTASVVCLLNNFYPREAKVQWKVD

Fig. 1C CDRs For FR1-H7 Nucleic Acid Sequences

VH (human heavy chain subclass I)

CDR1    GACTACTACATGCAC
CDR2    CTTGTTGATCCTGAAGATGGTGAAACAATCTACGCAGAGAAGTTCCAGGGC
CDR3    GATGACTACATGGACGTC

VL (human kappa light chain subgroup III)

CDR1    AGGGCCAGTCAGAGTGTTAGCGGCAGTGCGTTGGCC
CDR2    GATGCATCCAGTAGGGCCACT
CDR3    CAGCAATATGGTAGCTCACCTCTCACT

Fig. 1D CDRs For FR1-H7 Amino Acid Sequences

VH (human heavy chain subclass I)

CDR1    DYYMH
CDR2    LVDPEDGETIYAEKFQG
CDR3    DDYMDV

VL (human kappa light chain subgroup III)

CDR1    RASQSVSGSALA
CDR2    DASSRAT
CDR3    QQYGSSPLT

Fig. 2A DNA and Amino Acid Sequence of Variable Region of FR1-A1 Heavy Chain

Heavy chain variable region sequence (cDNA)

ATGGCCCAGGTCCAGCTGGTGCAGTCTGGGGCTGAGGTGAAGAAGCCTGGGT
CCTCGGTGAAGGTCTCCTGCAAGGCTTCTGGATCGACCTTCACCGGCTACTAT
ATGCACTGGGTGCGACAGGCCCCTGGACAAGGGCTTGAGTGGATGGGAAGG
ATCATCCCTATCCTTGGTATAGCAAACTACGCACAGAAGTTCCAGGGCAGAG
TCACGATTACCGCGGACAAATCCACGAGCACAGCCTACATGGAGCTGAGCAG
CCTGAGATCTGAGGACACGGCCGTGTACTACTGTGCGAGAGGAGGAGATCTG
GGCGGTATGGACGTCTGGGGCCAAGGGA

Heavy chain variable region sequence (amino acid)

MAQVQLVQSGAEVKKPGSSVKVSCKASGQTFTGYYMHWVRQAPGQGLEWMG
RIIPILGIANYAQKFQGRVTITADKSTSTAYMELSSLRSEDTAVYYCARGGDLGG
MDVWGQG

Fig. 2B DNA and Amino Acid Sequence of Variable Region of FR1-A light Chain

Light chain variable region sequence (cDNA)

CTTGAAATTGTGCTGACTCAGTCTCCACTCTCCCTGCCCGTCACCCCTGGAGA
GCCGGCCTCCATCTCCTGCAGGTCTAGTCAGAGCCTCCGGCATAGTAATGGA
TACAACTATTTGGATTGGTACCTGCAGAAGCCAGGGCAGTCTCCACAGCTCCT
GATCTATTTGGCTTCTAATCGGGCCTCCGGGGTCCCTGACAGGTTCAGTGGCA
GTGGATCAGGCACAGATTTTACACTGAAAATCAGCAGAGTGGAGGCTGAGGA
TGTTGGGGTTTATTACTGCATGCAAGCTCTACAAATTCCTCCGACTTTCGGCC
CTGGGACCAAAGTGGATATCAAACGAACTGTGGCTGCA

Light chain variable region sequence (amino acid)

LEIVLTQSPLSLPVTPGEPASISCRSSQSLRHSNGYNYLDWYLQKPGQSPQLLIYL
ASNRASGVPDRFSGSGSGTDFTLKISRVEAEDVGVYYCMQALQIPPTFGPGTKVD
IKRTVAA

Fig. 2C CDRs For FR1-A1 Nucleic Acid Sequences

VH (human heavy chain subclass I)

CDR1  GGCTACTATATGCAC
CDR2  AGGATCATCCCTATCCTTGGTATAGCAAACTACGCACAGAAGTTCCAGGGC
CDR3  GGAGGAGATCTGGGCGGTATGGACGTC

VL (human kappa light chain subgroup II)

CDR1  AGGTCTAGTCAGAGCCTCCGGCATAGTAATGGATACAACTATTTGGAT
CDR2  TTGGCTTCTAATCGGGCCTCC
CDR3  ATGCAAGCTCTACAAATTCCTCCGACT

Fig. 2D CDRs For FR1-A1 Amino Acid Sequences

VH (human heavy chain subclass I)

CDR1    GYYMH
CDR2    RIIPILGIANYAQKFQG
CDR3    GGDLGGMDV

VL (human kappa light chain subgroup II)

CDR1    RSSQSLRHSNGYNYLD
CDR2    LASNRAS
CDR3    MQALQIPPT

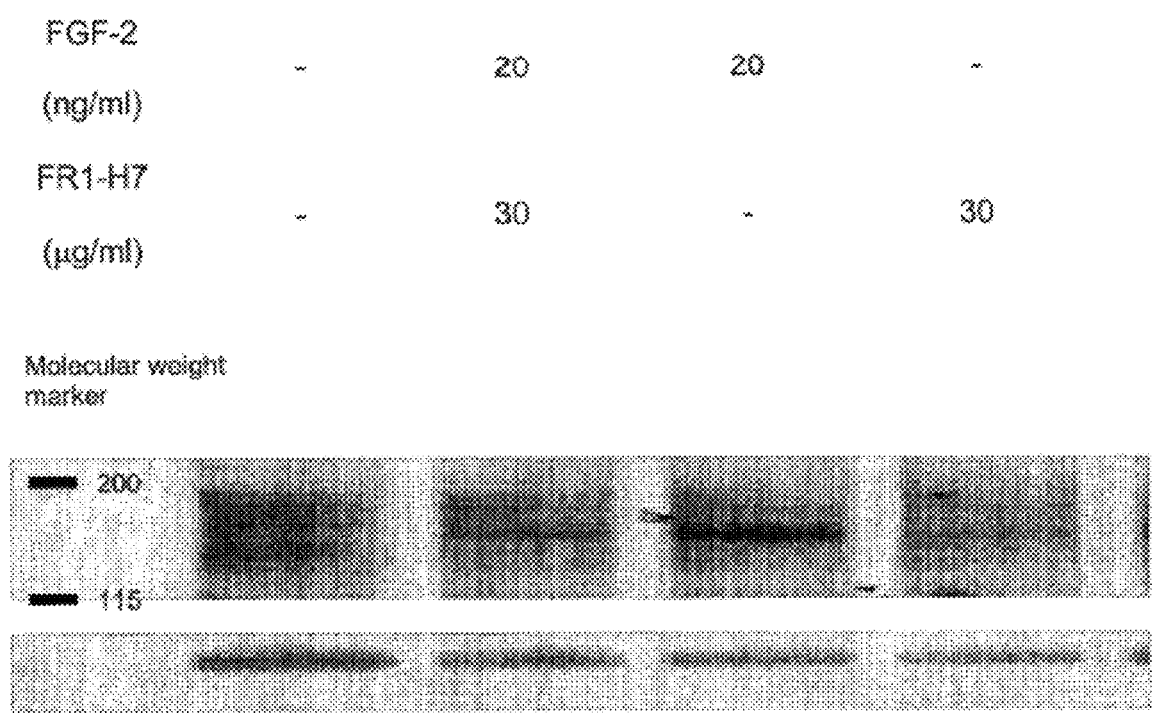

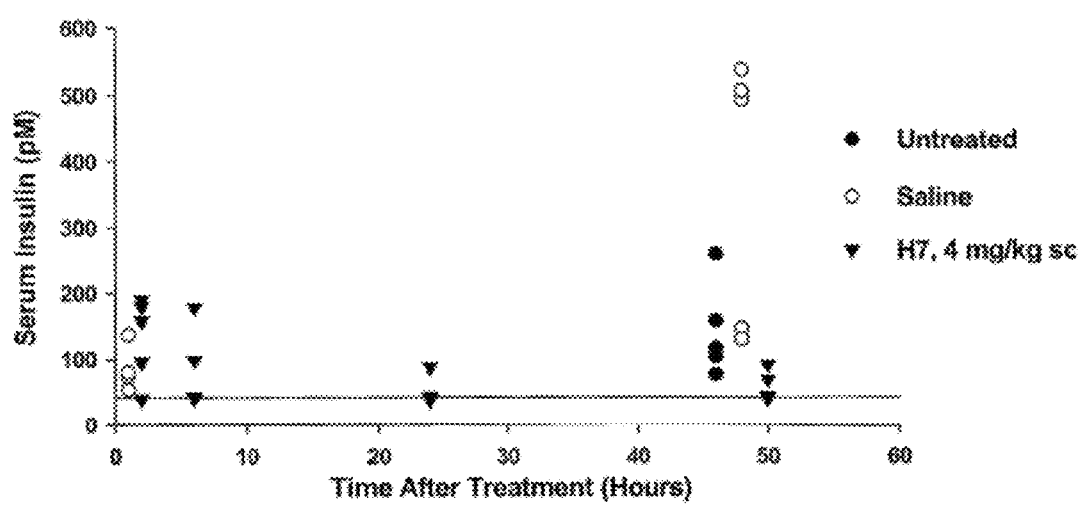

Fig. 27B
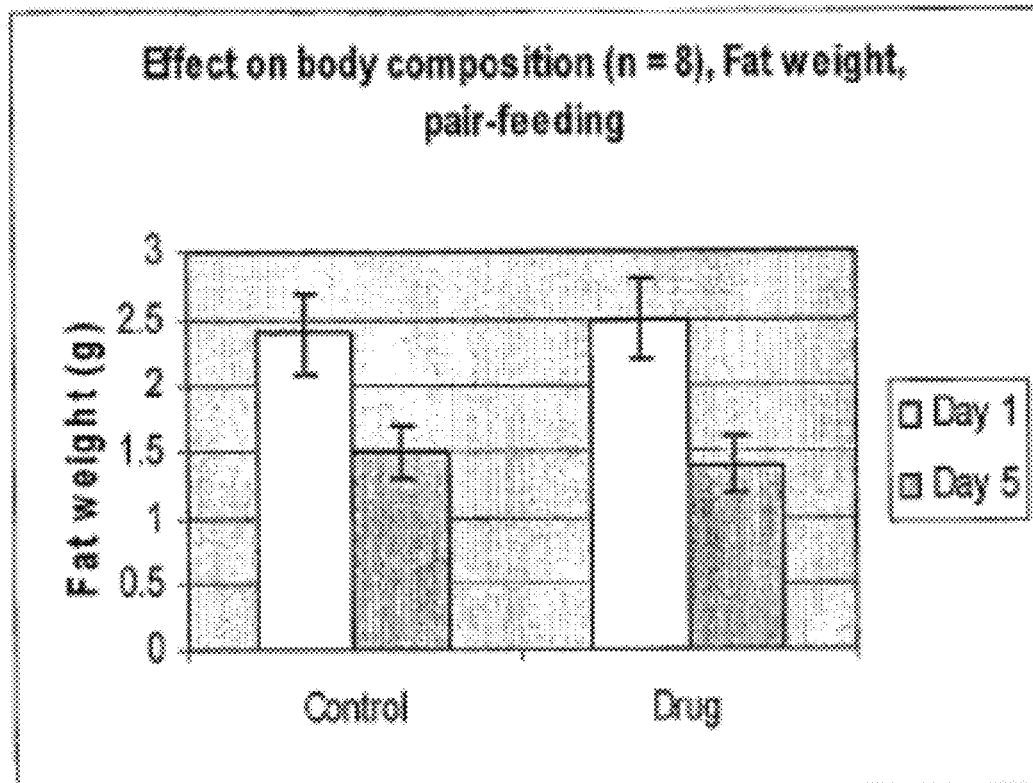
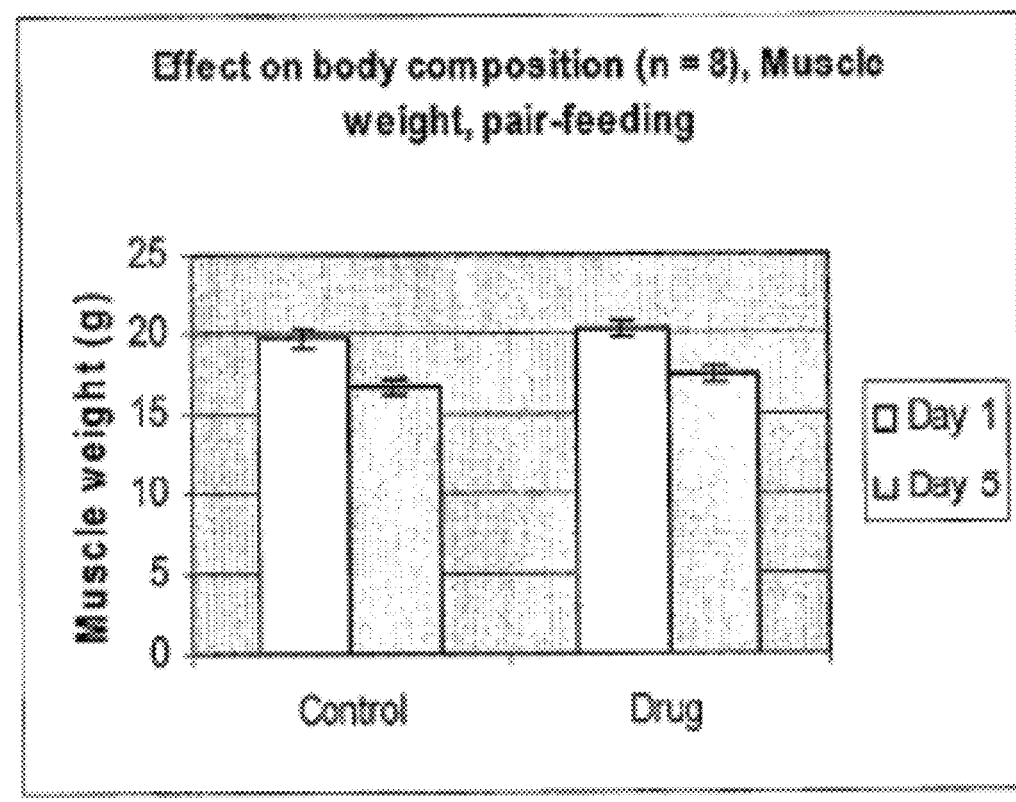

Fig. 28A. FR1-4H antibody variable sequences

Heavy chain variable region sequence (cDNA)
(gamma heavy chain)

```
CAGGTGCAGCTGGTGGAGTTTGGCCCAGGACTGGTGAAGCCTTCGGAGAC      50
CCTGTCCCTCACCTGCACTGTCTCTGGTGGCTCCATCAGTAGTTACTACT     100
GGAGCTGGATCCGGCAGCCCCCAGGGAAGGGACTGGAGTGGATTGGGTAT     150
ATCTATTACAGTGGGAGCACCAACTACAACCCCTCCCTCAAGAGTCGAGT     200
CGCCATATCAGTAGACACGTCCAAGAACCAGTTCTCCCTGAAGCTGAGCT     250
CTGTGACCGCCGCGGACACGGCCGTGTATTACTGTGCGAGAGAGTATTAC     300
TATGATAGTAGTGGTTATTACTTTTATGCTTTTGATATCTGGGGCCAAGG     350
GACCACGGTCACCGTCTCAAGC                                 372
```

Heavy chain variable region sequence (amino acid)

```
QVQLVEPGPGLVKPSETLSLTCTVSGGSISSYYWSWIRQPPGKGLEWIGY      50
IYYSGSTNYNPSLKSRVAISVDTSKNQFSLKLSSVTAADTAVYYCAREYY     100
YDSSGYYFYAFDIWGQGTTVTVSS                               124
```

Light chain variable region sequence (cDNA)

```
CTGCCTGTGCTGACTCAGCCCCCCTCAGCGTCTGGGACCCCCGGGCAGAG      50
GGTCTCCATCTCTTGTTCTGGAAGCAGCTCCAACATCGGAAGTAATTATG     100
TATACTGGTACCAGCAGCTCCCAGGAACGGCCCCCAAACTCCTCATCTTT     150
AGGAATAATCAGCGGCCCTCAGGGGTCCCTGACCGATTCTCTGGCTCCAA     200
GTCTGGCACTTCAGCCTCCCTGGCCATCAGTGGGCTCCGGTCCGAGGATG     250
AGGCTGATTATTACTGTGCAGCATGGGATGACAGCCTGAGTGGTTGGGTG     300
TTCGGCGGAGGGACCAAGCTGACCGTCCTAGGT                      333
```

Light chain variable region sequence (amino acid).
(Lambda light chain)

```
LPVLTQPPSASGTPGQRVSISCSGSSSNIGSNYVYWYQQLPGTAPKLLIF      50
RNNQRPSGVPDRFSGSKSGTSASLAISGLRSEDEADYYCAAWDDSLSGWV     100
FGGGTKLTVLG                                            111
```

Fig. 28B. FR1-4H antibody variable sequence CDRs

CDR amino acid sequences $V_H$:

| | |
|---|---|
| CDR1 | SYYWS |
| CDR2 | YIYYSGSTNYNPSLKS |
| CDR3 | EYYYDSSGYYFYAFDI |

$V_L$:

| | |
|---|---|
| CDR1 | SGSSSNIGSNYVY |
| CDR2 | RNNQRPS |
| CDR3 | AAWDDSLSGWV |

CDR nucleic acid sequences $V_H$:

| | |
|---|---|
| CDR1 | AGTTACTACTGGAGC |
| CDR2 | TATATCTATTACAGTGGGAGCACCAACTACAACCCCTCCCTCAAGAGT |
| CDR3 | GAGTATTACTATGATAGTAGTGGTTATTACTTTTATGCTTTTGATATC |

$V_L$:

| | |
|---|---|
| CDR1 | TCTGGAAGCAGCTCCAACATCGGAAGTAATTATGTATAC |
| CDR2 | AGGAATAATCAGCGGCCCTCA |
| CDR3 | GCAGCATGGGATGACAGCCTGAGTGGTTGGGTG |

Fig. 30. Examples of FGFR small molecule inhibitors.
Indolinone derivatives:
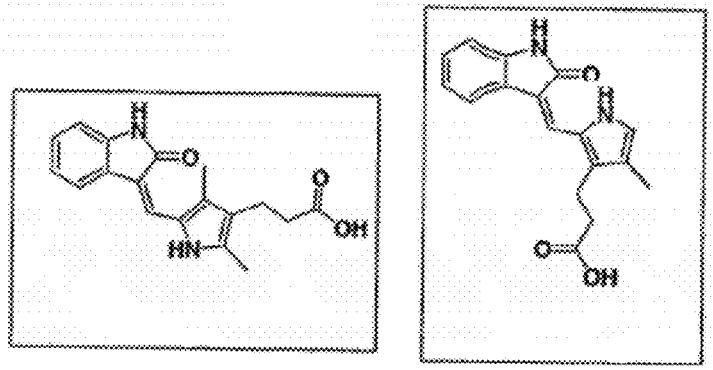
Quinolinone derivatives:
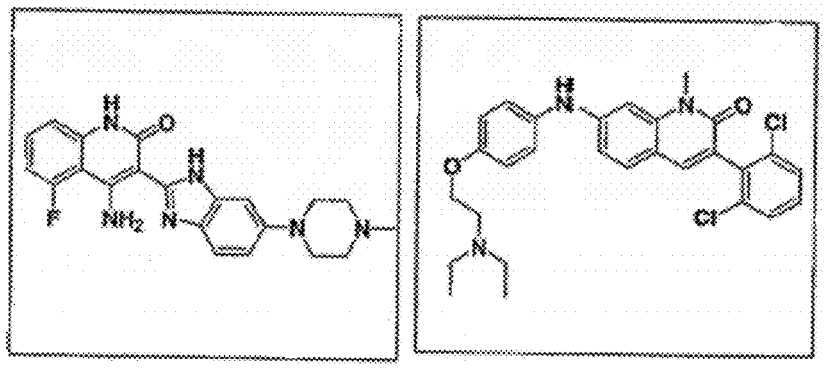
Pyrimido-pyridine derivatives:
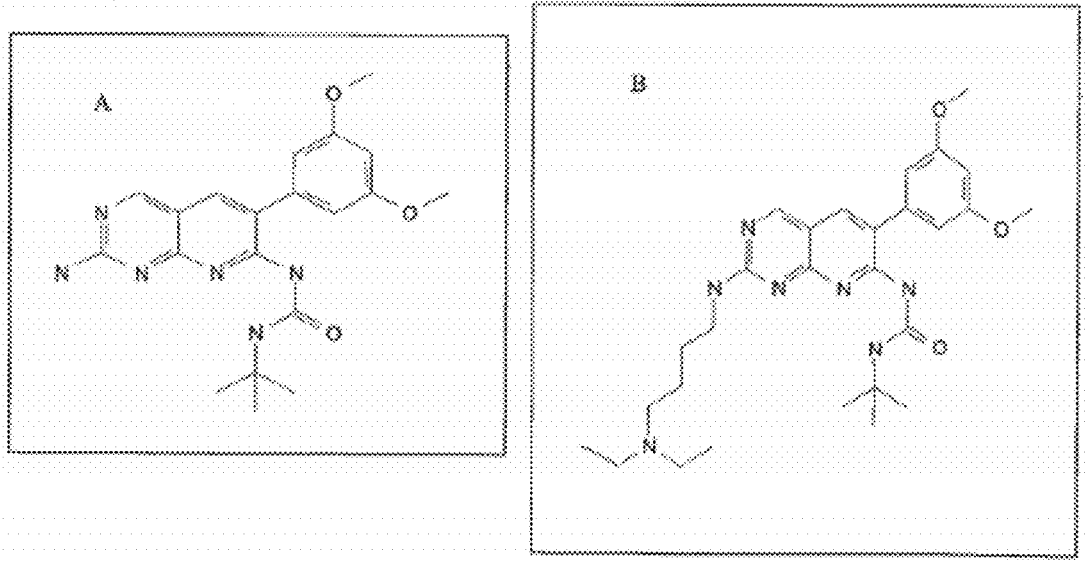

Fig. 31.
| FGF | - | 5 ng | 5 ng | 5 ng | 5 ng | 5 ng | 5 ng |
|---|---|---|---|---|---|---|---|
| Pryimido-pyridines derivative A | - | - | 0.5 µM | 0.2 µM | 0.1 µM | 0.05 µM | 0.02 µM |
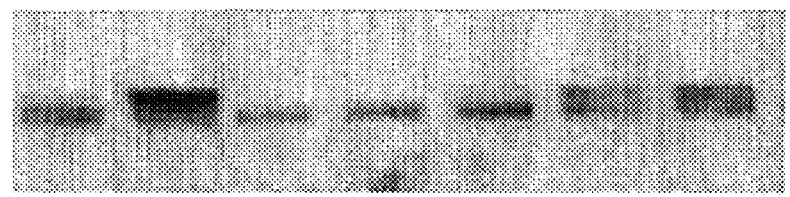
| FGF | - | 100 ng | 100 ng | 100 ng | 100 ng |
|---|---|---|---|---|---|
| Pryimido-pyridines derivative B | - | - | 0.1 µM | 0.03 µM | 0.01 µM |
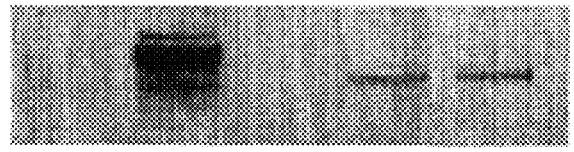

SEQUENCE LISTING

```
<160> NUMBER OF SEQ ID NOS: 48

<210> SEQ ID NO 1
<211> LENGTH: 5
<212> TYPE: PRT
<213> ORGANISM: Homo sapiens

<400> SEQUENCE: 1

Asp Tyr Tyr Met His
1               5

<210> SEQ ID NO 2
<211> LENGTH: 17
<212> TYPE: PRT
<213> ORGANISM: Homo sapiens

<400> SEQUENCE: 2

Leu Val Asp Pro Glu Asp Gly Glu Thr Ile Tyr Ala Glu Lys Phe Gln
1               5                   10                  15

Gly

<210> SEQ ID NO 3
<211> LENGTH: 6
<212> TYPE: PRT
<213> ORGANISM: Homo sapiens

<400> SEQUENCE: 3

Asp Asp Tyr Met Asp Val
1               5

<210> SEQ ID NO 4
<211> LENGTH: 12
<212> TYPE: PRT
<213> ORGANISM: Homo sapiens

<400> SEQUENCE: 4

Arg Ala Ser Gln Ser Val Ser Gly Ser Ala Leu Ala
1               5                   10

<210> SEQ ID NO 5
<211> LENGTH: 7
<212> TYPE: PRT
<213> ORGANISM: Homo sapiens

<400> SEQUENCE: 5

Asp Ala Ser Ser Arg Ala Thr
1               5
```

```
<210> SEQ ID NO 6
<211> LENGTH: 9
<212> TYPE: PRT
<213> ORGANISM: Homo sapiens

<400> SEQUENCE: 6

Gln Gln Tyr Gly Ser Ser Pro Leu Thr
1               5

<210> SEQ ID NO 7
<211> LENGTH: 123
<212> TYPE: PRT
<213> ORGANISM: Homo sapiens

<400> SEQUENCE: 7

Met Ala Glu Val Gln Leu Val Gln Ser Gly Ala Glu Val Lys Lys Pro
1               5                   10                  15

Gly Ala Ser Val Lys Val Ser Cys Lys Val Ser Gly Tyr Thr Phe Thr
            20                  25                  30

Asp Tyr Tyr Met His Trp Val Gln Gln Ala Pro Gly Lys Gly Leu Glu
        35                  40                  45

Trp Met Gly Leu Val Asp Pro Glu Asp Gly Glu Thr Ile Tyr Ala Glu
    50                  55                  60

Lys Phe Gln Gly Arg Val Thr Ile Thr Ala Asp Thr Ser Thr Asp Thr
65                  70                  75                  80

Ala Tyr Met Glu Leu Ser Ser Leu Arg Ser Glu Asp Thr Ala Val Tyr
                85                  90                  95

Tyr Cys Ala Arg Asp Asp Tyr Met Asp Val Trp Gly Lys Gly Thr Leu
            100                 105                 110

Val Thr Val Ser Ser Ala Ser Thr Lys Gly Pro
        115                 120

<210> SEQ ID NO 8
<211> LENGTH: 153
<212> TYPE: PRT
<213> ORGANISM: Homo sapiens

<400> SEQUENCE: 8

Leu Glu Thr Thr Leu Thr Gln Ser Pro Asp Thr Leu Ser Leu Ser Pro
1               5                   10                  15

Gly Glu Gly Ala Thr Leu Ser Cys Arg Ala Ser Gln Ser Val Ser Gly
            20                  25                  30

Ser Ala Leu Ala Trp Tyr Gln Gln Lys Pro Gly Gln Ala Pro Arg Leu
        35                  40                  45

Leu Ile Tyr Asp Ala Ser Ser Arg Ala Thr Gly Val Pro Asp Arg Phe
    50                  55                  60

Ser Gly Ser Gly Ser Gly Ala Asp Phe Ser Leu Thr Ile Ser Arg Leu
65                  70                  75                  80

Glu Pro Glu Asp Phe Ala Val Tyr Ser Cys Gln Gln Tyr Gly Ser Ser
                85                  90                  95

Pro Leu Thr Phe Gly Pro Gly Thr Lys Val Asp Val Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp
145                 150
```

```
<210> SEQ ID NO 9
<211> LENGTH: 5
<212> TYPE: PRT
<213> ORGANISM: Homo sapiens

<400> SEQUENCE: 9

Gly Tyr Tyr Met His
1               5

<210> SEQ ID NO 10
<211> LENGTH: 17
<212> TYPE: PRT
<213> ORGANISM: Homo sapiens

<400> SEQUENCE: 10

Arg Ile Ile Pro Ile Leu Gly Ile Ala Asn Tyr Ala Gln Lys Phe Gln
1               5                   10                  15

Gly

<210> SEQ ID NO 11
<211> LENGTH: 9
<212> TYPE: PRT
<213> ORGANISM: Homo sapiens

<400> SEQUENCE: 11

Gly Gly Asp Leu Gly Gly Met Asp Val
1               5

<210> SEQ ID NO 12
<211> LENGTH: 16
<212> TYPE: PRT
<213> ORGANISM: Homo sapiens

<400> SEQUENCE: 12

Arg Ser Ser Gln Ser Leu Arg His Ser Asn Gly Tyr Asn Tyr Leu Asp
1               5                   10                  15

<210> SEQ ID NO 13
<211> LENGTH: 7
<212> TYPE: PRT
<213> ORGANISM: Homo sapiens

<400> SEQUENCE: 13

Leu Ala Ser Asn Arg Ala Ser
1               5

<210> SEQ ID NO 14
<211> LENGTH: 9
<212> TYPE: PRT
<213> ORGANISM: Homo sapiens

<400> SEQUENCE: 14

Met Gln Ala Leu Gln Ile Pro Pro Thr
1               5

<210> SEQ ID NO 15
<211> LENGTH: 113
<212> TYPE: PRT
<213> ORGANISM: Homo sapiens

<400> SEQUENCE: 15

Met Ala Gln Val Gln Leu Val Gln Ser Gly Ala Glu Val Lys Lys Pro
1               5                   10                  15
```

```
Gly Ser Ser Val Lys Val Ser Cys Lys Ala Ser Gly Gln Thr Phe Thr
            20                  25                  30

Gly Tyr Tyr Met His Trp Val Arg Gln Ala Pro Gly Gln Gly Leu Glu
            35                  40                  45

Trp Met Gly Arg Ile Ile Pro Ile Leu Gly Ile Ala Asn Tyr Ala Gln
 50                  55                  60

Lys Phe Gln Gly Arg Val Thr Ile Thr Ala Asp Lys Ser Thr Ser Thr
 65                  70                  75                  80

Ala Tyr Met Glu Leu Ser Ser Leu Arg Ser Glu Asp Thr Ala Val Tyr
                85                  90                  95

Tyr Cys Ala Arg Gly Gly Asp Leu Gly Gly Met Asp Val Trp Gly Gln
            100                 105                 110

Gly

<210> SEQ ID NO 16
<211> LENGTH: 118
<212> TYPE: PRT
<213> ORGANISM: Homo sapiens

<400> SEQUENCE: 16

Leu Glu Ile Val Leu Thr Gln Ser Pro Leu Ser Leu Pro Val Thr Pro
 1               5                  10                  15

Gly Glu Pro Ala Ser Ile Ser Cys Arg Ser Ser Gln Ser Leu Arg His
            20                  25                  30

Ser Asn Gly Tyr Asn Tyr Leu Asp Trp Tyr Leu Gln Lys Pro Gly Gln
            35                  40                  45

Ser Pro Gln Leu Leu Ile Tyr Leu Ala Ser Asn Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                85                  90                  95

Ala Leu Gln Ile Pro Pro Thr Phe Gly Pro Gly Thr Lys Val Asp Ile
            100                 105                 110

Lys Arg Thr Val Ala Ala
            115

<210> SEQ ID NO 17
<211> LENGTH: 5
<212> TYPE: PRT
<213> ORGANISM: Homo sapiens

<400> SEQUENCE: 17

Ser Tyr Tyr Trp Ser
 1               5

<210> SEQ ID NO 18
<211> LENGTH: 16
<212> TYPE: PRT
<213> ORGANISM: Homo sapiens

<400> SEQUENCE: 18

Tyr Ile Tyr Tyr Ser Gly Ser Thr Asn Tyr Asn Pro Ser Leu Lys Ser
 1               5                  10                  15

<210> SEQ ID NO 19
<211> LENGTH: 16
<212> TYPE: PRT
<213> ORGANISM: Homo sapiens
```

<400> SEQUENCE: 19

Glu Tyr Tyr Tyr Asp Ser Ser Gly Tyr Tyr Phe Tyr Ala Phe Asp Ile
1               5                   10                  15

<210> SEQ ID NO 20
<211> LENGTH: 13
<212> TYPE: PRT
<213> ORGANISM: Homo sapiens

<400> SEQUENCE: 20

Ser Gly Ser Ser Ser Asn Ile Gly Ser Asn Tyr Val Tyr
1               5                   10

<210> SEQ ID NO 21
<211> LENGTH: 7
<212> TYPE: PRT
<213> ORGANISM: Homo sapiens

<400> SEQUENCE: 21

Arg Asn Asn Gln Arg Pro Ser
1               5

<210> SEQ ID NO 22
<211> LENGTH: 11
<212> TYPE: PRT
<213> ORGANISM: Homo sapiens

<400> SEQUENCE: 22

Ala Ala Trp Asp Asp Ser Leu Ser Gly Trp Val
1               5                   10

<210> SEQ ID NO 23
<211> LENGTH: 124
<212> TYPE: PRT
<213> ORGANISM: Homo sapiens

<400> SEQUENCE: 23

Gln Val Gln Leu Val Glu Phe Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
        50                  55                  60

Ser Arg Val Ala Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Tyr Tyr Tyr Asp Ser Ser Gly Tyr Tyr Phe Tyr Ala Phe Asp
                100                 105                 110

Ile Trp Gly Gln Gly Thr Thr Val Thr Val Ser Ser
            115                 120

<210> SEQ ID NO 24
<211> LENGTH: 111
<212> TYPE: PRT
<213> ORGANISM: Homo sapiens

<400> SEQUENCE: 24

Leu Pro Val Leu Thr Gln Pro Ser Ala Ser Gly Thr Pro Gly Gln
1               5                   10                  15

```
Arg Val Ser Ile Ser Cys Ser Gly Ser Ser Asn Ile Gly Ser Asn
             20                  25                  30

Tyr Val Tyr Trp Tyr Gln Gln Leu Pro Gly Thr Ala Pro Lys Leu Leu
         35                  40                  45

Ile Phe Arg Asn Asn Gln Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Trp Val Phe Gly Gly Gly Thr Lys Leu Thr Val Leu Gly
             100                 105                 110
```

<210> SEQ ID NO 25
<211> LENGTH: 15
<212> TYPE: DNA
<213> ORGANISM: Homo sapiens

<400> SEQUENCE: 25
gactactaca tgcac                                                  15

<210> SEQ ID NO 26
<211> LENGTH: 51
<212> TYPE: DNA
<213> ORGANISM: Homo sapiens

<400> SEQUENCE: 26
cttgttgatc ctgaagatgg tgaaacaatc tacgcagaga agttccaggg c           51

<210> SEQ ID NO 27
<211> LENGTH: 18
<212> TYPE: DNA
<213> ORGANISM: Homo sapiens

<400> SEQUENCE: 27
gatgactaca tggacgtc                                               18

<210> SEQ ID NO 28
<211> LENGTH: 36
<212> TYPE: DNA
<213> ORGANISM: Homo sapiens

<400> SEQUENCE: 28
agggccagtc agagtgttag cggcagtgcg ttggcc                           36

<210> SEQ ID NO 29
<211> LENGTH: 21
<212> TYPE: DNA
<213> ORGANISM: Homo sapiens

<400> SEQUENCE: 29
gatgcatcca gtagggccac t                                           21

<210> SEQ ID NO 30
<211> LENGTH: 27
<212> TYPE: DNA
<213> ORGANISM: Homo sapiens

<400> SEQUENCE: 30
cagcaatatg gtagctcacc tctcact                                     27

<210> SEQ ID NO 31
<211> LENGTH: 369
<212> TYPE: DNA
<213> ORGANISM: Homo sapiens

<400> SEQUENCE: 31

```
atggccgagg tgcagctggt gcagtctggg gctgaggtga agaagcctgg ggcctcagtg      60 aaggttttcct gcaaggtttc tggatacacc ttcaccgact actacatgca ctgggtgcaa    120
caggcccctg gaaaagggct tgagtggatg ggacttgttg atcctgaaga tggtgaaaca    180
atctacgcag agaagttcca gggcagagtc accataaccg cggacacgtc tacagacaca    240
gcctacatgg agctgagcag cctgagatct gaggacacgg ccgtgtatta ctgtgcgaga    300
gatgactaca tggacgtctg gggcaaaggc accctggtca ccgtctcaag cgcctccacc    360
aagggccca                                                            369
```

<210> SEQ ID NO 32
<211> LENGTH: 460
<212> TYPE: DNA
<213> ORGANISM: Homo sapiens

<400> SEQUENCE: 32

```
cttgaaacga cactcacgca gtctccagac accctgtctt tgtctccagg agaaggagcc      60
accctctcct gtagggccag tcagagtgtt agcggcagtg cgttggcctg gtaccagcag    120
aaacctggcc aggctcccag actcctcatc tatgatgcat ccagtagggc cactggcgtc    180
ccagacaggt tcagtggcag tgggtctggg gcagacttca gtctcaccat cagcagactg    240
gagcctgaag attttgcagt gtattcctgt cagcaatatg gtagctcacc tctcactttc    300
ggccctggga ccaaagtgga tgtcaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggatt                          460
```

<210> SEQ ID NO 33
<211> LENGTH: 15
<212> TYPE: DNA
<213> ORGANISM: Homo sapiens

<400> SEQUENCE: 33

```
ggctactata tgcac                                                      15
```

<210> SEQ ID NO 34
<211> LENGTH: 51
<212> TYPE: DNA
<213> ORGANISM: Homo sapiens

<400> SEQUENCE: 34

```
aggatcatcc ctatccttgg tatagcaaac tacgcacaga agttccaggg c               51
```

<210> SEQ ID NO 35
<211> LENGTH: 27
<212> TYPE: DNA
<213> ORGANISM: Homo sapiens

<400> SEQUENCE: 35

```
ggaggagatc tgggcggtat ggacgtc                                         27
```

<210> SEQ ID NO 36
<211> LENGTH: 30
<212> TYPE: DNA
<213> ORGANISM: Homo sapiens

```
<400> SEQUENCE: 36
aggtctagtc agagcctccg gcatagtaat                                          30

<210> SEQ ID NO 37
<211> LENGTH: 21
<212> TYPE: DNA
<213> ORGANISM: Homo sapiens

<400> SEQUENCE: 37
ttggcttcta atcgggcctc c                                                   21

<210> SEQ ID NO 38
<211> LENGTH: 27
<212> TYPE: DNA
<213> ORGANISM: Homo sapiens

<400> SEQUENCE: 38
atgcaagctc tacaaattcc tccgact                                             27

<210> SEQ ID NO 39
<211> LENGTH: 340
<212> TYPE: DNA
<213> ORGANISM: Homo sapiens

<400> SEQUENCE: 39
atggcccagg tccagctggt gcagtctggg gctgaggtga agaagcctgg gtcctcggtg         60
aaggtctcct gcaaggcttc tggatcgacc ttcaccggct actatatgca ctgggtgcga       120
caggcccctg gacaagggct tgagtggatg ggaaggatca tccctatcct tggtatagca       180
aactacgcac agaagttcca gggcagagtc acgattaccg cggacaaatc cacgagcaca       240
gcctacatgg agctgagcag cctgagatct gaggacacgg ccgtgtacta ctgtgcgaga       300
ggaggagatc tgggcggtat ggacgtctgg ggccaaggga                             340

<210> SEQ ID NO 40
<211> LENGTH: 354
<212> TYPE: DNA
<213> ORGANISM: Homo sapiens

<400> SEQUENCE: 40
cttgaaattg tgctgactca gtctccactc tccctgcccg tcacccctgg agagccggcc        60
tccatctcct gcaggtctag tcagagcctc cggcatagta atggatacaa ctatttggat      120
tggtacctgc agaagccagg gcagtctcca cagctcctga tctatttggc ttctaatcgg      180
gcctccgggg tccctgacag gttcagtggc agtggatcag gcacagattt tacactgaaa      240
atcagcagag tggaggctga ggatgttggg gtttattact gcatgcaagc tctacaaatt      300
cctccgactt tcggccctgg gaccaaagtg gatatcaaac gaactgtggc tgca            354

<210> SEQ ID NO 41
<211> LENGTH: 15
<212> TYPE: DNA
<213> ORGANISM: Homo sapiens

<400> SEQUENCE: 41
agttactact ggagc                                                         15

<210> SEQ ID NO 42
<211> LENGTH: 48
<212> TYPE: DNA
<213> ORGANISM: Homo sapiens
```

```
<400> SEQUENCE: 42
tatatctatt acagtgggag caccaactac aaccctccc tcaagagt                          48

<210> SEQ ID NO 43
<211> LENGTH: 48
<212> TYPE: DNA
<213> ORGANISM: Homo sapiens

<400> SEQUENCE: 43
gagtattact atgatagtag tggttattac ttttatgctt ttgatatc                         48

<210> SEQ ID NO 44
<211> LENGTH: 39
<212> TYPE: DNA
<213> ORGANISM: Homo sapiens

<400> SEQUENCE: 44
tctggaagca gctccaacat cggaagtaat tatgtatac                                   39

<210> SEQ ID NO 45
<211> LENGTH: 21
<212> TYPE: DNA
<213> ORGANISM: Homo sapiens

<400> SEQUENCE: 45
aggaataatc agcggccctc a                                                      21

<210> SEQ ID NO 46
<211> LENGTH: 33
<212> TYPE: DNA
<213> ORGANISM: Homo sapiens

<400> SEQUENCE: 46
gcagcatggg atgacagcct gagtggttgg gtg                                         33

<210> SEQ ID NO 47
<211> LENGTH: 372
<212> TYPE: DNA
<213> ORGANISM: Homo sapiens

<400> SEQUENCE: 47
caggtgcagc tggtggagtt tgcccaggga ctggtgaagc cttcggagac cctgtccctc            60
acctgcactg tctctggtgg ctccatcagt agttactact ggagctggat ccggcagccc           120
ccagggaagg gactggagtg gattgggtat atctattaca gtgggagcac caactacaac           180
ccctccctca gagtcgagt cgccatatca gtagacacgt ccaagaacca gttctccctg            240
aagctgagct ctgtgaccgc cgcggacacg gccgtgtatt actgtgcgag agagtattac           300
tatgatagta gtggttatta ctttttatgct tttgatatct ggggccaagg gaccacggtc          360
accgtctcaa gc                                                              372

<210> SEQ ID NO 48
<211> LENGTH: 333
<212> TYPE: DNA
<213> ORGANISM: Homo sapiens

<400> SEQUENCE: 48
ctgcctgtgc tgactcagcc cccctcagcg tctgggaccc ccgggcagag ggtctccatc            60
tcttgttctg gaagcagctc caacatcgga agtaattatg tatactggta ccagcagctc           120
ccaggaacgg cccccaaact cctcatcttt aggaataatc agcggccctc agggtccct            180
```

-continued

```
gaccgattct ctggctccaa gtctggcact tcagcctccc tggccatcag tgggctccgg      240
tccgaggatg aggctgatta ttactgtgca gcatgggatg acagcctgag tggttgggtg      300
ttcggcggag ggaccaagct gaccgtccta ggt                                   333
```

FIBROBLAST GROWTH FACTOR RECEPTOR-1 INHIBITORS AND METHODS OF TREATMENT THEREOF

This application is a continuation of U.S. patent application Ser. No. 10/575,977 filed on May 2, 2007, which claims the priority of PCT application PCT/US2004/034970 filed on Oct. 18, 2004, which claims the priority of U.S. provisional application No. 60/512,255 filed Oct. 16, 2003.

FIELD OF THE INVENTION

The present invention relates to an antibody, or fragment thereof, that is specific for fibroblast growth factor receptor (FGFR)-1(IIIb), FGFR-1(IIIc), and/or FGFR-4(IIIc). The present invention further provides methods of antagonizing and neutralizing FGFR-1 and/or FGFR-4 as a treatment for obesity, diabetes, and/or a condition related thereto, including reducing food intake or total body mass.

BACKGROUND OF THE INVENTION

Fibroblast growth factor (FGF) pathways in general are implicated in many physiological processes, such as morphogenesis during development and angiogenesis which is the process of developing new blood vessels that involves the proliferation, migration, and tissue infiltration of capillary endothelial cells from pre-existing blood vessels. FGFs are some of the factors that have been implicated as possible regulators of angiogenesis along with transforming growth factor (TGF), vascular endothelial growth factor (VEGF), and platelet derived growth factor (PDGF). FGF pathways are also implicated in neuronal survival and wound healing. They are also thought to be important in a number of pathological processes.

In particular, FGFR-1 has been implied to be involved in diseases such as cancers and arthritis. Although the involvement of FGF pathways in metabolism, such as feeding behavior and adipose tissue development has been suggested, it is not clear whether these findings entail fundamental mechanisms through which metabolism is regulated. For example, a recent study performed in mice has shown that injections of FGF-2, in combination with basement membrane proteins, can induce development of new adipose tissue at the site of the injection. This suggests that locally produced FGFs may act in a paracrine manner to affect adipogenesis and thereby influence the regional distribution of adipose tissue in the body and the relationship between adipose tissue and insulin resistance is well-established, both of which are strongly implicated in type 2 diabetes and cardiovascular disease.

Fibroblast growth factor receptors (FGFRs) have common structural features and consist of an extracellular ligand-binding domain containing 2 or 3 Ig-like loops and a unique acid region, a trans-membrane domain, and the cytoplasmic region, which contains the tyrosine kinase catalytic domain and kinase insert. The FGFRs belong to Subclass IV of the receptor tyrosine kinase family of proteins. These receptors bind in an overlapping pattern to FGFs. It has been established that 22 FGFs act on 5 FGFRs in FGF ligand paracrine interaction.

FGFR-1 has two alternative splicing forms that differ from each other by the amino acid substitutions in the third IgG-like domain of the extracellular structure of the receptor designated IIIb and IIIc, FGFR-4 has only one. These substitutions constitute what is believed to be part of the binding domain of the receptor, and therefore are most likely to cause the two splicing forms to have distinct ligand specificities. The two forms have also been shown to be differentially expressed, which may be part of an exquisite control mechanism of complex functions mediated by FGFR-1.

Ligand binding, which is strengthened by the presence of heparin sulfate, causes the FGFRs to dimerize and activate specific intracellular signaling pathways (Bellot et al. 1991). The receptor becomes auto-phosphorylated and thus capable of activating downstream cellular pathways. Among different cellular responses, stimulation of proliferation or induction of differentiation is most commonly observed for FGFR-1 mediated signaling.

SUMMARY OF THE INVENTION

The present invention provides antibodies, or fragments thereof, specific for fibroblast growth factor receptor (FGFR)-1(IIIb), FGFR-1(IIIc), and/or FGFR-4(IIIc) as well as nucleic acids encoding these antibodies or fragments thereof. Vectors comprising such nucleic acids and host cells are also provided for production of these antibodies.

The present invention also provides a method of treating obesity (or an obesity related condition), diabetes (or a diabetes related condition) and/or a method to reduce food intake by administering to a mammal in need thereof a therapeutically effective amount of an FGFR-1 and/or FGFR-4 antagonist.

BRIEF DESCRIPTION OF THE FIGURES

FIG. 1 shows the amino acid and nucleic acid sequences of the Variable Regions and CDRs of FR1-H7. FIG. 1A shows the amino acid and DNA sequences of the Variable Region of the Heavy Chain of FR1-H7 (SEQ ID NOS:7 and 31). FIG. 1B shows the amino acid and DNA sequences of the Variable Region of the Light Chain of FR1-H7 (SEQ ID NOS:8 and 32). FIG. 1C shows the nucleic acid sequences of the CDRs of the variable region of the heavy chain and the variable region of the light chain of FR1-H7 (SEQ ID NOS:25-30). FIG. 1D shows the amino acid sequences of the CDRs of the variable region of the heavy chain and the variable region of the light chain of FR1-H7 (SEQ ID NOS:1-6).

FIG. 2 shows the amino acid and nucleic acid sequences of the Variable Regions of FR1-A1. FIG. 2A shows the amino acid and DNA sequences of the Variable Region of the Heavy Chain of FR1-A1 (SEQ ID NOS:15 and 39). FIG. 2B shows the amino acid and DNA sequences of the Variable Region of the Light Chain of FR1-A1 (SEQ ID NOS:16 and 40). FIG. 1C shows the nucleic acid sequences of the CDRs of the variable region of the heavy chain and the variable region of the light chain of FR1-A1 (SEQ ID NOS:33-38). FIG. 1D shows the amino acid sequences of the CDRs of the variable region of the heavy chain and the variable region of the light chain of FR1-A1 (SEQ ID NOS:9-14).

FIG. 4 shows binding of recombinant FGFR-1 to FGF ligand as determined using the ELISA blocking assay.

FIG. 5 shows binding of $^{125}$I-FGF-2 to cell surface FGFR-1.

FIG. 6 shows a Western blot of FGFR-1 phosphorylation. The upper blot was probed with anti-phospho-Tyrosine antibody and the lower blot shows control protein bands in the cell lysates for estimation of relative gel loading.

FIG. 8 shows proliferation of adipocytes in vitro.

FIG. 12 shows the effect of FR1-H7 on blood glucose.

FIG. 26 shows treatment of C57 black mice with FR1-H7, which caused decreases in body weights, food intake, muscle and fat mass, energy expenditure, ambulatory activities and Respiratory Exchange Ratio (RER) as compared to the control. FIG. 26E shows decrease in oxygen consumption and RER with FR1-H7 treatment as compared to control.

FIG. 27 shows a paired-feeding of FR1-H7 and control treated animals resulting in identical decreases in body weights, muscle and fat mass, and energy expenditure between the two groups. Both groups also exhibited similar decreases in ambulatory activities and RER. FIG. 27B shows a decrease in fat and muscle weights of both FR1-H7 treated and control animals.

FIG. 28 shows the amino acid and nucleic acid sequences of the Variable Regions and the Variable Region CDRs of FR1-4H. FIG. 28A shows the amino acid and nucleic acid sequences of the Variable Region of the Heavy Chain of FR1-4H and the Variable Region of the Light Chain of FR1-4H (SEQ ID NOS:23-24 and 47-48). FIG. 28B shows the amino acid and nucleic acid sequences of the CDRs of the Variable Region of the Heavy and Light Chains of FR1-4H (SEQ ID NOS:17-22 and 41-46).

FIG. 30 shows examples of FGFR small molecule inhibitors including indolinone derivatives, quinolinone derivatives and pyrimido-pyridine derivatives.

FIG. 31 shows that FGFR small molecule inhibitors inhibited the auto-phosphorylation of FGFR-1(IIIc) in a cell-based phosphorylation assay. Equal amounts of cell lysate were applied to each sample lane. Receptor auto-phosphorylation was probed using anti-phospho-tyrosine antibody as described in Example 20.

DETAILED DESCRIPTION OF THE INVENTION

Figure 3:
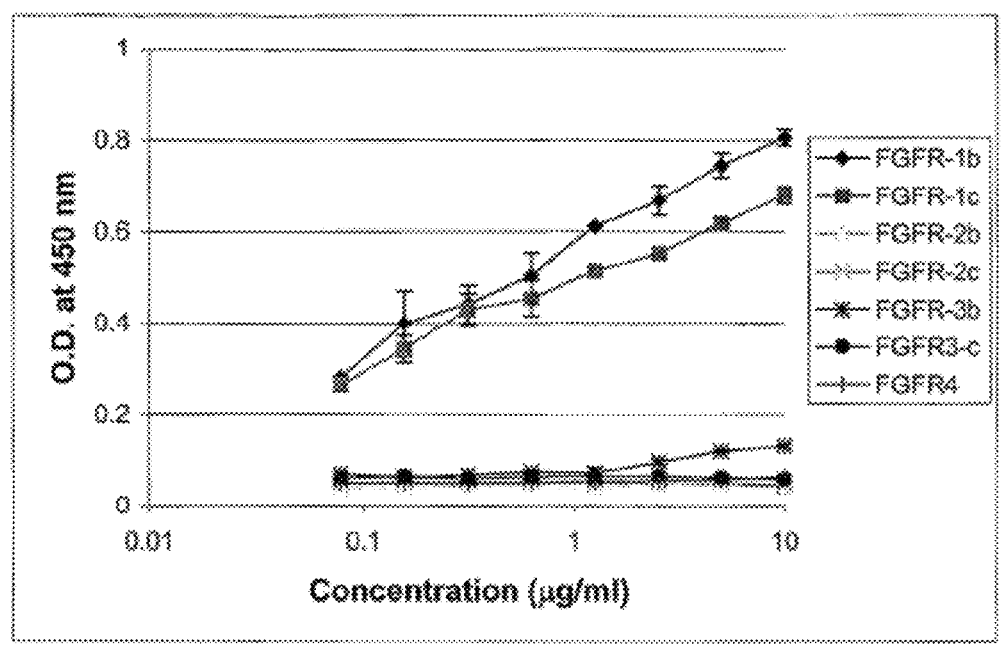
FIG. 3 shows binding of FR1-H7 antibody to FGFRs as determined using the ELISA binding assay. Each data point is an average of duplicates and error bars are standard deviations.

The present invention provides purified antibodies, or fragments thereof, specific for fibroblast growth factor receptor (FGFR)-1(IIIb), FGFR-1(IIIc), or FGFR-4(IIIc). An example of an antibody that is specific for FGFR-1(IIIb) and/or FGFR-1(IIIc), and/or FGFR-4(IIIc) is FR1-H7 (FIG. 1). It should be appreciated that the description herein with respect to FR1-H7 applies to all antibodies specific for FGFR-1(IIIb) and/or FGFR-1(IIIc). FR1-A1 is an example of an antibody specific for FGFR-1(IIIc) and/or FGFR-4(IIIc) (FIG. 2). Similarly to FR1-H7, any description herein with respect to FR1-A1 applies to all antibodies specific for FGFR-1(IIIc) and/or FGFR-4(IIIc). FR1-4H is an example of an antibody of the invention specific for at least FGFR(IIIb) (FIG. 28). Preferably, the antibodies, or fragments thereof, of the present invention bind to an extracellular domain of FGFR-1(IIIb), FGFR-1(IIIc), or FGFR-4(IIIc) and neutralize activation of the receptor. More preferably, the antibodies, or fragments thereof, of the present invention inhibit binding of a ligand of FGFR-1(IIIb), FGFR-1(IIIc), or FGFR-4(IIIc) to its receptor.

Naturally occurring antibodies typically have two identical heavy chains and two identical light chains, with each light chain covalently linked to a heavy chain by an interchain disulfide bond and multiple disulfide bonds further link the two heavy chains to one another. Individual chains can fold into domains having similar sizes (110-125 amino acids) and structures, but different functions. The light chain can comprise one variable domain ($V_L$) and/or one constant domain ($C_L$). The heavy chain can also comprise one variable domain ($V_H$) and/or, depending on the class or isotype of antibody, three or four constant domains ($C_H1$, $C_H2$, $C_H3$ and $C_H4$). In humans, the isotypes are IgA, IgD, IgE, IgG, and IgM, with IgA and IgG further subdivided into subclasses or subtypes ($IgA_{1-2}$ and $IgG_{1-4}$).

Generally, the variable domains show considerable amino acid sequence variability from one antibody to the next, particularly at the location of the antigen-binding site. Three regions, called hypervariable or complementarity-determining regions (CDRs), are found in each of $V_L$ and $V_H$, which are supported by less variable regions called framework variable regions.

The portion of an antibody consisting of $V_L$ and $V_H$ domains is designated Fv (Fragment variable) and constitutes the antigen-binding site. Single chain Fv (scFv) is an antibody fragment containing a $V_L$ domain and a $V_H$ domain on one polypeptide chain, wherein the N terminus of one domain and the C terminus of the other domain are joined by a flexible linker (see, e.g., U.S. Pat. No. 4,946,778 (Ladner et al.); WO 88/09344, (Huston et al.). WO 92/01047 (McCafferty et al.) describes the display of scFv fragments on the surface of soluble recombinant genetic display packages, such as bacteriophage.

The peptide linkers used to produce the single chain antibodies can be flexible peptides selected to assure that the proper three-dimensional folding of the $V_L$ and $V_H$ domains occurs. The linker is generally 10 to 50 amino acid residues. Preferably, the linker is 10 to 30 amino acid residues. More preferably the linker is 12 to 30 amino acid residues. Most preferably is a linker of 15 to 25 amino acid residues. An example of such linker peptides includes repeats of four Glycines followed by Serine.

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Multiple single chain antibodies, each single chain having one $V_H$ and one $V_L$ domain covalently linked by a first peptide linker, can be covalently linked by at least one or more peptide linker to form multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of amino acid residues is about one hundred.

Two single chain antibodies can be combined to form a diabody, also known as a bivalent dimer. Diabodies have two chains and two binding sites, and can be monospecific or bispecific. Each chain of the diabody includes a $V_H$ domain connected to a $V_L$ domain. The domains are connected with linkers that are short enough to prevent pairing between domains on the same chain, thus driving the pairing between complementary domains on different chains to recreate the two antigen-binding sites.

Three single chain antibodies can be combined to form triabodies, also known as trivalent trimers. Triabodies are constructed with the amino acid terminus of a $V_L$ or $V_H$ domain directly fused to the carboxyl terminus of a $V_L$ or $V_H$ domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

Fab (Fragment, antigen binding) refers to the fragments of the antibody consisting of $V_L$ $C_L$ $V_H$ $C_{H1}$ domains. Those generated following pepsin digestion simply are referred to as Fab and do not retain the heavy chain hinge region. Following pepsin digestion, various Fabs retaining the heavy chain hinge are generated. Those fragments with the interchain disulfide bonds intact are referred to as $F(ab')_2$, while a single Fab' results when the disulfide bonds are not retained. $F(ab')_2$ fragments have higher avidity for antigen than the monovalent Fab fragments.

Fc (Fragment crystallization) is the designation for the portion or fragment of an antibody that comprises paired heavy chain constant domains. In an IgG antibody, for example, the Fc comprises $C_{H2}$ and $C_{H3}$ domains. The Fc of an IgA or an IgM antibody further comprises a $C_{H4}$ domain. The Fc is associated with Fc receptor binding, activation of complement-mediated cytotoxicity and antibody-dependent cellular-cytoxicity (ADCC). For antibodies such as IgA and IgM, which are complexes of multiple IgG like proteins, complex formation requires Fc constant domains.

Finally, the hinge region separates the Fab and Fc portions of the antibody, providing for mobility of Fabs relative to each other and relative to Fc, as well as including multiple disulfide bonds for covalent linkage of the two heavy chains.

Thus, antibodies of the invention include, but are not limited to, naturally occurring antibodies, bivalent fragments such as $(Fab)_2$, monovalent fragments such as Fab, single chain antibodies, single chain Fv (scFv), single domain antibodies, multivalent single chain antibodies, diabodies, triabodies, and the like that bind specifically with antigens. Antibody fragments also include polypeptides with amino acid sequences substantially similar to the amino acid sequence of the variable or hypervariable regions of the antibodies of the invention. Substantially the same amino acid sequence is defined herein as a sequence with at least 70%, preferably at least about 80%, and more preferably at least about 90% homology to a compared amino acid sequence, as determined by the FASTA search method in accordance with Pearson and Lipman, Proc. Natl. Acad. Sci. USA 85, 2444-2448 (1988) and which binds to FGFR-1 and/or FGFR-2.

The antibodies, or fragments thereof, of the present invention are specific for FGFR-1(IIIb), FGFR-1(IIIc), and/or FGFR-4(IIIc). Antibody specificity refers to selective recognition of the antibody for a particular epitope of an antigen. Antibodies, or fragments thereof, of the present invention, for example, can be monospecific or bispecific. Bispecific antibodies (BsAbs) are antibodies that have two different antigen-binding specificities or sites. Where an antibody has more than one specificity, the recognized epitopes can be associated with a single antigen or with more than one antigen. Thus, the present invention provides bispecific antibodies, or fragments thereof, that bind to two different antigens, with at least one specificity for FGFR-1(IIIb), FGFR-1(IIIc), and/or FGFR-4(IIIc).

Specificity of the present antibodies, or fragments thereof, for FGFR can be determined based on affinity and/or avidity. Affinity, represented by the equilibrium constant for the dissociation of an antigen with an antibody ($K_d$), measures the binding strength between an antigenic determinant and an antibody-binding site. Avidity is the measure of the strength of binding between an antibody with its antigen. Avidity is related to both the affinity between an epitope with its antigen binding site on the antibody, and the valence of the antibody, which refers to the number of antigen binding sites of a particular epitope. Antibodies typically bind with a dissociation constant ($K_d$) of $10^{-5}$ to $10^{11}$ liters/mol (e.g., $K_D$<100 nM). Any $K_d$ less than $10^{-4}$ liters/mol is generally considered to indicate nonspecific binding. The lesser the value of the $K_d$, the stronger the binding strength between an antigenic determinant and the antibody binding site.

The present invention provides a purified antibody, or fragment thereof, specific for FGFR-1(IIIb) and/or FGFR-1(IIIc), and/or FGFR-4(IIIc), wherein the antibody binds to an extracellular domain of an FGFR1-(IIIb) and/or FGFR1-(IIIc) and/or FGFR-4(IIIc) and neutralizes activation of the receptor. The present invention also provides a purified antibody or fragment thereof, specific for FGFR-1(IIIc) and/or FGFR-4 (IIIc) (FR1-A1), wherein the antibody binds to an extracellular domain of an FGFR-1(IIIc) and/or FGFR-4(IIIc) and neutralizes activation of the receptor. The present invention also provides a purified antibody or fragment thereof, specific for at least FGFR-1(IIIb) (FR1-4H), wherein the antibody binds to an extracellular domain of at least an FGFR-1(IIIb) and neutralizes activation of the receptor. In this specification, neutralizing a receptor means inactivating the intrinsic kinase activity of the receptor to transduce a signal. A reliable assay for FGFR-1 or FGFR-4 neutralization is the inhibition of receptor phosphorylation. The present invention is not limited by any particular mechanism of FGFR neutralization. Some possible mechanisms include preventing binding of the FGF ligand to the extracellular binding domain of the FGF receptor, inducing the internalization of the receptors, and preventing dimerization or oligomerization of receptors.

Neutralization of FGF activation of an FGFR-1 or FGFR-4 can be determined by any suitable method. For example, neutralization of FGF activation of an FGFR in a sample of endothelial or non-endothelial cells, such as in adipose tissue or tumor cells, may be performed in vitro or in vivo. Such neutralizing in a sample of FGFR-1 or FGFR-4 expressing cells involves contacting the cells with an antibody of the invention. In vitro, the cells are contacted with the antibody before, simultaneously with, or after, adding FGF to the cell sample.

Further, the invention provides the antibody of the invention inhibits binding of a ligand of FGFR1-(IIIb) and/or FGFR1-(IIIc) or FGFR1-(IIIc) and/or FGFR4 to its receptor. The antibody may be of an alternative splicing form containing the ligand binding function. Some examples of the ligands of FGFR1-(IIIb) include the protein fibroblast growth factor (FGF)-1, -2, -3 and -10. Some examples of the ligands of FGFR1-(IIIc) include FGF-1, -2, -4, -5, and -6. Some examples of the ligands of FGFR4-(IIIa) include FGF-1, -2, -4, -6, -8b, -8e, -8f, -9, -16, -17b, and -19. (See Endocrine-Related Cancer (2000) 7 165-197 at 165-169, "Fibroblast growth factors, their receptors and signaling" C. J. Powers, S. W. McLeskey and A. Wellstein).

In a preferred embodiment, one, two, three, four, five, or all six complementarity-determining regions (CDR) of the present antibodies have sequences selected from the group consisting of SEQ ID NO:1, SEQ ID NO:2, SEQ ID NO:3, SEQ ID NO:4, SEQ ID NO:5, and SEQ ID NO:6 (i.e., any one of the CDRs of FR1-H7). In an alternatively preferred embodiment, one, two, three, four, five, or all six complementarity-determining regions (CDR) of the present antibodies have sequences selected from the group consisting of SEQ ID NO:9, SEQ ID NO:10, SEQ ID NO:11, SEQ ID NO:12, SEQ ID NO:13, and SEQ ID NO:14 (i.e., any one of the CDRs of FR1-A1). In an alternatively preferred embodiment, one, two, three, four, five, or all six complementarity-determining regions (CDR) of the present antibodies have sequences selected from the group consisting of SEQ ID NO:17, SEQ ID NO:18, SEQ ID NO:19, SEQ ID NO:20, SEQ ID NO:21, and SEQ ID NO:22 (i.e., any one of the CDRs of FR1-4H).

The antibodies of the present invention, in another preferred embodiment, have a heavy chain variable region sequence of SEQ ID NO:7 (i.e., the heavy chain variable region of FR1-H7) and/or a light chain variable region sequence of SEQ ID NO:8 (i.e., the light chain variable region of FR1-H7). Alternatively, the antibodies of the present invention preferably have a heavy chain variable region sequence of SEQ ID NO:15 (i.e., the heavy chain variable region of FR1-A1) or a light chain variable region sequence of SEQ ID NO:16 (i.e., the light chain variable region of FR1-A1). Alternatively, the antibodies of the present invention preferably have a heavy chain variable region sequence of SEQ ID NO:23 (i.e., the heavy chain variable region of FR1-4H) or a light chain variable region sequence of SEQ ID NO:24 (i.e., the light chain variable region of FR1-4H).

The nucleic acid and amino acid sequences of the CDRs and variable heavy and light chains of the antibodies are described in sequences listed in SEQ ID NO:1 to 48. Also, the invention provides an isolated nucleic acid encoding the antibody of the invention, antibody equivalents or fragments thereof (SEQ ID NO:25-48). The nucleic acids that encode for the heavy and light chains of the antibodies of the invention or their equivalents are obtained by standard molecular biology techniques. Nucleic acid molecules of the invention include those that bind under stringent conditions to SEQ ID NOS:25-48 and which encode functionally equivalent polypeptide antibody subunits capable of binding to FGFR-1(IIIb), FGFR-(IIIc) and/or FGFR-4(IIIc). Stringent conditions denotes conditions for hybridization such as, hybridization to filter-bound DNA in 0.5M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.20.3) or for moderately stringent conditions, washing in 0.2 SSC/0.1% SDS at 42° C. (Ausubel et al., 1989 supra).

The monoclonal antibodies of the invention, e.g., FR1-H7, FR1-A1 and FR1-4H, may be produced by methods known in the art. These methods include immunological methods described by Kohleer and Milstein in Nature 256, 495-497 (1975) and Campbell in "Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam (1985); as well as by the recombinant DNA method described by Huse et al. in Science 246, 1275-1281 (1989).

The antibodies of the invention may be prepared by immunizing a mammal with a soluble FGFR-1(IIIb), FGFR-1 (IIIc), or FGFR-4(IIIc). The soluble receptors may be used by themselves as immunogens, or attached to a carrier protein or other objects, such as beads, i.e. sepharose beads. After the mammal has produced antibodies, a mixture of antibody producing cells, such as splenocytes, are isolated. Monoclonal antibodies may be produced by isolating individual antibody-producing cells from the mixture and immortalizing them by, for example, fusing them with tumor cells, such as myeloma cells. The resulting hybridomas are preserved in culture, and express monoclonal antibodies, which are harvested from the culture medium.

The antibodies may also be prepared from FGFR-1(IIIb), FGFR-1(IIIc), or FGFR-4(IIIc) bound to the surface of cells that express the FGFR-1(IIIb), FGFR-1(IIIc), or FGFR-4 (IIIc). The cell to which these receptors may be bound may be a cell known to preferentially express individual receptors, for example, the human FGFR-1(IIIb) is expressed on cells such as fibroblast cells, endothelial cells, certain epithelial cells, flg-1, cek-1, vascular smooth muscle cells, lymphocytes, the human FGFR-1(IIIc) is expressed on cells such as macrophage cells, hematopoietic progenitor cells, and numerous tumor cells, and the human FGFR-4(IIIc) is expressed on cells such as embryonic and multipotential stem cells. (See R& D Systems, Cytokine Mini-Review, 2001 "FGFR expression") Alternatively, the cell to which the receptor is bound may be a cell into which the DNA encoding the FGFR-1(IIIb), FGFR-1(IIIc), or FGFR-4(IIIc) has been transfected.

The FGFR-1(IIIb), FGFR-1(IIIc), or FGFR-4(IIIc) may be used as an immunogen to raise an antibody of the invention. The receptor peptide may be obtained from natural sources, such as from cells that express the above receptors. Also, a synthetic receptor peptide may be obtained using commercially available machines and the corresponding amino acid sequence. (See Endocrine-Related Cancer (2000)7 165-197, at 174.) A further alternative still, is that a nucleic acid encoding a FGFR-1(IIIb), FGFR-1(IIIc), or FGFR-4(IIIc) such as a cDNA or a fragment thereof, may be cloned and expressed and the resulting polypeptide recovered and used as an immunogen to raise an antibody of the invention. In order to prepare the above receptors against which the antibodies are made, nucleic acid molecules that encode the FGFR-1(IIIb), FGFR-1(IIIc), or FGFR-4(IIIc), or portions thereof, especially the extracellular portions thereof, may be inserted into known vectors for expression in host cells using standard recombinant DNA techniques. Suitable sources of such nucleic acid molecules include cells that express FGFR-1(IIIb), FGFR-1 (IIIc), or FGFR-4(IIIc).

The present invention also provides an expression vector containing a nucleic acid encoding an antibody, or fragment thereof, of the present invention operably linked to a control sequence, as well as a host cell containing such an expression vector. These host cells can be cultured under specific conditions permitting expression of antibodies, or fragments thereof, of the present invention and the antibodies then can be purified from the host cells.

Again, standard recombinant techniques and known expression vectors are used to express the antibodies of the invention. Vectors for expressing proteins in bacteria, especially E. coli, are known. Such vectors include the PATH vectors described by Dieckmann and Tzagoloff in J. Biol. Chem. 260, 1513-1520 (1985). These vectors contain DNA sequences that encode anthranilate synthetase (TrpE) followed by a polylinker at the carboxy terminus. Other expression vector systems are based on beta-galactosidase (pEX); lambda $P_L$; maltose binding protein (pMAL); and glutathione S-transferase (pGST)—see Gene 67, 31 (1988) and Peptide Research 3, 167 (1990).

Vectors useful in yeast are available. A suitable example is the 2μ plasmid. Suitable vectors for expression in mammalian cells are also known. Such vectors include well-known derivatives of SV-40, adenovirus, retrovirus-derived DNA sequences and shuttle vectors derived from combination of functional mammalian vectors, such as those described above, and functional plasmids and phage DNA.

Further eukaryotic expression vectors are known in the art (e.g., P. J. Southern and P. Berg, J. Mol. Appl. Genet. 1, 327-341 (1982); S. Subramani et al., Mol. Cell. Biol. 1, 854-864 (1981); R. J. Kaufmann and P. A. Sharp, "Amplification And Expression Of Sequences Cotransfected with A Modular Dihydrofolate Reductase Complementary DNA Gene," J. Mol. Biol. 159, 601-621 (1982); R. J. Kaufmann and P. A. Sharp, "Amplification And Expression Of Sequences Cotransfected with A Modular Dihydrofolate Reductase Complementary DNA Gene," J. Mol. Biol. 159, 601-664 (1982); S. I. Scahill et al., "Expression And Characterization Of the Product Of A Human Immune Interferon DNA Gene In Chinese Hamster Ovary Cells," Proc. Natl. Acad. Sci. USA 80, 4654-4659 (1983); G. Urlaub and L. A. Chasin, Proc. Natl. Acad. Sci. USA 77, 4216-4220, (1980)).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alphamating factors, and promoters derived from polyoma, adenovirus, retrovirus, and simian virus, e.g., the early and late promoters or SV40, and other sequences known to control the expression of genes of prokaryotic or eukaryotic cells and their viruses or combination thereof.

Vectors containing the control signals and DNA to be expressed, such as that encoding antibodies of the invention, antibody equivalents thereof, or FGFR-1(IIIb), FGFR-1 (IIIc), or FGFR-4(IIIc), are inserted into a host cell for expression. Some useful expression host cells include well-known prokaryotic and eukaryotic cells. Some suitable prokaryotic hosts include, for example, E. coli, such as E. coli SG-936, E. coli HB 101, E. coli W3110, E. coli X1776, E. coli X2282, E. coli DHI, and E. coli MRC1, Pseudomonas, Bacillus, such as Bacillus subtilis, and Streptomyces. Suitable eukaryotic cells include yeast and other fungi, insect, animal cells, such as COS cells and CHO cells, human cells and plant cells in tissue culture.

A method of producing an antibody comprising culturing the host cell comprising the vector comprising the nucleic acid sequence encoding for the antibodies of the invention under conditions permitting expression of the antibody. Following expression in a host cell maintained in a suitable medium, the polypeptide or peptide to be expressed, such as that encoding the antibodies of the invention, antibody equivalents thereof, or FGFR-1(IIIb), FGFR-1(IIIc), or FGFR-4(IIIc), may be isolated from the medium, and purified by methods known in the art. If the polypeptide or peptide is not secreted into the culture medium, the host cells are lysed prior to isolation and purification.

This invention further provides a pharmaceutical composition comprising the antibody of this invention or fragment thereof and a pharmaceutically acceptable carrier.

Carrier as used herein includes pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants such as TWEEN®, polyethylene glycol (PEG), and PLURONICS®.

The active ingredients may also be entrapped in microcapsules prepared, for example, by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nanoparticles, and nanocapsules) or in macroemulsions. The formulations to be used for in vivo administration must be sterile. This is readily accomplished by filtration through sterile filtration membranes. Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization maybe achieved by modifying sulfhydryl residues, lyophilizing from acidic solutions, controlling moisture content, using appropriate additives, and developing specific polymer matrix compositions.

A method of identifying FR1-H7, FR1-A1 or FR1-4H or fragments thereof can involve providing a library of antibody fragments, screening the library for an antibody that is specific for FGFR1-IIIb and/or FGFR1-IIIc or FGFR1-(IIIc) and/or FGFR-4(IIIc), and purifying the antibody that is specific for FGFR1-IIIb and/or FGFR1-Inc or FGFR1-(IIIc) and/or FGFR-4(IIIc). Thus, the present invention also provides a method of identifying a fibroblast growth factor receptor (FGFR)-1(IIIb), FGFR-1(IIIc), or FGFR-4(IIIc) specific antibody, or fragment thereof, which is as follows: (i) providing a library of antibody fragments, (ii) screening the library for the antibody that is specific for FGFR-1(IIIb) and/or FGFR-1(IIIc) or the antibody specific for FGFR-1(IIIc) and/or FGFR-4, and (iii) purifying the antibody that is specific for FGFR-1(IIIb) and/or FGFR-1(IIIc) or the antibody specific for FGFR-1(IIIc) and/or FGFR-4. Screening the library can involve (i) providing an affinity matrix having the FGFR-1(IIIb), FGFR-1(IIIc), and/or FGFR-4 bound to a solid support, (ii) contacting the affinity matrix with the library of antibody fragments, and (iii) separating the antibody fragments that bind to the affinity matrix from the antibody fragments that do not bind the affinity matrix. These methods can be used to identify an antibody.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by the introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10,779-783 (1992); Lonberg et al., Nature 368856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

A purified antibody is one that has been identified and separated and/or recovered from a component of its natural environment. Contaminant components of its natural environment, materials that would interfere with diagnostic or therapeutic uses for the antibody, and may include enzymes, hormones, and other proteinaceous or non-proteinaceous solutes, generally have been removed.

The monoclonal antibodies of the invention secreted by the subclones may be isolated or purified from the culture medium or ascites fluid by conventional immunoglobulin purification procedures such as, for example protein A-Sepharose, hydrolyapatite chromatography, gel electrophoresis, dialysis, or affinity chromatography.

The present invention further provides the method of identifying and isolating FR1-H7 and/or FR1-A1 and/or FR1-4H, wherein the screening of the library comprises providing an affinity matrix having the FGFR1-(IIIb), FGFR1-(IIIc), FGFR-4(IIIc), and/or alternative splicing form containing ligand binding function bound to a solid support, contacting the affinity matrix with the library of antibody fragments, and separating the antibody fragments that bind to the affinity matrix from the antibody fragments that do not bind the affinity matrix.

By solid support is meant a non-aqueous matrix to which the FGFR-1(IIIb), FGFR-1(IIIc), or FGFR-4(IIIc) can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

Methods of treatment involving administration to a mammal in need thereof of a therapeutically effective amount of a FGFR-1(IIIb), FGFR-1(IIIc), and/or FGFR-4 antagonist are also provided by the present invention. Conditions for which these methods are useful include obesity or an obesity related condition, and diabetes or a diabetes related condition. Specific conditions include, but are not limited to hypertension, cardiovascular disease, and angiogenesis. The methods are also useful for reducing food intake, body mass index, or altering energy metabolism. Moreover, these methods can be useful in modulating serum triglycerides and leptin levels.

An obesity related condition refers to a condition, which is the result of or which is exasperated by obesity, such as, but not limited to dermatological disorders such as infections, varicose veins, Acanthosis nigricans, and eczema, exercise intolerance, diabetes (Type 2), insulin resistance, hypertension, hypercholesterolemia, cholelithiasis, orthopedic injury, thromboembolic disease, cancer, and coronary (or cardiovascular) heart disease, particularly those cardiovascular conditions associated with high triglycerides and free fatty acids in an individual, Arthritis, daytime sleepiness, sleep apnea, end stage renal disease, gallbladder disease, gout, heat disorders, impaired immune response, impaired respiratory function, infections following wounds, infertility, liver disease, lower back pain, obstetric and gynecologic complications, pain, pancreatitis, stroke, surgical complications, urinary stress incontinence, gastro-intestinal disorders.

Treatment means any treatment of a disease in an animal and includes: (1) preventing the disease from occurring in a mammal which may be predisposed to the disease but does not yet experience or display symptoms of the disease; e.g., prevention of the outbreak of the clinical symptoms; (2) inhibiting the disease, e.g., arresting its development; or (3) relieving the disease, e.g., causing regression of the symptoms of the disease.

Effective amount for the treatment of a disease means that amount which, when administered to a mammal in need thereof, is sufficient to effect treatment, as defined above, for that disease.

Also, the present invention provides a method of treating diabetes (type 2) or a diabetes (type 2) related condition comprising administering to a mammal in need thereof a therapeutically effective amount of an FGFR-1(IIIb), FGFR-1(IIIc), FGFR-4(IIIc) and/or alternative splicing form containing ligand binding function antagonist.

A diabetes related condition refers to a condition, which is the result of or which is exasperated by diabetes, such as, but not limited to heart and blood vessel disease, heart attack, stroke, poor blood circulation in legs and feet, high blood pressure, hypertension, blindness or vision problems, kidney failure or infection, urinary bladder infection, nerve damage, slow healing wounds, foot infections, or gum infections.

Also, the present invention provides a method of reducing food intake comprising administering to a mammal in need thereof a therapeutically effective amount of an antagonist of FGFR-1(IIIb), FGFR-1(IIIc), FGFR-4(IIIc) and/or an alternative splicing form having ligand binding function antagonist.

The identification of mammals in need of treatment is well within the ability and knowledge of one skilled in the art. For example, human individuals who are either suffering from clinically significant obesity and diabetes such as hypertension, cardiovascular disease, blood glucose levels, body mass, serum triglyceride levels, angiogenesis, and/or energy metabolism (or other related disease) or who are at risk of developing clinically such significant disease are suitable for administration of the present antagonist. A clinician skilled in the art can readily determine, for example, by the use of clinical tests, physical examination and medical/family history, if an individual is a patient has such disease.

Further, the present invention provides a method of treatment to affect conditions related to obesity and diabetes such as hypertension, cardiovascular disease, blood glucose levels, body mass, serum triglyceride levels, angiogenesis, and/or energy metabolism.

Angiogenesis is the process of developing new blood vessels that involves the proliferation, migration and tissue infiltration of capillary endothelial cells from pre-existing blood vessels.

In the context of the present inventive methods, the antagonist can be a biological molecule or a small molecule that blocks FGFR-1(IIIb), FGFR-1(IIIc), and/or FGFR-4 signaling. Preferred biological molecules are antibodies or fragment thereof, including the antibodies and fragments thereof described herein. The small molecules suitable in the present methods binds FGFR-1(IIIb), FGFR-1(IIIc), and/or FGFR-4 internally, inhibits FGFR-1(IIIb), FGFR-1(IIIc), and/or FGFR-4 phosphorylation. In addition, the small molecule FGFR-1 antagonists inhibit binding of ATP to FGFR-1(IIIb), FGFR-1(IIIc), and/or FGFR-4, which can involve competing with ATP for FGFR-1(IIIb), FGFR-1(IIIc), and/or FGFR-4. Ultimately, these small molecule antagonists of FGFR-1 (IIIb), FGFR-1(IIIc), and/or FGFR-4 inhibit tyrosine kinase activity. Preferred small molecules include SU-6668, PD-173074, SU-5402, CHIR-258, PD-166285 or derivatives A or B of pyrimido-pyridine as described in FIG. 30.

The present invention also provides a method of treatment, wherein the antagonist is a small molecule that blocks FGFR-1 or FGFR-4 signaling. The FGFR-1 or FGFR-4 signaling is blocked by a method wherein the FGFR-1 and/or FGFR-4 antagonist binds the FGFR-1 and/or FGFR-4 internally, inhibits the FGFR-1 and/or FGFR-4 phosphorylation, inhibits binding of ATP to FGFR-1 and/or FGFR-4, competes with ATP for the FGFR-1 and/or FGFR-4, and/or inhibits the FGFR-1 and/or FGFR-4 tyrosine kinase activity.

Further, the present invention provides the method of treatment wherein the small molecule is selected from the group consisting of pyrimido-pyridines, quinolinones, indolinones such as those shown in FIG. 30, as well as, SU-6668 (3-[2,4-Dimethyl-5-(2-oxo-1,2-dihydro-indol-3-ylidenemethyl)-1H-pyrrol-3-yl]-propionic acid), PD-173074 (1-tert-Butyl-3-{6-(3,5-dimethoxy-phenyl)-2-[4-(ethyl-methyl-amino)-butylamino]-pyrido[2,3-d]pyrimidin-7-yl}-urea), SU-5402 (3-[4-Methyl-2-(2-oxo-1,2-dihydro-indol-3-ylidenemethyl)-1H-pyrrol-3-yl]-propionic acid), CHIR-258 (4-Amino-5-fluoro-3-[6-(4-methyl-piperazin-1-yl)-1H-benzoimidazol-2-yl]-1H-quinolin-2-one), PD-166285 (3-(2,6-Dichloro-phenyl)-7-[4-(2-diethylamino-ethoxy)-phenylamino]-1-methyl-1H-quinolin-2-one), Sugen Inc. U.S. Pat. Nos. 6,569,868, 6,599,902, 6,486,185, 6,514,981, 6,573,293; Institut Pasteur U.S. Pat. No. 6,559,126, Agouron Pharmaceuticals, Inc. U.S. Pat. Nos. 6,534,524, 6,462,060, 6,620,828, 6,531,491; Pharmacia & Upjohn Company U.S. Pat. No. 6,451,838; Ariad Pharmaceuticals, Inc. U.S. Pat. Nos. 6,576,766, 6,482,852, 6,573,295; Bridges et al. U.S. Pat. No. 6,602,863; Warner-Lambert Company U.S. Pat. No. 6,602,863; Pharmacia & Upjohn Co. U.S. Pat. No. 6,451,838.

The method of treatment described herein can be used to treat any suitable mammal, preferably the mammal is a human.

All patents and literature references cited in the present specification are hereby incorporated by reference in their entirety.

EXAMPLES

The following examples are offered for illustrative purposes only, and are not intended to limit the scope of the present invention in any way. The examples do not include detailed descriptions of conventional methods, such as those employed in the construction of vectors and plasmids, the insertion of genes encoding polypeptides into such vectors and plasmids, or the introduction of plasmids into host cells. Such methods are well known to those of ordinary skill in the art and are described in numerous publications including Sambrook, J., Fritsch, E. F. and Maniatis, T. (1989) Molecular Cloning: A laboratory Manual, $2^{nd}$ Edition, Cold Spring Harbor Laboratory Press.

Example 1

Assays

ELISA Screening Assay

Recombinant FGFs (R&D systems, Minneapolis, Minn.) were coated on Immulon® 2B microtiter plates (ThermoLab Systems, Franklin, Mass.) at concentrations of 0.5-2 µg/ml for 2 hrs. The plates were then washed with 0.2% Tween20/PBS, and blocked with 5% milk/PBS for 2 hrs before use. Phage or antibody was serially diluted with 5 µg/ml heparin (Sigma, St Louis, Mo.), 5% milk, PBS. Recombinant FGFR-1 (R&D Systems) was then added to a final concentration of 1 µg/ml. The mixture was incubated at room temperature for 1 hr before transfer to the FGF-2 coated plates, and incubated at room temperature for an additional 2 hrs. Plates were then washed 3 times with 0.2% Tween20/PBS. The bound receptors were detected using an anti-human Fc monoclonal antibody coupled with HRP (Pierce Biotechnology Inc., Rockford, Ill.) solution prepared according to supplier's instructions. Data were presented as % inhibition of ligand-receptor binding of the controls.

Binding Assay

Recombinant FGFRs (R&D systems) at a concentration of 1 µg/ml in PBS were coated on 96-well plates at room temperature for 2 hrs. The plates were washed 3 times with 0.2% Tween20/PBS, and blocked with 5% milk/PBS for 2 hrs before use. FR1-H7 or FR1-A1 was added to the plate and serially diluted in 0.2% Tween20/PBS. The plate was incubated at room temperature for 2 more hrs. The captured antibodies were detected using an anti-human light chain monoclonal antibody conjugated with ERP (Pierce Biotechnology, Rockford, Ill.) solution prepared according to supplier's instructions. The binding kinetics of the antibody to FGFR-1 was determined using a BiaCore® 3000 biosensor (BiaCore, Inc., Piscataway, N.J.) following the standard protocols suggested by the manufacturer. The Binding Kinetic (Kd) of FR1-H7 determined using BiaCore biosensor are as follows:

FGFR-1b: 60 pM
FGFR-1c: 40 pM
FGFR-2b: >1 µM
FGFR-2c: >1 µM
FGFR-3b: >1 µM
FGFR-3c: >1 µM
FGFR-4: 0.2 µM

Cell-Based Blocking Assay

An FGFR-1(IIIc) expressing cell line was constructed by retro-viral transfecting L6 (ATCC, Manassas, Va.) using a pBABE vector that has a puromycin resistant gene (Invitrogen). Transfected cells were cultured in 10% FBS, DMEM (Invitrogen) in 6-well tissue culture plates until reaching confluency. Before the blocking experiment, cells were serum starved for 8-24 hrs at 37° C. in DMEM medium that contains 0.1% FBS and 5 µg/ml heparin. Before the addition of any reagents, plates were put on ice for 1 hr to minimize receptor internalization. For binding experiment, iodinated recombinant FGF-2 was added at various concentrations to the wells of the plates. For blocking experiments, serially diluted FR1-H7 antibody was added and incubated with the cells on ice for 1 hr before iodinated recombinant FGF-2 was added to each well to a final concentration of 15 ng/ml. Binding was for 1 hr at 0-4° C., after which time the solutions were aspirated and the plates were washed 5 times with ice-cold PBS. Cells were lyzed with 0.5 ml ice-cold cell lysis buffer for 30 minutes. Radioactivity of the cell lysates was detected using a Wizard 1470 automatic gamma counter (Turku, Finland). Non-specific interaction was determined in a binding experiment in which iodinated FGF-2 was incubated with the cells in presence of 200 fold excess of cold ligand.

Phosphorylation Assay

FGFR-1 expressing L6 cells were cultured in 10% FBS, DMEM, in a 24-well tissue culture plate till confluency. Cells were Serum starved in 5 µg/ml heparin, 0.1% FBS, DMEM, for 8-24 hrs. Either FR1-H7 or FR1-A1 was added to the media and allowed to bind with the cell surface receptors at 37° C. for 1 hr. Cells were then stimulated with 20 ng/ml FGFs at 37° C. for 10 min before they were lyzed using ice-cold lysis buffer for 30 min. Cell lysate was subjected to SDS-PAGE followed by western blot. Membranes were probed with anti-phospho-tyrosine antibody (Cell Signaling Technology, Inc., Beverly, Mass.) for detection of phosphorylated FGFR-1 receptors according to supplier's instructions.

Proliferation Assay

Human umbilical vascular endothelial cells (HUVECs) were seeded in 96-well tissue culture plates at a concentration of $5 \times 10^4$ cells/ml. After attachment, cells were quiesced in EMG-2 medium lacking EGF, VEGF and FGF-2 (Cambrex, East Rutherford, N.J.) for 24 hrs. Quiescent media in wells were aspirated and replaced with EMG-2 that contained all the growth factors mentioned above. Antibodies were serially diluted and added to the wells. Cells were incubated at 37° C. with 5% $CO_2$ in a Muaire™ DH autoflow incubator (Cryostar Industries, Inc., White Hall, Pa.) for 48-72 hrs. Cell growth was determined by monitoring $^3$H-thymidine incorporation using a 1450 Micorbeta liquid scintillation counter (Perkin Elmer, Gaithersburg, Md.).

Two-week-old (after induced differentiation) grade 2 human adipocytes were obtained from Zen-Bio Inc. (Research Triangle, N.C.), and were maintained in the shipping media in a 96-well tissue culture plate. To evaluate the effects of FGF-2 on the proliferation of adipocytes, recombinant FGF-2 (R&D systems) was serially diluted and added to the wells of the plate. The cells were allowed to grow in the incubator for 60 hrs, before the level of $^3$H-thymidine incorporation was determined. To evaluate the effects of FR1-H7 on adipocytes proliferation, the antibody was serially diluted and added to the cells before addition of recombinant FGF-2 to a final concentration of 15 ng/ml. $^3$H-thymidine incorporation was determined after 60 hrs of incubation.

Mitogenesis Assay

Human astrocytoma G18 cells were seeded in 96-well tissue culture plates at a concentration of $5 \times 10^4$ cells/ml. After attachment, cells were quiesced for 24 hrs in RPMI media (Invitrogen) containing 0.1% FBS and 5 µg/ml heparin. Antibodies were serially diluted, added to the wells, and incubated with the cells at 37° C. for 1 hr. Recombinant FGF-2 was then added to a final concentration of 5 ng/ml. Cells were cultured in an incubator at 37° C. with 5% $CO_2$. Cell growth was determined 24 hrs later by monitoring $^3$H-thymidine incorporation as described previously.

Animal Studies—Food Consumption, Behavior, and Serum Glucose

Female athymic nude mice (Cr1:NU/NU-nuBR, Charles River Laboratories, Wilmington, Mass.) were housed 4-5 per cage. Mice were given autoclaved food (Lab Diet #5001, PMI Feeds Inc., St. Louis, Mo.) and water ad libitum. All animal use in this study was conducted in compliance with approved institutional animal care and use protocols, and according to NIH guidelines (*Guide for the Care and Use of Laboratory Animals*, NIH publication no. 86-23, 1985).

In one assay, mice were injected intraperitoneally (i.p.) with FR1-H7 at 0.19, 1.9, and 19 mg/kg body weight (n=5 per group). In another assay, mice were injected subcutaneously (s.c.) with the antibody, at 0.4, 4, and 40 mg/kg body weight. In control arms, mice were treated with saline i.p. or s.c. In addition, one group of mice was left untreated (n=4). All treatments were given at a volume of 10 μl/g body weight in Saline. Treatments were started on a Wednesday (Day 0) with additional treatments on the following Friday, Monday, Wednesday, and Friday. After this 9-day treatment period mice received no additional treatments.

Alternatively, female athymic nude mice were injected (i.p.) with saline, 2 mg/kg, or 20 mg/kg FR1-A1 on a Monday (Day 0) and Wednesday. Body weights were measured before the first injection, and on Day 2 and Day 5. Food intake per group was measured 2 days after the first injection.

The body weights of all animals were measured 3 times/week. Food consumption, behavior, and serum glucose were evaluated as follows. Food Intake Measurement: Prior to the treatment on Day 2 mice were placed in a new cage and the weight of the food container in the cage top was weighed. Prior to the treatment on Day 5 the weight of the food container was measured again. The difference in the Day 2 to Day 5 food container weight was divided by the number of mice per cage and the number of days between the measurements to give a food intake per mouse per 24 hrs. Activity Measurement: On Day 12, 3 days after the final treatment, mice were placed individually into a new cage and the number of rearings was counted over a 1 min period. Blood Glucose Measurement On Day 16, 7 days after the final treatment, non-fasted blood glucose was measured in blood collected from the tip of the tail using an Ascensia Elite XL blood glucose meter (glucose oxidase method, Bayer, Pittsburg, Pa.).

Animal Studies—Energy Expenditure and Body Composition

Figure 27A:
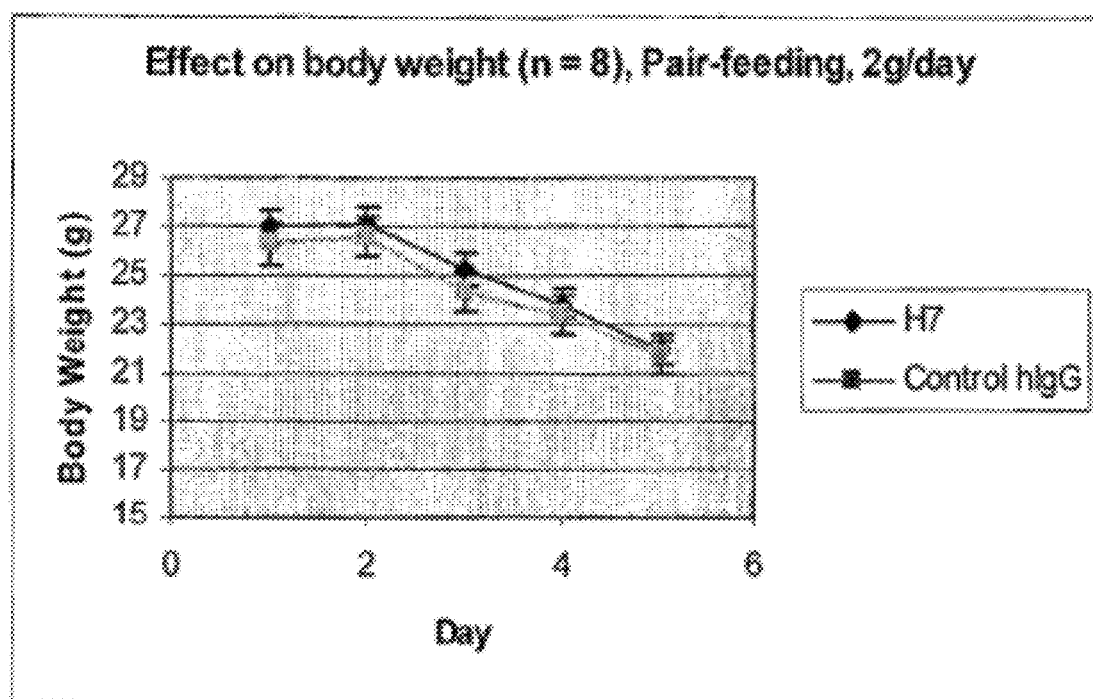
FIG. 27A shows decrease in daily body weight of both FR1-H7 treated and control animals.
Figure 27C:
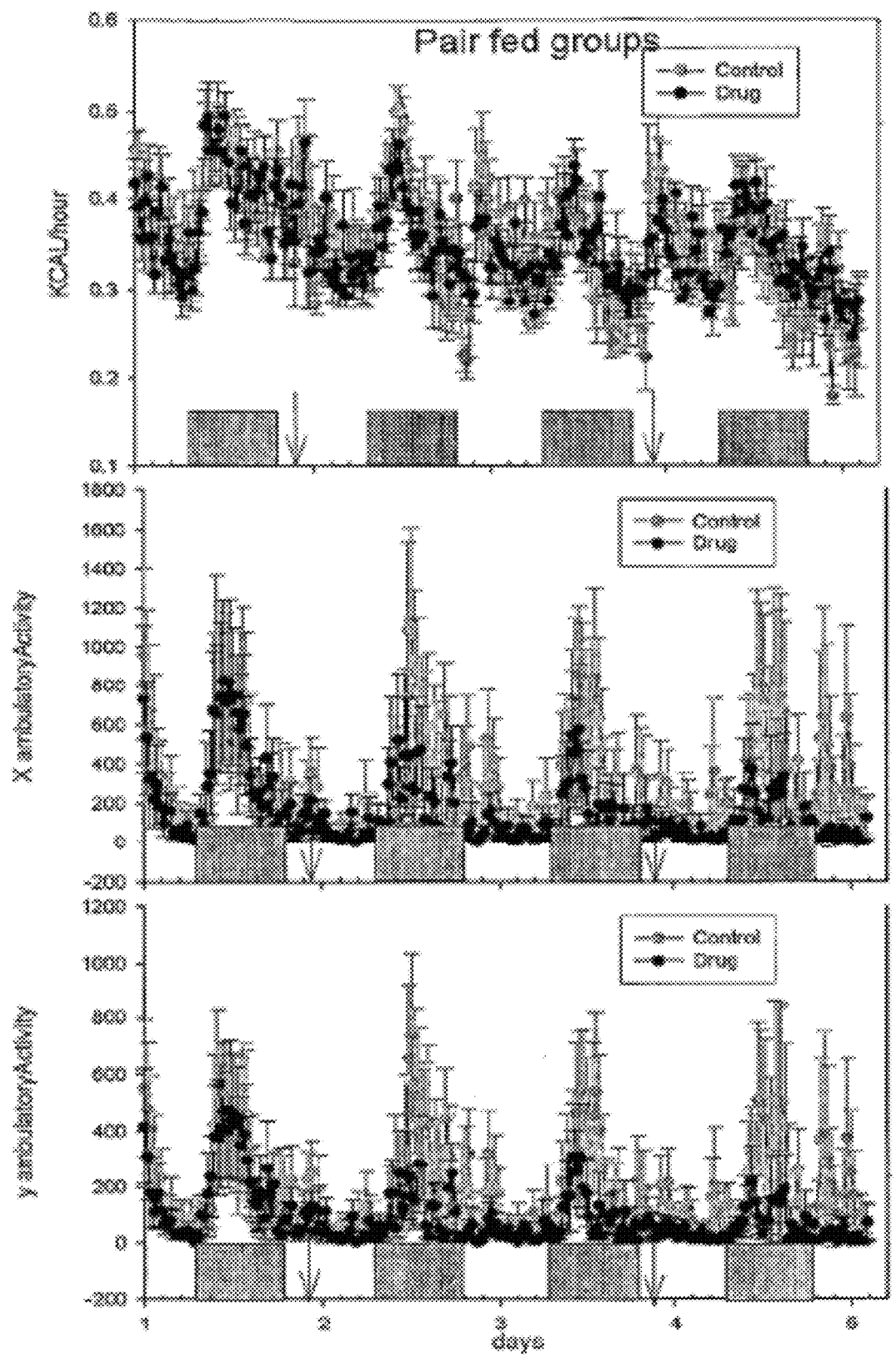
FIG. 27C shows a decrease in energy expenditure and ambulatory activities of both FR1-H7 treated and control animals.
Figure 27D:
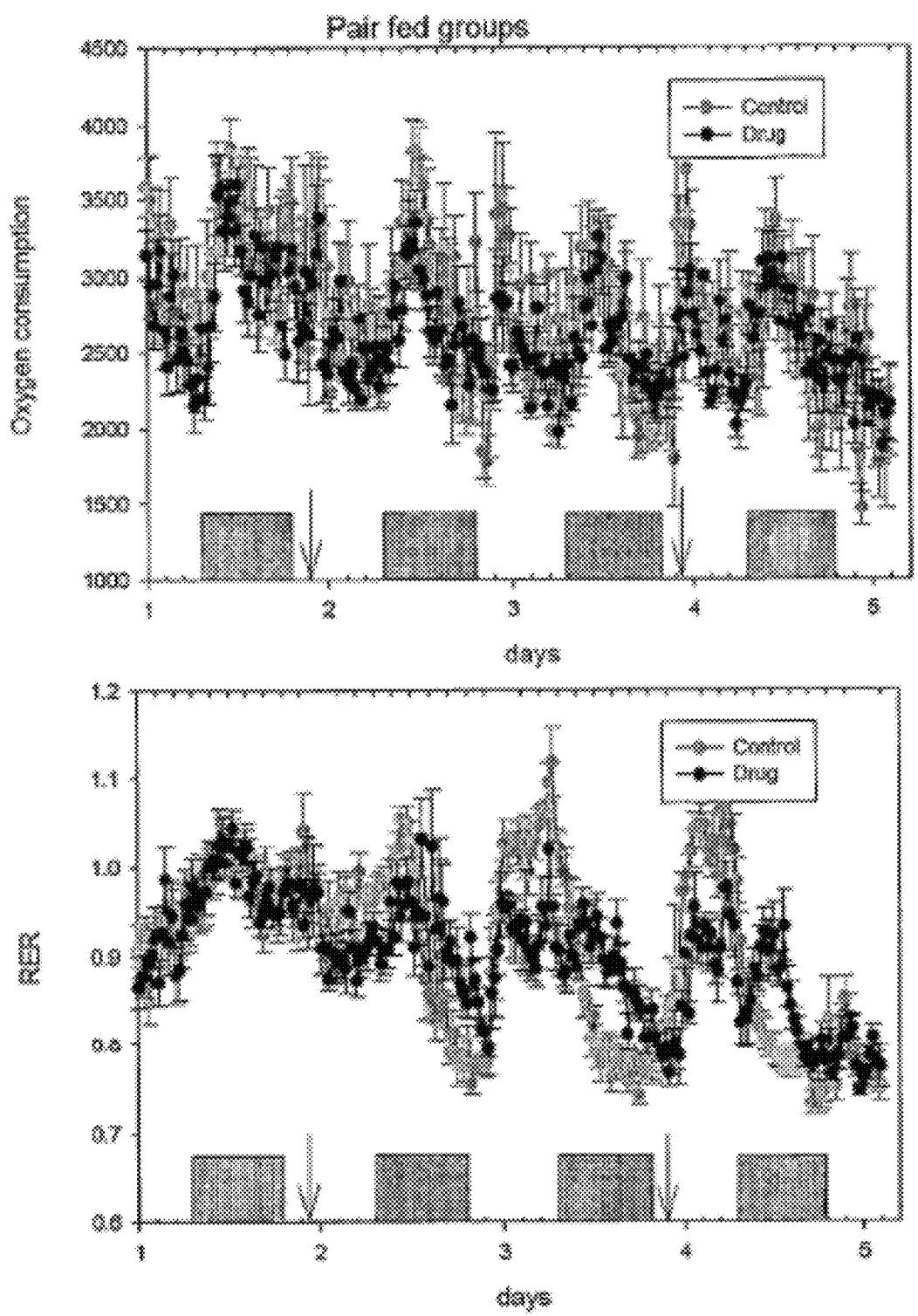
FIG. 27D shows decrease in oxygen consumption of both FR-1-H7 treated and control animals.

The concept of energy homeostasis suggests that weight loss is the result of decreased food consumption, increased energy expenditure, or the combination of both. To elucidate the mechanism of the weight-loss induced by FGFR antagonistic antibodies, the effect of FR1-H7 on energy expenditure and body composition of mice was studied. Mice treated with FR1-H7 exhibited decreases in body weight, food intake, muscle and fat mass, energy expenditure and Respiratory Exchange Ratio (RER) compared to the controls (FIG. 26). A paired-feeding experiment was also conducted which food consumption of control antibody treated animals was restrained to exact that of FR1-H7 treated animals (FIG. 27). Animals from the two treatment groups exhibited identical weight-loss trajectories in a 5-day period. Moreover, body composition (Day 1 and 5) and energy consumption determined for the two groups were mostly indistinguishable. These results suggest that the weight-loss induced by FR1-H7 treatment can be mostly attributed to reduced food intake. Corroboratively, the more prominent decrease in RER values in these animals on later days of the experiment suggests the greater dependence on internal energy source (i.e. lipid metabolism), as to compensate the deficit in food intake.

This study consisted of two stages. In the first stage, female C57 black mice (Charles River Laboratories, Wilmington, Mass.) were randomized into two groups (n=16) and individually housed in a metabolic cage. Both groups of Mice were given hi-carbohydrate content chow and water ad libitum. The two groups of mice were treated with FR1-H7 and control human IgG (10 mg/kg body weight, intraperitoneally), respectively, on Day 2 and Day 4. Body composition was determined using NMR on Day 1 and Day 5. Body weight and food consumption were determined daily. Energy expenditure, ambulatory activities, and oxygen consumption and were monitored continuously. RER were calculated based on energy expenditure and oxygen consumption.

In the second stage, both groups of Mice were given water ad libitum, but only 2 g of hi-carbohydrate content chow each animal per day. The amount of food given was determined in the first stage experiment to be the averaged daily food assumption of those animals one day after being treated with FR1-H7 (10 mg/kg body weight, intraperitonaeally). The two groups of mice were treated and monitored the same way as described in the first stage experiment.

Example 2

Isolation of Monoclonal Antibodies (FR1-H7)

A phage-displayed human Fab library from Dyax Corp. (Cambridge, Mass.) was panned for anti-FGFR-1(IIIb) monoclonal antibody (Fab) clones. Polystyrene Maxi-soap tubes (75×12 mm, Nalge Nunc International, Rochester, N.Y.) were coated with 50 μg of FGFR-1(IIIb) (R&D Systems, Minneapolis, Minn.) overnight, and blocked with 3% milk/PBS at 37° C. for 2 hrs. A mixture of 0.8 ml of phage library (>$10^{13}$ cfu/ml), 200 μl of 2 mg/ml IMC-1C11 (Im-Clone Systems Incorporated, New York, N.Y.), and 200 μl of 18% milk/PBS were added and incubated in the tube at room temperature for 2 hrs. IMC-1C11 antibody served to block the retention of Fab clones that are reactive only to the Fc-tag of the recombinant receptor. The tube was washed 15 times with 0.1% tween-20/PBS (PBST), followed by 15 times with PBS. Bound Fab-phage was eluted by incubating the tube with 1 ml of freshly made 100 mM triethylamine (SIGMA, St Louis, Mo.) at room temperature for 10 min. The eluent was transferred to a 50 ml Falcon tube containing 0.5 ml 1 M Tris-HCl buffer, pH 7.5. Phage was rescued by adding 12.5 ml and 1 ml of fresh *E. coli* TG1 cells ($OD_{600nm}$: 0.5-0.8) to the eluent and panning tube, respectively. *E. coli* cells were incubated at 37° C. without shaking for 30 min, and then with shaking at 100 rpm for an additional 30 min. Infected TG1 cells were combined and grown in 2×YT (Bio 101® systems, Carlsbad, Calif.)/Amp/glucose (2×YTAG) at 30° C. overnight, then harvested and stored at −80° C. for future use.

Phage was grown by culturing 25 ml infected cells in presence of 1 ml M13KO7 helper phage (Invitrogen, Carlsbad, Calif.). The culture was incubated at 37° C. without shaking for 30 mM, and with shaking (225 rpm) for an additional 30 mM. The cell culture was transferred into a 50 ml Falcon® tube (Becton Dickinson, Franklin lakes, NJ), and centrifuged at 1,500×g for 10 min. The cell pellet was then re-suspended in 25 ml of 2×YT/Amp/Kan (2×YTAK) medium, transferred into a fresh 250 ml flask, and grown at 30° C. overnight with shaking (225 rpm). The culture was then transferred into a centrifuge tube and centrifuged at 7,000×g for 10 min. Supernatant was carefully removed to a fresh centrifuge tube, and mixed with PEG/NaCl solution (6:1, v:v). The mixture was incubated on ice for 1 hr, and centrifuged at 20,000×g for 30 mM. Phage pellet was resuspended in 1 ml PBS.

The panning was repeated one more time with tubes coated with 10 µg FGFR-1(IIIb). Single colonies of infected cells were inoculated into 96-well plates containing 100 µl/well of 2×YTAG, and phage was grown in presence of 10 µl M13KO7 helper phage ($5\times10^{10}$ pfu/ml). Plates were incubated at 37° C. for 30 min without shaking followed by 30 min with shaking (100 rpm). Cell pellets were prepared by centrifugation at 2,500 rpm for 10 min, re-suspended in 200 µl of 2×YTAK, and incubated at 30° C. with shaking (100 rpm) for overnight. The plates were then centrifuged at 2,500 rpm for 10 min. Supernatants were transferred in fresh plates and mixed with 6× blocking buffer (18% milk/PBS) for 1 hr. Phage clones were screened in the ELISA blocking assay as described below. Blocking clones was selected and soluble phage was prepared for another round of screening using the ELISA blocking assay. Confirmed blockers were engineered into full size antibodies.

Example 3

Modulation of Serum Levels

Short-term effects of the FR1-H7 antibody on serum levels of insulin, leptin, glucose, and triglycerides were examined by injecting 4 mg/kg antibody or control vehicle into female athymic nude mice. Samples were collected and evaluated before treatment and 6, 24, and 48 hours after treatment. Alanine aminotransferase (ALT), creatine (CPK), blood urea nitrogen (BUN), total serum proteins, and serum albumin levels were measured using serum samples taken 48 hours after treatment. The mice were sacrificed and weights of their left parametrial fat pad, left tibialis anterior muscle, left posterior liver lobe, and spleen were also taken.

Example 4

Modulation of Food Intake

The antibodies weight-reducing effects on other strains of mice, C57 black mice and db/db mice were tested (The Jackson Laboratory, Bar Harbor, Me.). The C57 mice were injected with 0.8 mg/kg, 4 mg/kg, and 40 mg/kg antibody and saline on a Monday, Wednesday, Friday, and following Monday rotation schedule with body weights being measured before each injection and on day 9.

The db/db 7 week old mice were injected subcutaneously with 4 mg/kg antibody on a Monday, Wednesday, and Friday schedule with body weights being measured before each injection and on day 7. Food intake was monitored as well on days 1, 2, 3, 4, and 7. The db/db animals were sacrificed on day 7 and their intrascapular brown fat, epididymal white adipose tissue, and inguinal subcutaneous white adipose tissue were sampled and weighed.

Example 5

In Vitro Activity (FR1-H7)

ELISA and immunoprecipitation was performed using antibody FR1-H7. The Fabs were screened according to their ability to prevent FGF from binding to FGFR-1. The binding specificity of the antibody was examined using an ELISA binding assay, and the results are shown in FIG. 3. FR1-H7 binds FGFR-1(IIIb) and -1(IIIc) with strong affinities, but does not recognize any of the other FGFRs. Results from kinetic analysis indicated the antibody binds to FGFR-1b and -1c equally well. The $K_D$s of the interactions were determined to be approximately 50 pM for both receptors.

Example 6

Inhibition of Ligand-Receptor Binding (FR1-H7)

Figure 4A:
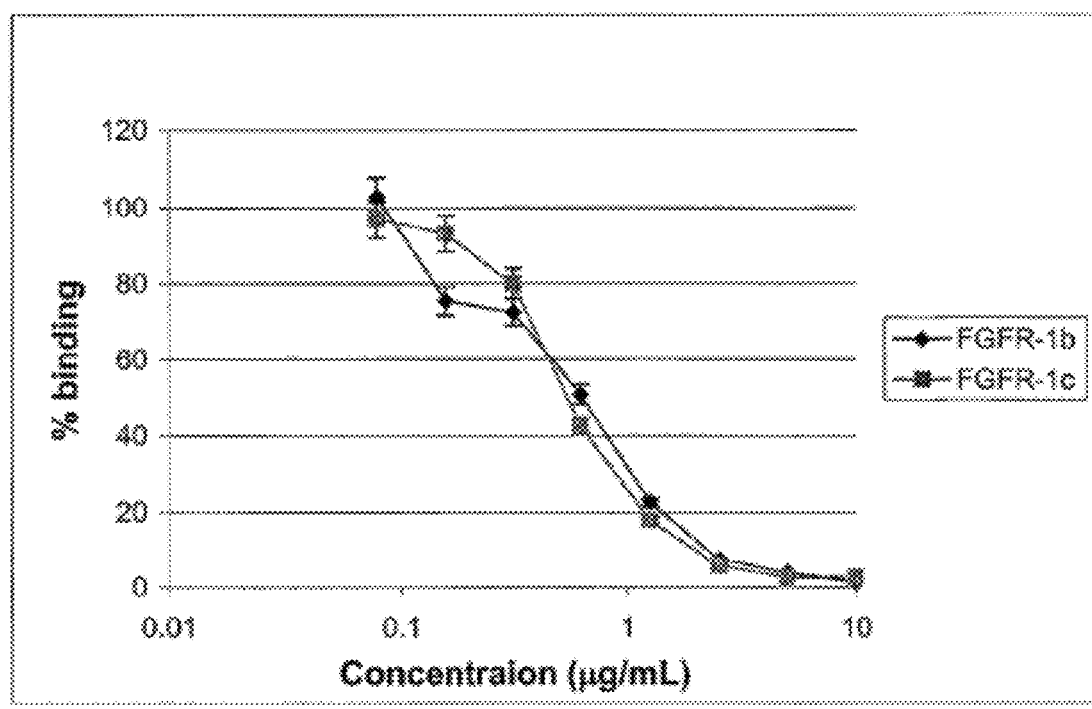
FIG. 4A shows binding to immobilized FGF-1 and FIG. 4B shows binding to immobilized FGF-2. Each data point is an average of duplicates and error bars are standard deviation.
Figure 4B:
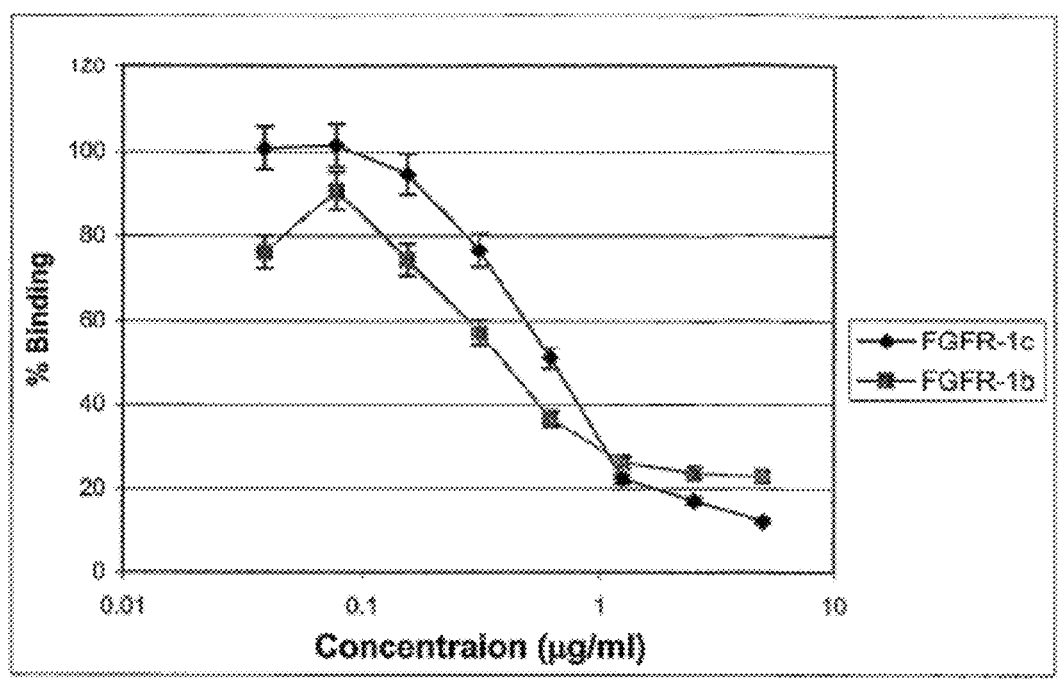
Figure 5A:
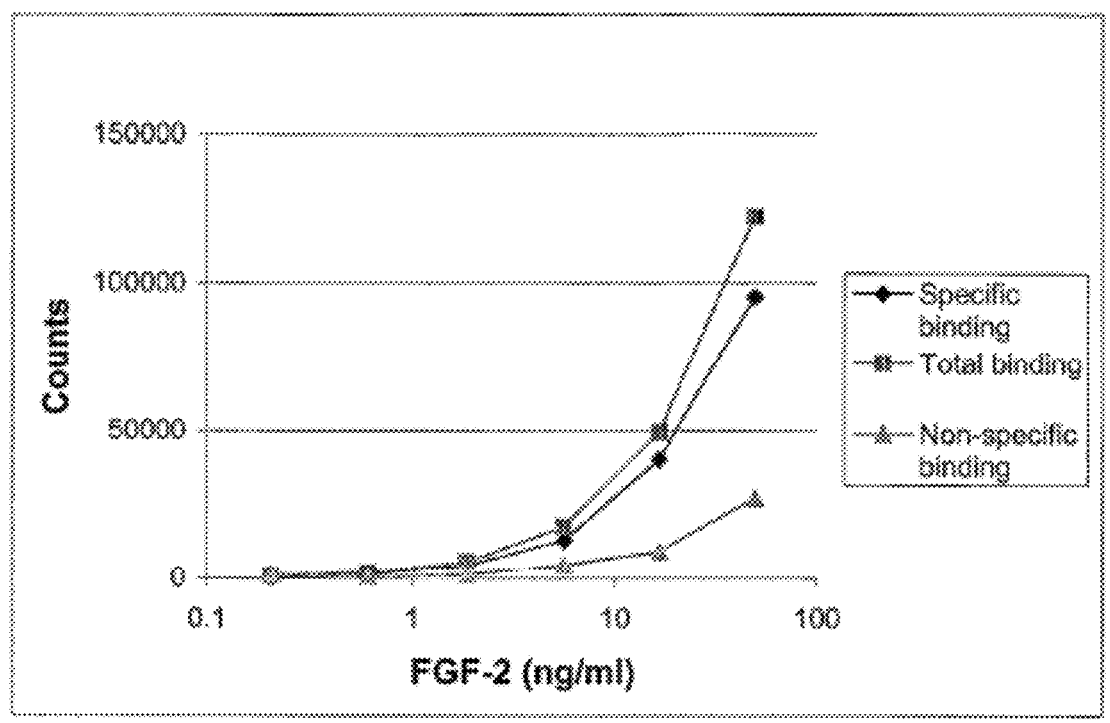
In FIG. 5A, the binding of $^{125}$I-FGF-2 to the cells had two distinct components: non-specific and specific bindings.
Figure 5B:
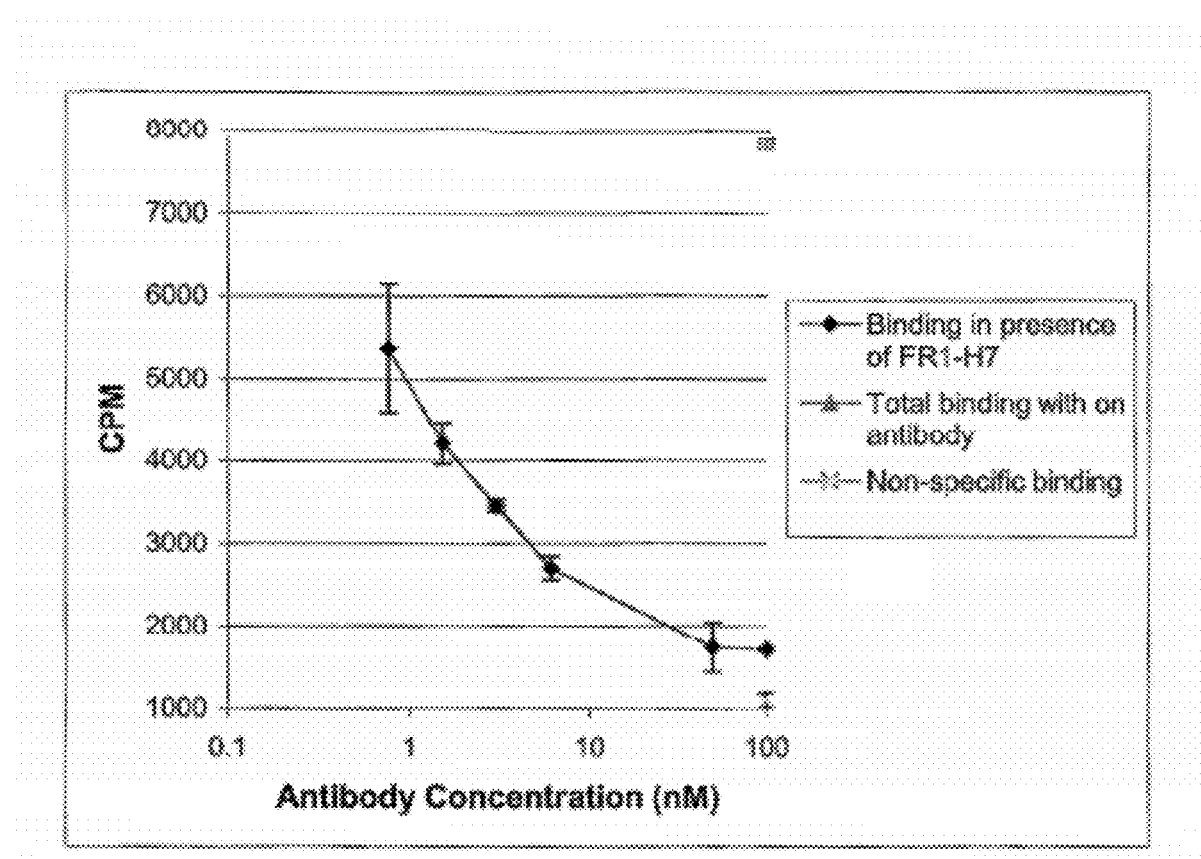
In FIG. 5B, $^{125}$I-FGF-2 binding to the cells was inhibited by the presence of FR1-H7 antibody. Each data point is an average of triplicates. Error bars are standard deviations.

FIGS. 4A & 4B shows the inhibitory effect of FR1-H7 on ligand-receptor binding as determined in an ELISA blocking assay. Two FGFR1-binding ligands, FGF-1 (FIG. 4A) and FGF-2 (FIG. 4B) were tested in the blocking assay. FR1-H7 was found to block recombinant FGFR-1(IIIb) and -1(IIIc) equally well in their binding to FGF-1, with $IC_{50}$s of approximately 5 nM. The antibody also blocks the receptors from binding to FGF-2, with $IC_{50}$s in the range of 2-5 nM, although it is slightly more potent in inhibiting FGFR-1(IIIb) than -1(IIIc). The blocking activities to fully active, native FGFR-1 receptor were determined in the cell-based blocking assay. As shown in FIG. 5A, the total binding of FGF-2 to FGFR-1-expressing cells has two components: non-specific binding, and specific binding. The latter accounts for the majority of the total binding. FIG. 5B shows that FR1-H7 inhibits the specific binding of $^{125}$I-FGF-2 to the cells, and the blocking is near completion at the concentration of 200 nM. The $IC_{50}$ is lower than 5 nM by estimation.

Example 7

Ligand Mediated FGFR-1 Signaling, Cell Growth In Vitro (FR1-H7)

Under normal condition, the activation of FGFRs is ligand-dependent. The blocking of ligand binding by FR1-H7 consequently leads to inhibition of auto-phosphorylation of the receptor. This is demonstrated in FIG. 6, in which the western blot was probed with anti-phospho-tyrosine antibody for activated receptor—the upper blot was probed with anti-phospho-tyrosine antibody and the lower blot showed control protein bands in the cell lysates for estimation of relative gel loading. The results show that the FR1-H7 by itself does not activate the receptor, and significantly inhibits FGF-2 mediated receptor phosphorylation.

Figure 7:
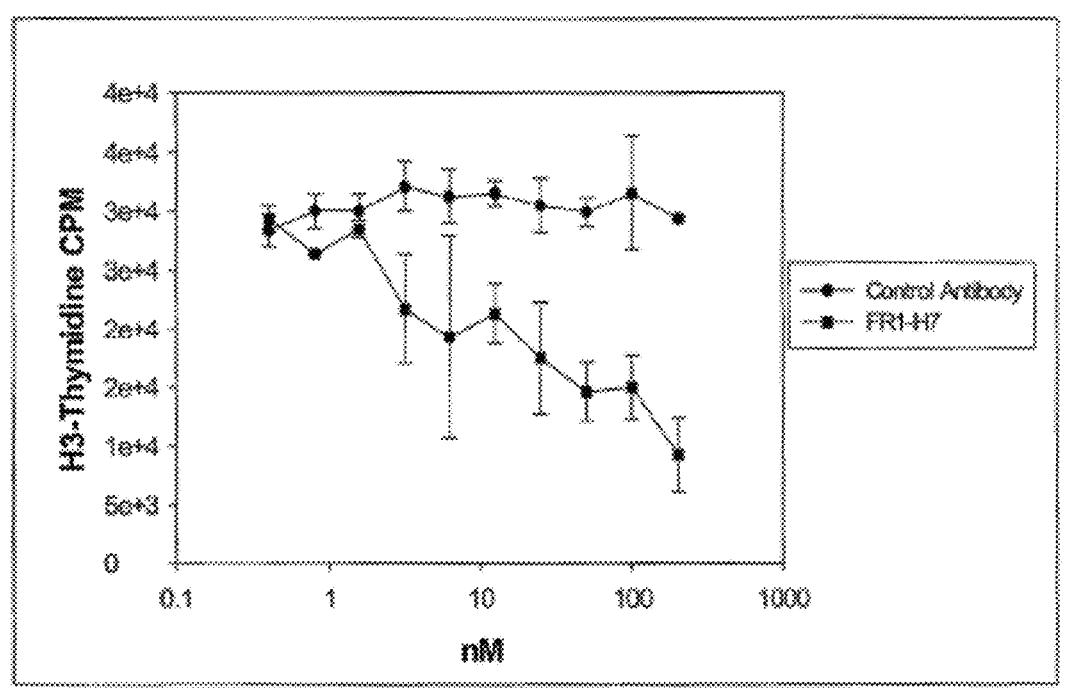
FIG. 7 shows proliferation of Human Umbilical Vascular Endothelial Cells (HUVECs) in vitro in presence of antibodies. Each data point is an average of triplicates and error bars are standard deviation.

HUVEC is known to express FGFR-1(IIIb) on the cell surface (Ferning and Gallagher, 1994). FGFs have been shown to stimulate the growth of endothelial cells strongly, and thus are considered major pro-angiogenic factors. FIG. 7 shows that FR1-H7 inhibited the proliferation of HUVECs in vitro in a dose-dependant manner. These results demonstrate that FR1-H7 may be used as an anti-angiogenic therapeutic in certain diseases.

Figure 8A:
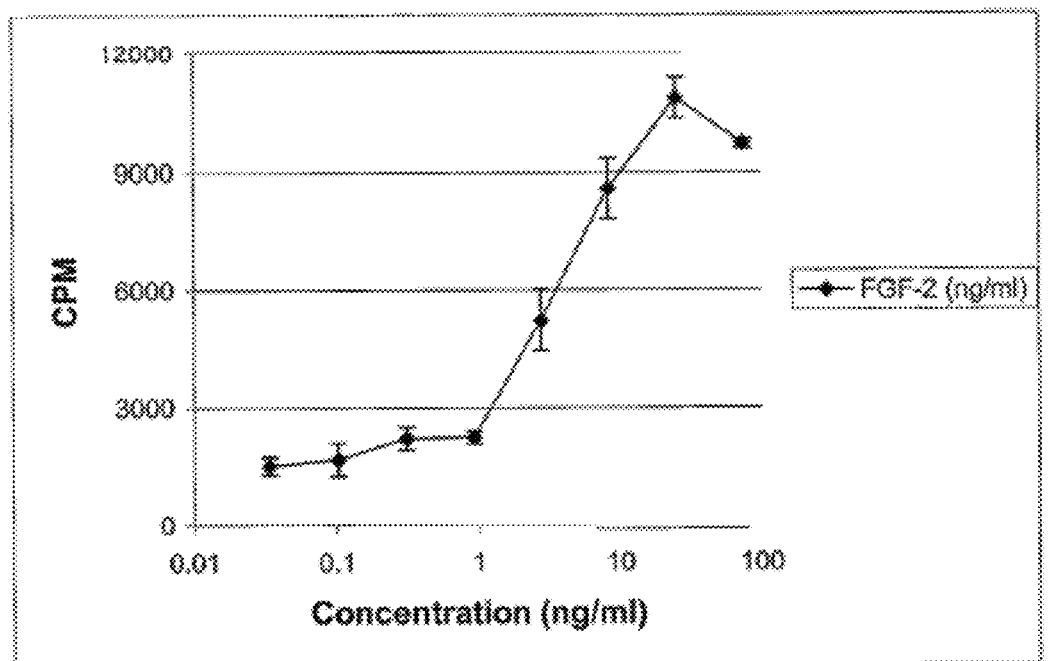
FIG. 8A shows the effects of FGF-2 on adipocyte proliferation and FIG. 8B shows the effects of FR1-H7 on FGF-2-stimulated adipocyte proliferation. Each data point is an average of triplicates. Error bars are standard deviations.
Figure 8B:
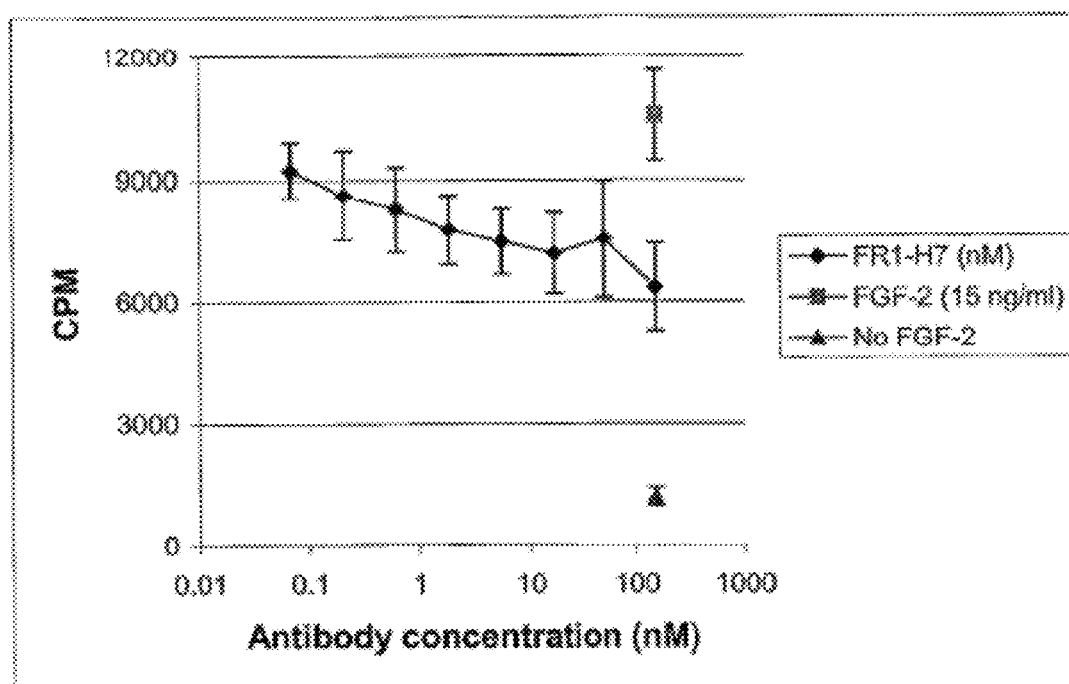

The effects of the FGF pathway on the proliferation of Adipocytes in vitro are shown in FIG. 8. FGF-2 had a profound stimulating effect on the growth of the adipocytes. The level of thymidine incorporation was capable of a 10-fold increase in presence of FGF-2 (FIG. 8A). FR1-H7 inhibited the FGF-2-stimulated proliferation of adipocytes in a dose dependant manner (FIG. 8B).

Example 8

Antibody Activity (FR1-H7)

Figure 9:
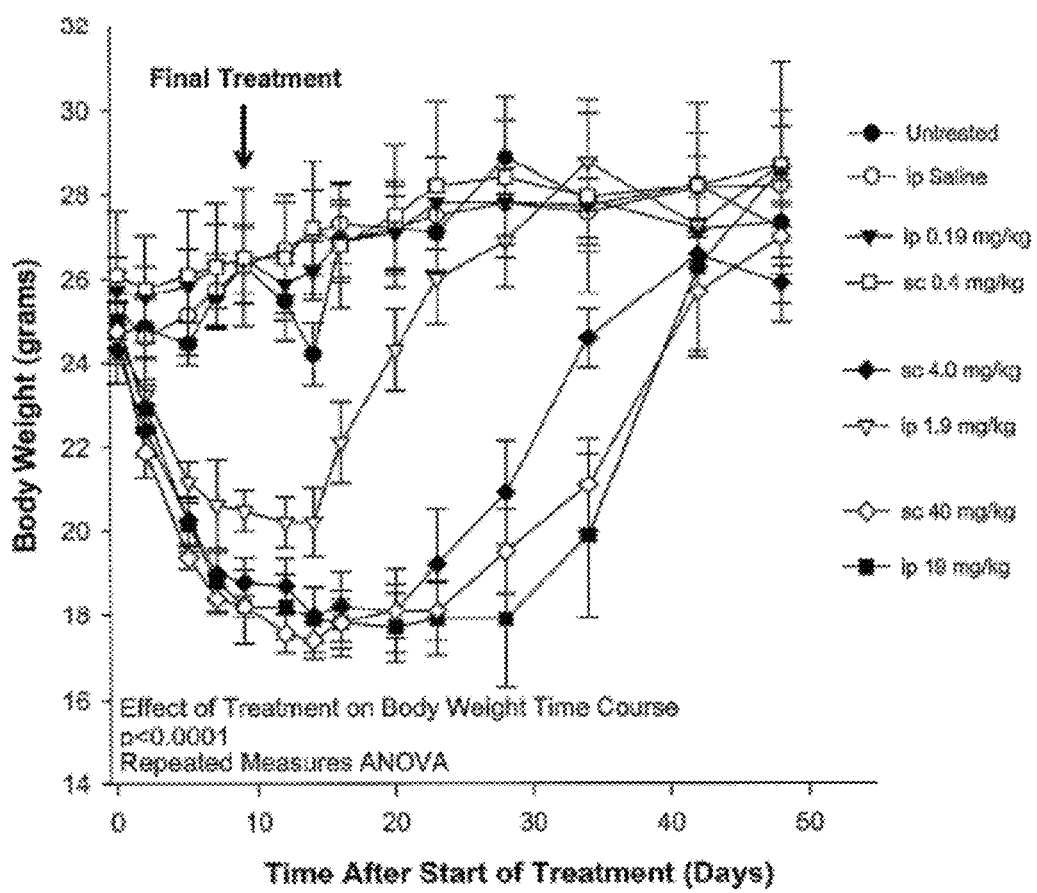
FIG. 9 shows the effect of FR1-H7 on body weight in nu/nu female mice (Mean+/−SEM).

FR1-H7 induces reversible weight loss in a dose-dependent manner. Both s.c. and i.p. administration of FR1-H7 caused dose-dependent weight loss of the animals (FIG. 9).

At the two lowest dosages, 0.19 and 0.4 mg/kg, mice had slight weight gains that are identical as the untreated or vehicle treated animals. At 1.9 mg/kg dosage, steep weight loss of ~20% of the total body weight occurred within the first 3 treatments, and then the weights of the animals showed a trend of stabilization. Moderate weight loss (~0.5 g) continued one week after the treatment was stopped. This was followed by rapid recovery of the weights. Complete recovery was reached 25 days after treatment was stopped, and the averaged weight of this group was identical to that of the controls. At dosage higher than 4 mg/kg, the antibody inflicted the same degree of weight loss independent of the doses. Rapid weight loss occurred within the first 3 treatments, followed by a gradual stabilization of the weights. The maximal weight loss amounts to ~1/3 of the averaged body weight of the controls. Weight recovery after the stop of the treatments seemed to be dose-dependent. Lagging times of the first significant weight gains after the stop of the treatments were 14 days, 19 days, and 24 days, for antibody treatment of 4 mg/kg s.c., 40 mg/kg s.c., and 19 mg/kg i.p., respectively. Except that one animal in the 19 mg/kg group was euthanized due to unusual weight loss of ~50% of the total body weight, all mice in the antibody treated groups eventually recovered their weights completely.

Example 9

Food Intake and Exploratory Behavior

Figure 10:
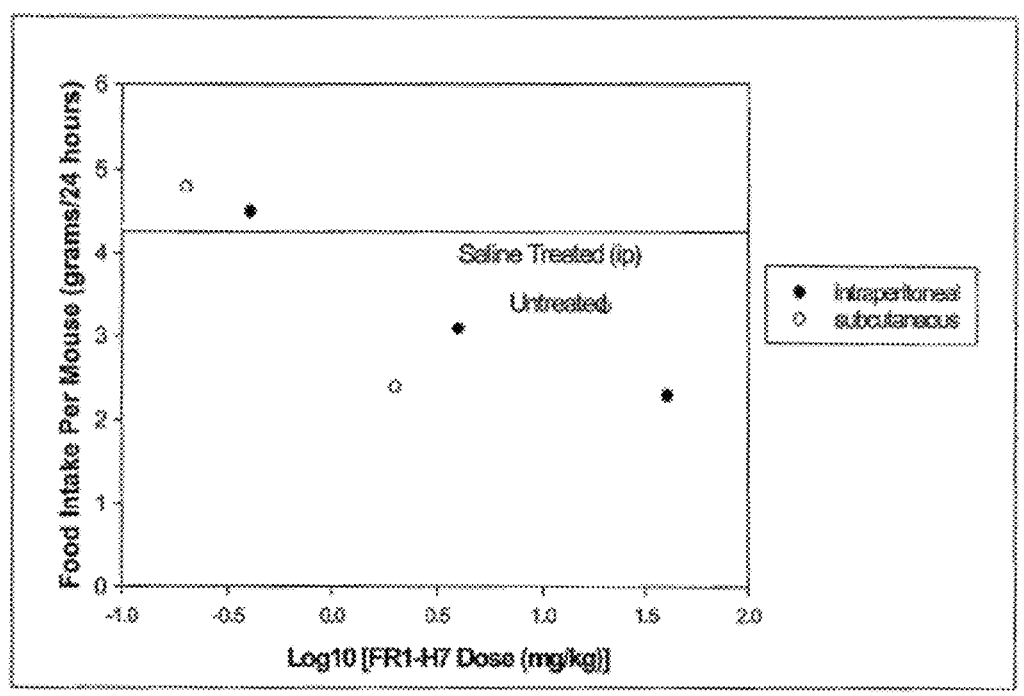
FIG. 10 shows the effect of FR1-H7 on food intake in nu/nu female mice.
Figure 11:
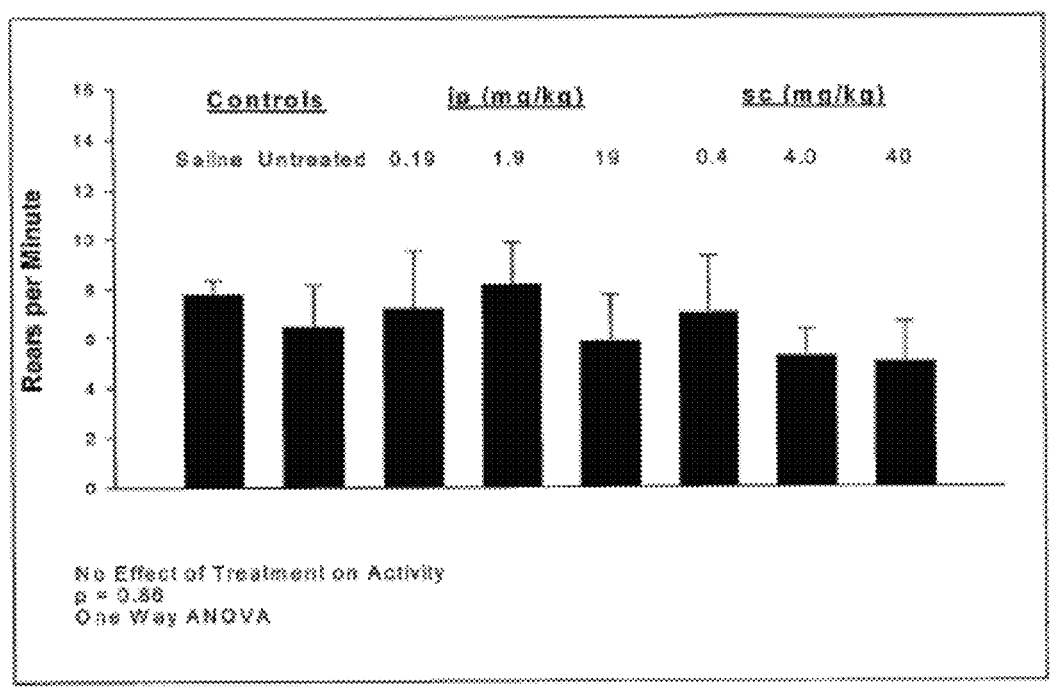
FIG. 11 shows the effect of FR1-H7 on rearing behavior in a novel environment (Mean+/−SEM).

Non-fasting food intake, measured over the period between the second and third treatment, was reduced by approximately 35% in groups of mice that lost weight, but not in the low dosage groups in which weight loss did not occur (FIG. 10—Effect of FR1-H7 on food intake in nu/nu female mice). The exploratory behavior of mice, measured as the number of rearings per min in a novel environment, was not significantly altered by the antibody treatments (FIG. 11—Effect of FR1-H7 on rearing behavior in a novel environment; Mean+/−SEM). This is in agreement with the general observation that mice were not moribund, in spite of dramatic weight loss.

Example 10

Modulation of Glucose Levels

Figure 12A:
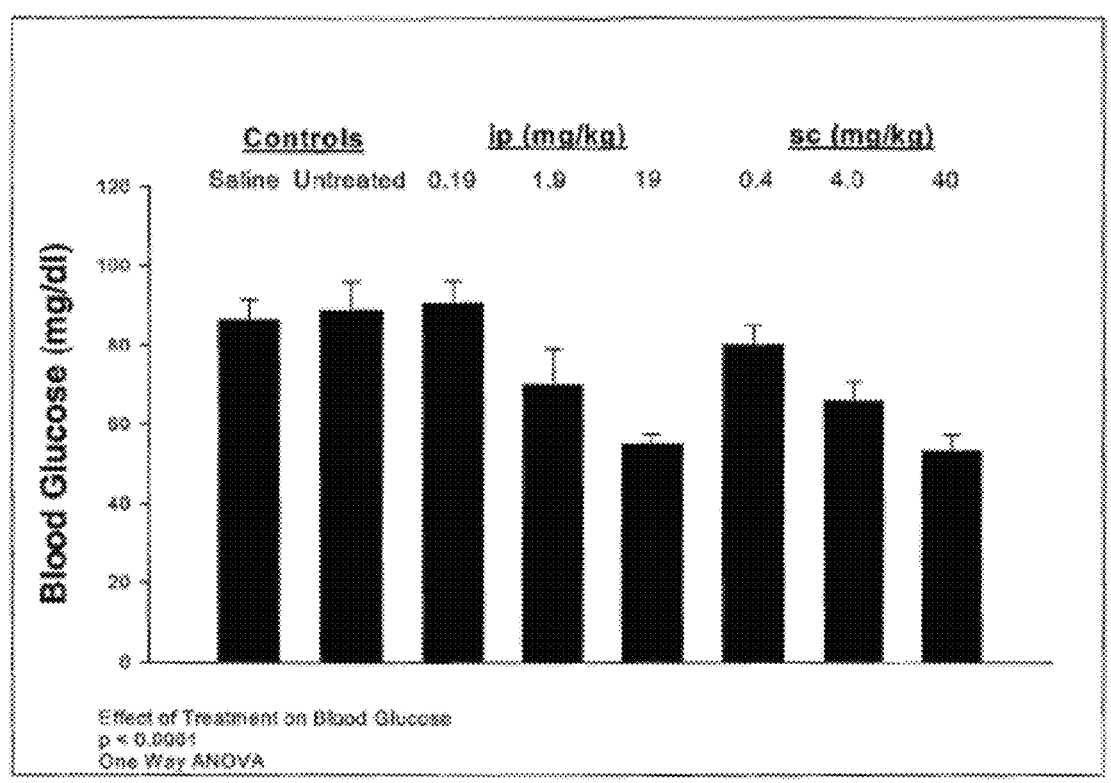
FIG. 12A shows the effect offal-H7 on non-fasted blood glucose (Mean+/−SEM).
Figure 12B:
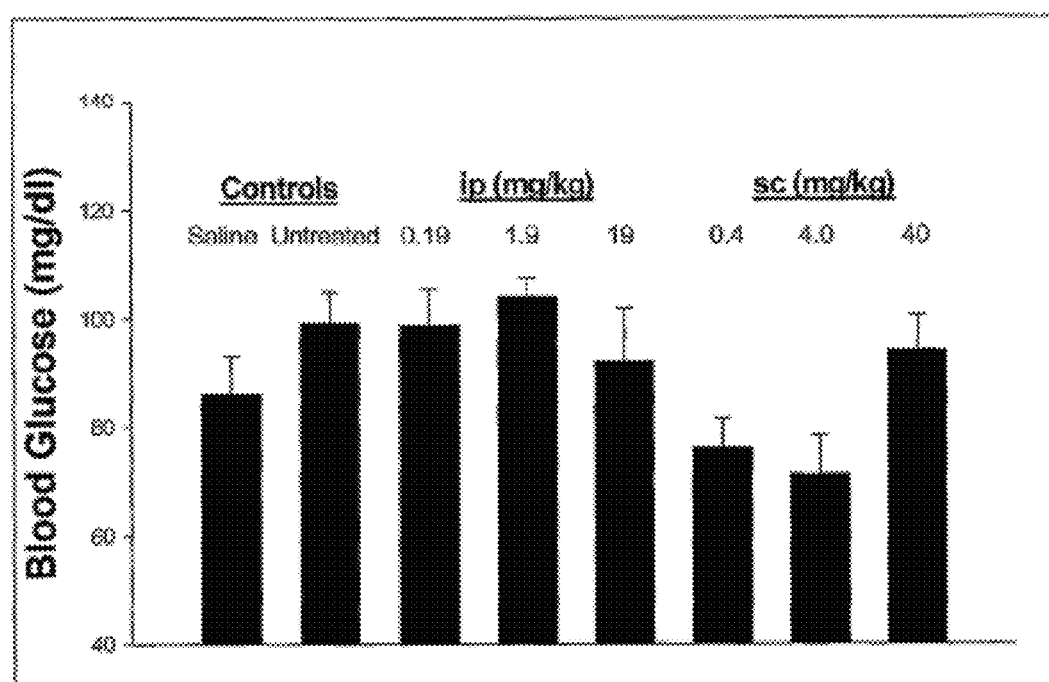
FIG. 12B shows the effect of FR1-H7 on non-fasted blood glucose after weights are fully recovered (Mean+/−SEM).

Non-fasting blood glucose level was determined one week after the end of the antibody treatment. It appeared that the antibody reduced the blood glucose in a dose-dependent manner (FIG. 12A—Effect of FR1-H7 on non-fasted blood glucose; Mean+/−SEM). The greatest reduction occurred in 19 mg/kg i.p. and 40 mg/kg s.c. groups, which amounted to ~1/3 of the normal glucose level. On day 64, 52 days after the final treatment, non-fasted blood glucose was again measured. However, serum glucose levels were restored to normal range by day 64 after the animals fully recovered their body weights (FIG. 12B—Effect of FR1-H7 on non-fasted blood glucose after weights are fully recovered; Mean+/−SEM).

Example 11

Reduction in Adipose Tissue, Serum Triglycerides, Insulin, and Leptin

Figure 13:
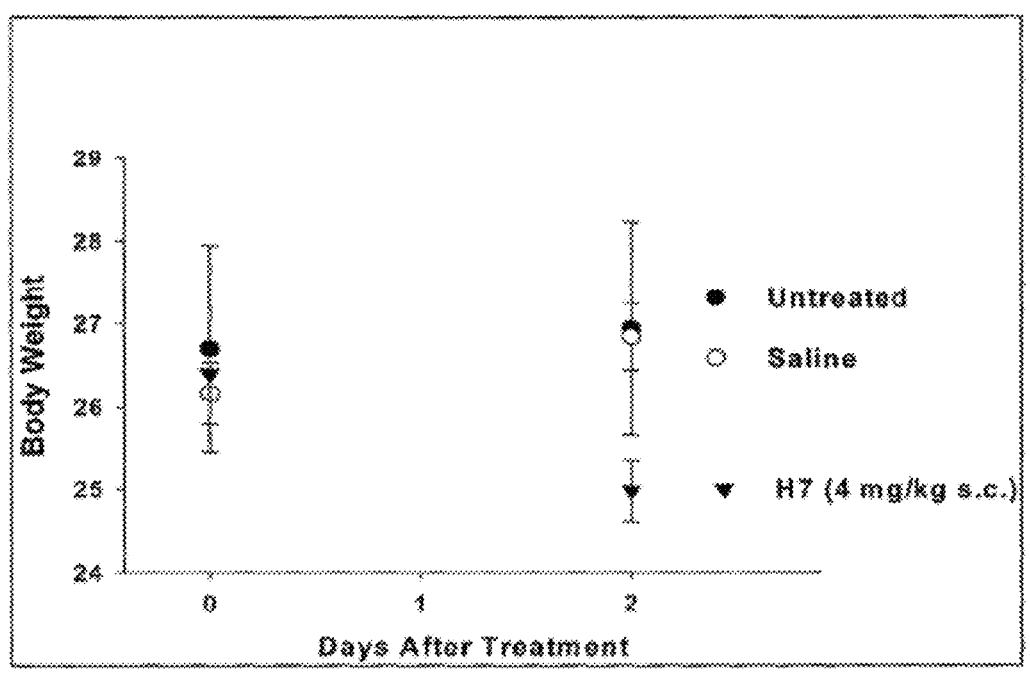
FIG. 13 shows body weight loss in nu/nu mice after a single does of FR1-H7 treatment (Mean+/−SEM, n=4).
Figure 14:
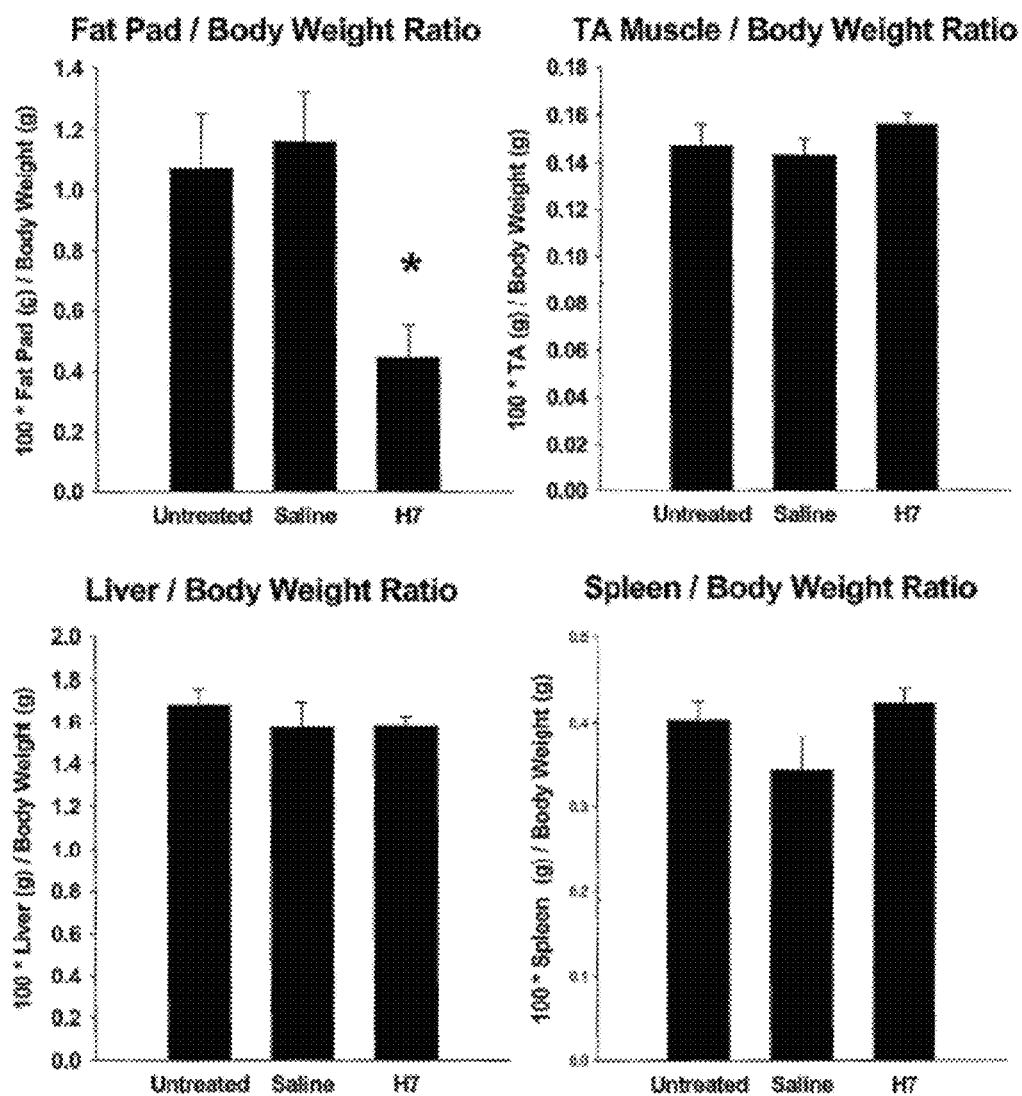
FIG. 14 shows the effects on tissue weights after a single does of FR1-H7 treatment. Each bar represents the value calculated as 100× the ratio of tissue weight over total body weight. Error bars are standard deviation.
Figure 15A:
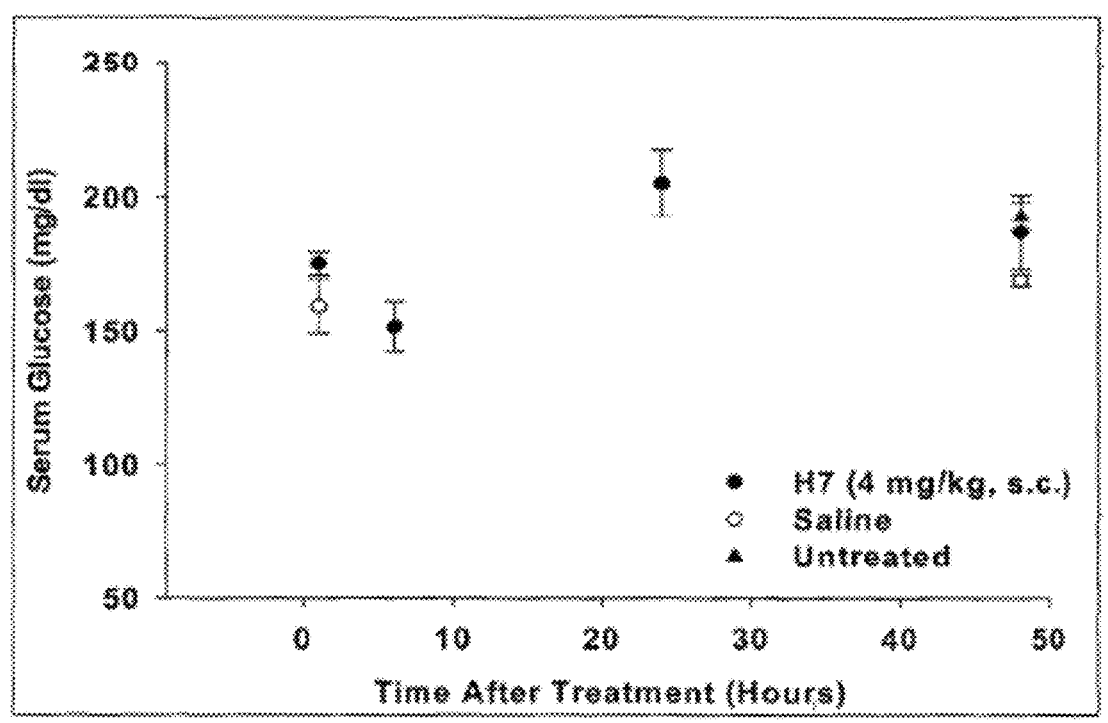
In FIG. 15A, serum glucose levels (mean+/−SEM) are determined.
Figure 15B:
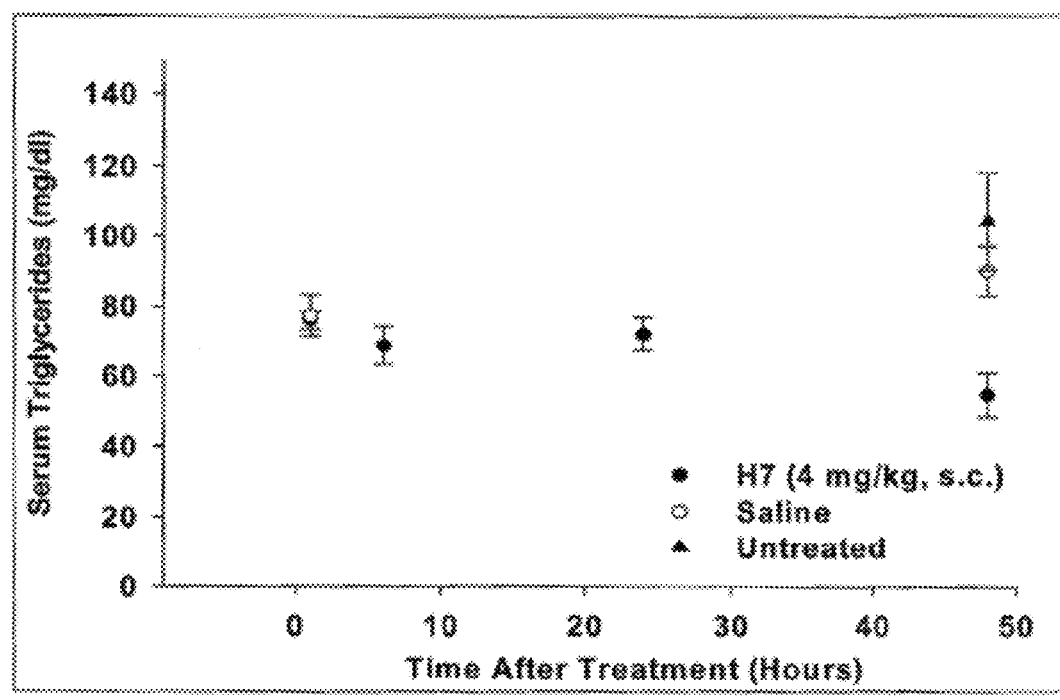
in FIG. 15B, serum triglycerides levels (mean+/−SEM) are determined.
Figure 15D:
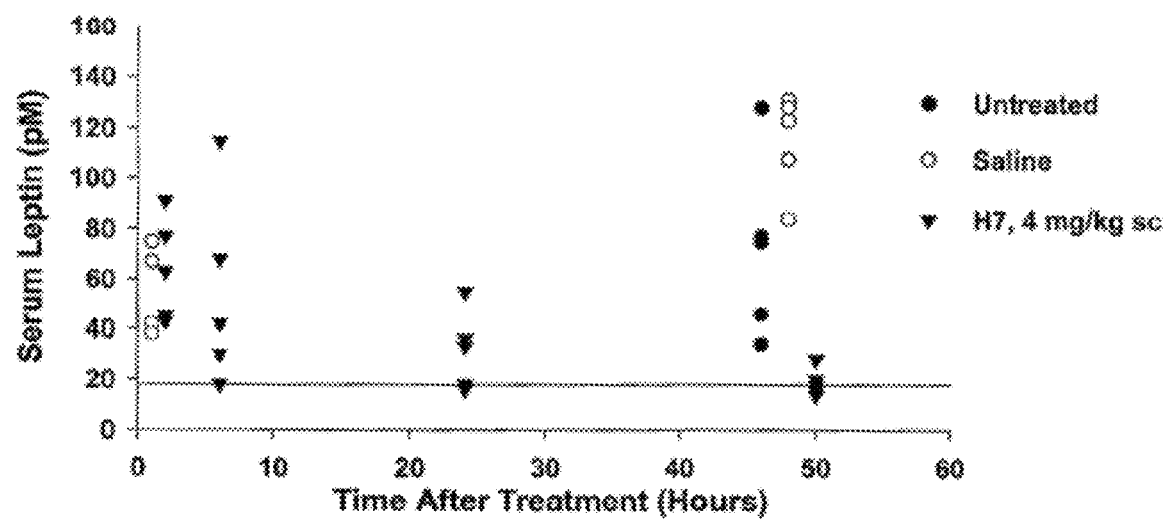
FIG. 15 shows the effects on serum chemistry after a single dosing of FR1-H7 treatment.
in FIG. 15C, serum insulin levels are determined; and in FIG. 15D, serum leptin levels are determined. All individual measurements are shown. Data taken at the same time points were separated according to treatment groups for viewing purpose.

To study the short-term effect of FR1-H7, nude mice were treated with a single injection of 4 mg/kg FR1-H7 s.c., and monitored the effects 48 hours after. FIG. 13, which is a graph of body weight loss in nu/nu mice after a single does of FR1-H7 treatment (Mean+/−SEM, n=4), showed that the antibody treatment caused significant body weight reduction within 48 hours. The averaged weight in the antibody-treated group was reduced by approximately 6% compared to that of the control groups. To investigate the source of this reduction, the weight measurement of representative tissue samples was taken. As shown in FIG. 14 (effects on tissue weights after a single does of FR1-H7 treatment; each bar represents the value calculated as 100× the ratio of tissue weight over total body weight; error bars are standard deviation) weight reduction of approximately 60% was observed in parametrial fat pad, while the weights of muscle, liver, and spleen appear to be normal.

FIG. 15A-D show that FR1-H7 did not affect the serum glucose level 48 hours after the treatment. However, serum triglycerides, insulin, and leptin levels were significantly reduced, indicating that FR1-H7 systematically affected the energy metabolism of the animals. There were no significant differences in the levels of ALT, CPK, BUN, total serum proteins, and serum albumin between the antibody-treated and control groups, suggesting normal liver, muscle and kidney function in the treated animals.

Example 12

Induction of Weight Loss

Figure 16:
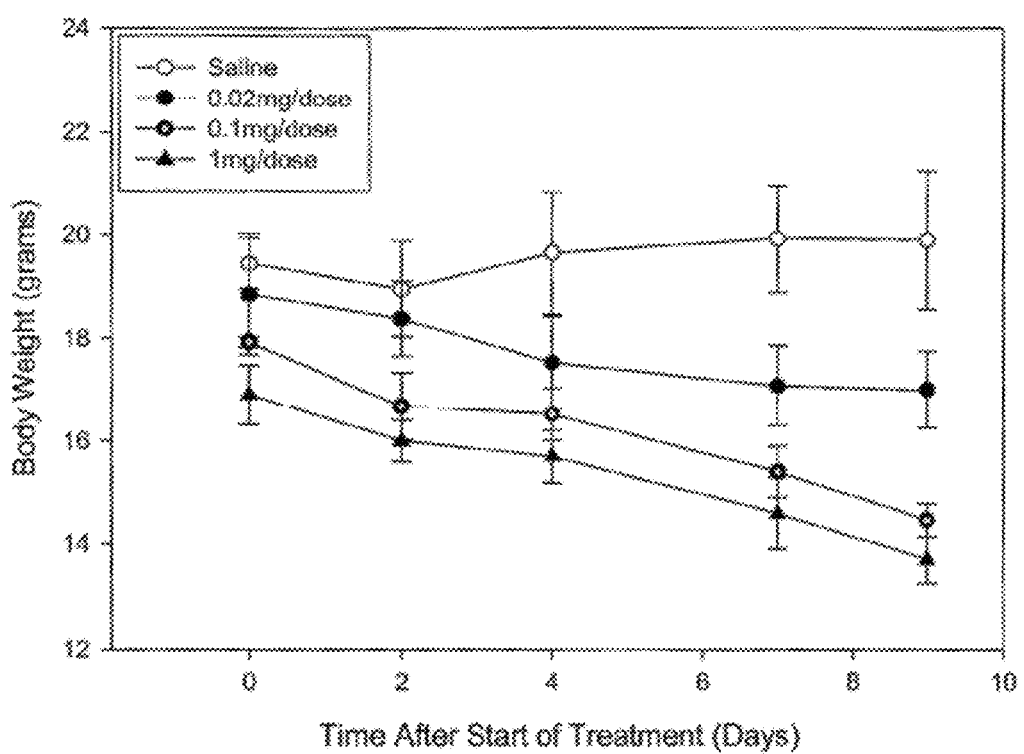
FIG. 16 shows the effect of FR1-H7 on body weight in C57 black mice (Mean+/−SEM).
Figure 17:
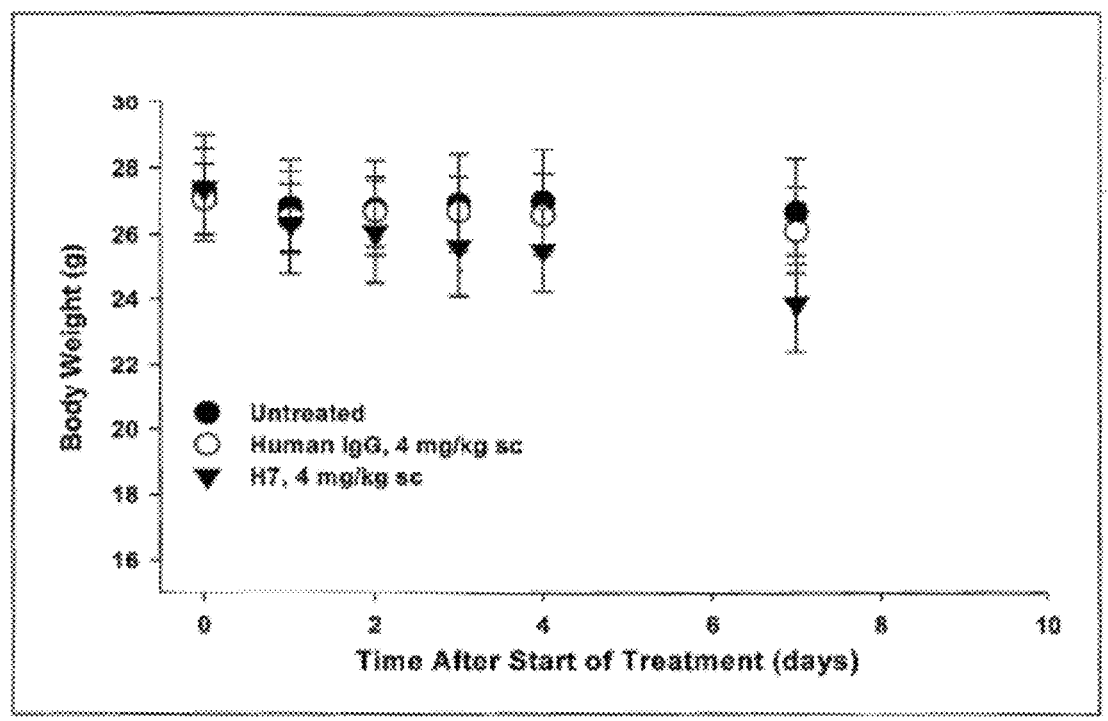
FIG. 17 shows the effect of FR1-H7 on body weight in db/db mice (Mean+/−SEM).
Figure 18:
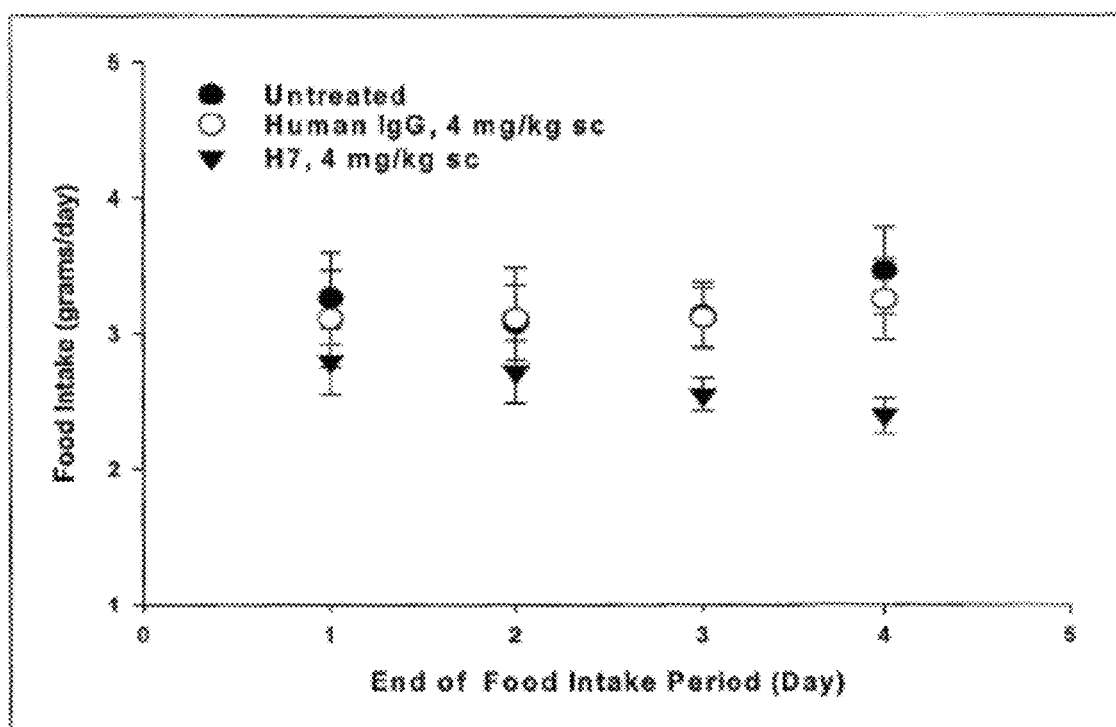
FIG. 18 shows the effects of FR1-H7 on food intakes in db/db mice (Mean+/−SEM).
Figure 19:
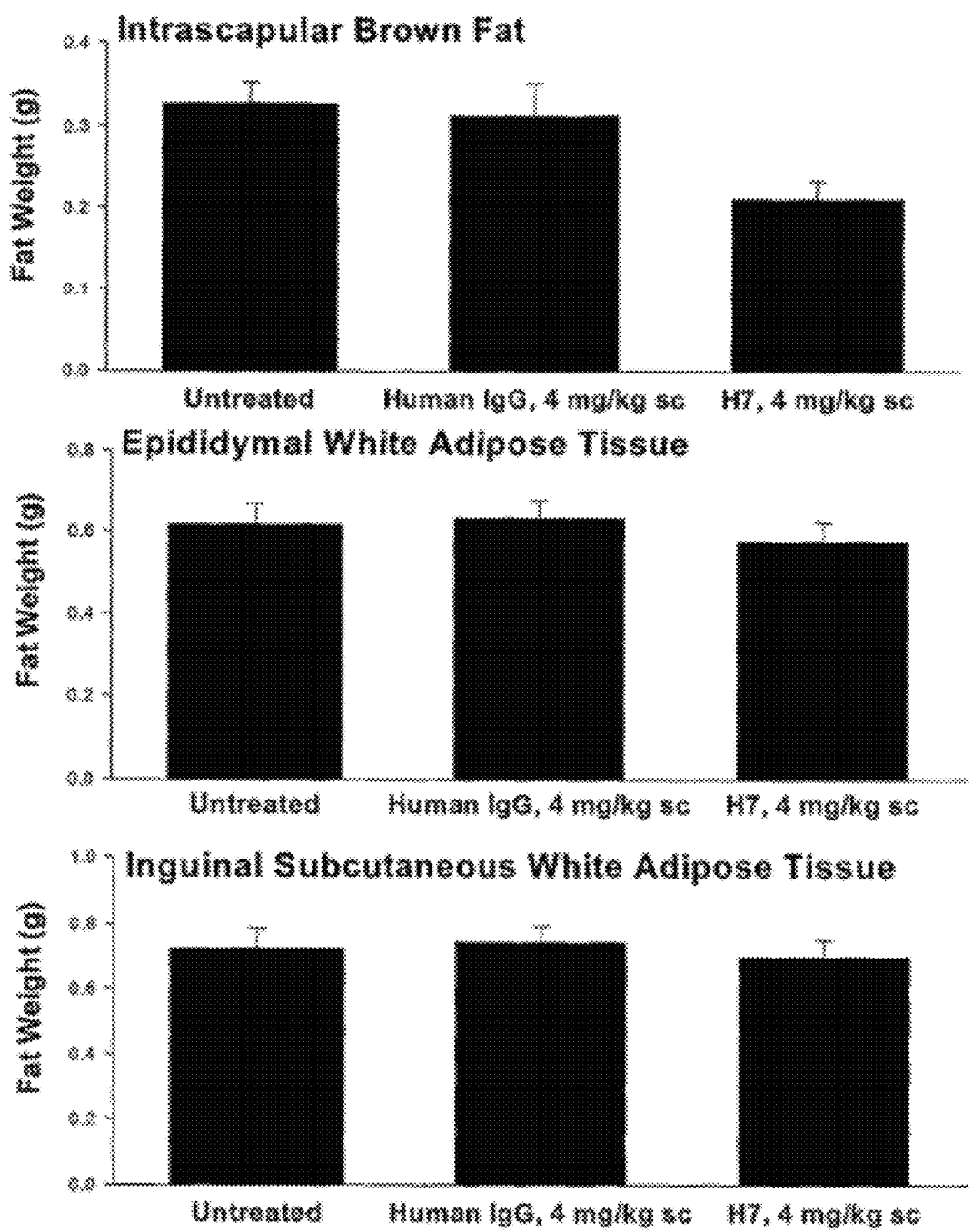
FIG. 19 shows the effects of FR1-H7 on the sizes of adipose tissue (Mean+/−SEM).

FIG. 16 shows that FR1-H7 treatment caused dose-dependent weight loss of C57 black mice, though the effect is less dramatic than in the nude mice. After 4 treatments, the weight reduction compared to the starting weights were approximately 5%, 16% and 16% for 0.8 mg/kg, 4 mg/kg and 40 mg/kg treated groups, respectively. In db/db mice, weight reduction is even more moderate compared to that in the nude mice (FIG. 17). In the 7-day period, weight reduction occurred gradually, and reached approximately 10% of the total body weight on Day 7. This was accompanied by a gradual reduction in food intakes (FIG. 18). Analysis of different adipose tissues showed that significant reduction occurred in intrascapular brown fat tissue, while the weights of epididymal white adipose tissue and inguinal subcutaneous white adipose tissue changed little (FIG. 19). The more moderate weight loss caused by FR1-H7 db/db mice may be attributed to the leptin pathway deficiency, or simply due to the abundance of fat tissues in these animals.

Example 13

Isolation of Antibody (FR1-A1)

Using the method described in Example 2, with the exception that the Phage-displayed human Fab library from Dyax was panned for anti-FGFR-1(IIIc) Fab clones, an antibody specific for anti-FGFR-1(IIIc) was identified. The identified antibody was designated FR1-A1.

Example 14

In Vitro Activity (FR1-A1)

Figure 20:
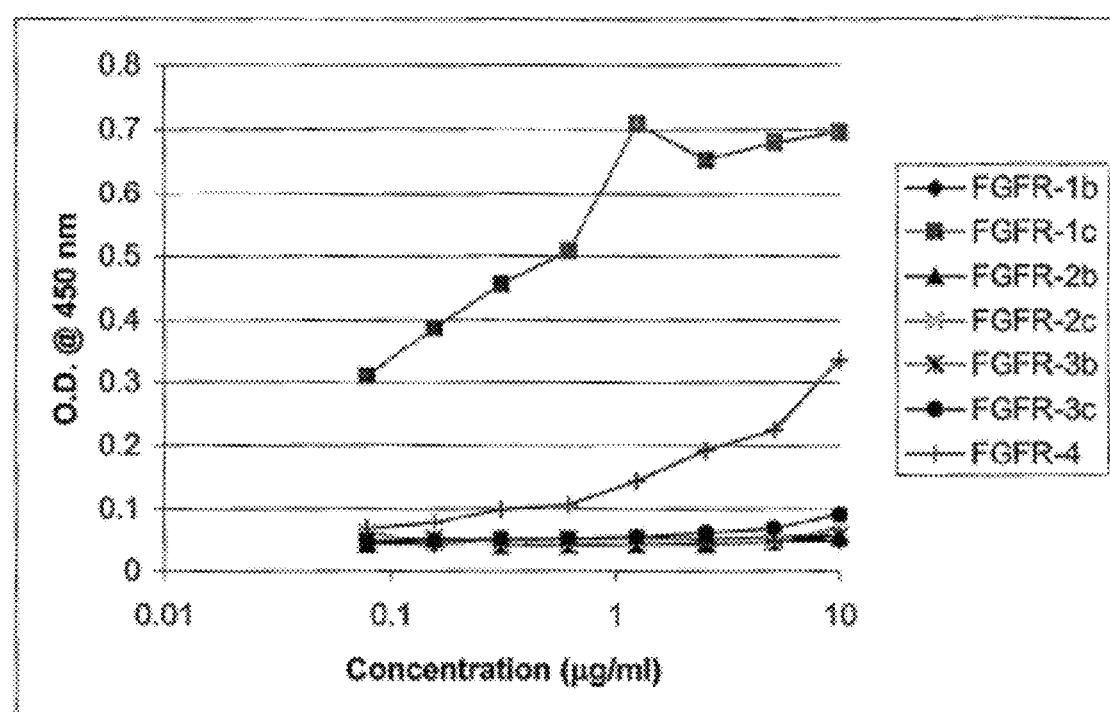
FIG. 20 shows the binding of FR1-A1 antibody to FGFRs as determined using the ELISA binding assay.
Figure 21:
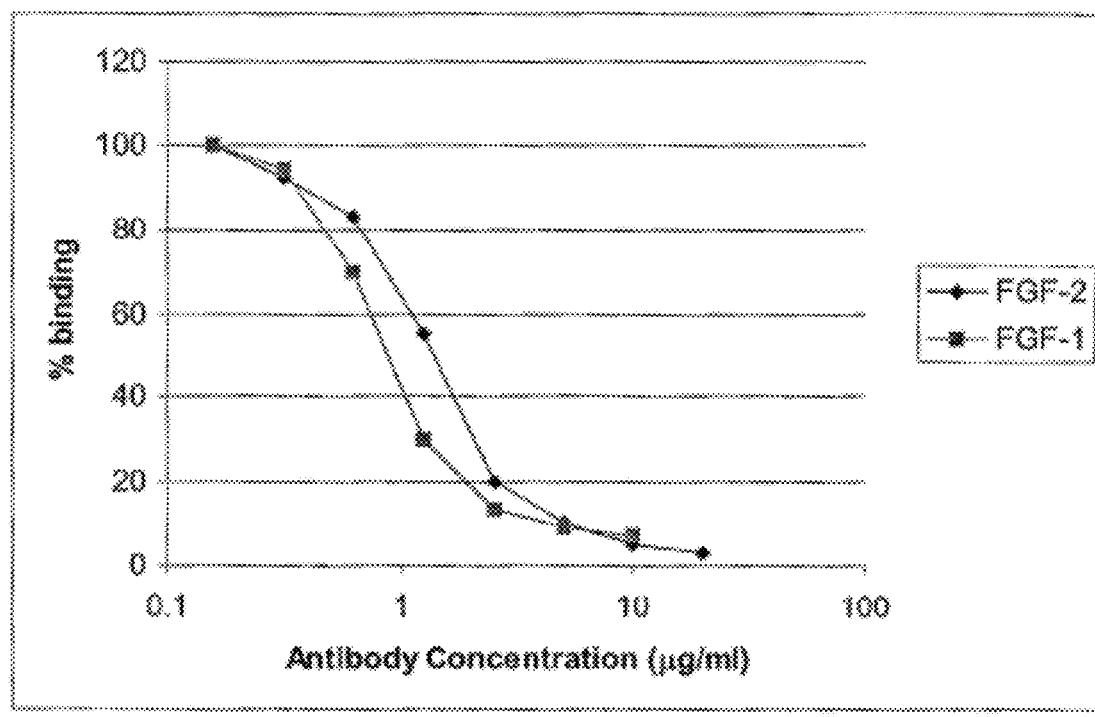
FIG. 21 shows binding of recombinant FGFR-1 to FGF ligand as determined using the ELISA blocking assay.

FR1-A1 exhibits strong binding affinity to FGFR-1(IIIc), and moderate affinity to FGFR-4. It shows little binding to all the other receptors (FIG. 20). The $K_D$s towards these receptors as determined from kinetic analyses are as follows:
FGFR-1b: >10 μM
FGFR-1c: 0.7 nM FGFR-2b: >10 μM
FGFR-2c: >10 μM
FGFR-3b: >10 μM
FGFR-3c: >10 μM
FGFR-4: 90 nM FIG. 21 shows the inhibitory effects of FR1-A1 on ligand-receptor binding as determined in an ELISA blocking assay. Two FGFR-1(IIIc) binding ligands, FGF-1 and FGF-2 were tested in the blocking assay. FR1-A1 blocked the binding of FGFR-1(IIIc) to FGF-1 and FGF-2 with $IC_{50}$s of approximately 5 and 10 nM, respectively.

Example 15

Inhibition of Ligand-Mediated FGFR-1(IIIc) Signaling, and Cell Growth In Vitro (FR1-A1)

Figure 22:
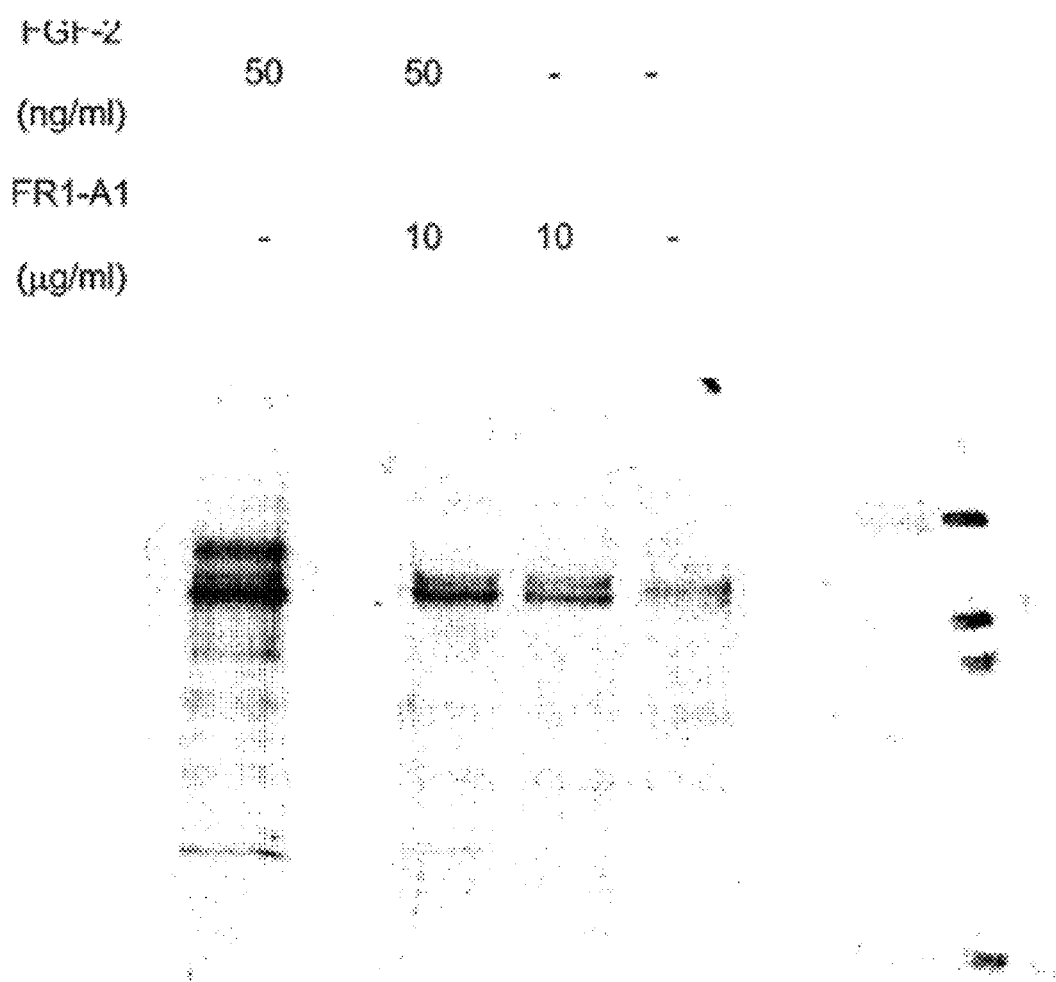
FIG. 22 shows a Western blot of FGFR-1 phosphorylation.

The blocking of ligand binding by FR1-A1 consequently leads to inhibition of auto-phosphorylation of the receptor. This is demonstrated in FIG. 22, in which the western blot of the cell lysates was probed with anti-phospho-tyrosine for activated FGFR-1(IIIc) receptor. The results show that the FR1-A1 by itself does not activated the receptor, but significantly inhibits ligand induced receptor phosphorylation.

Figure 23:
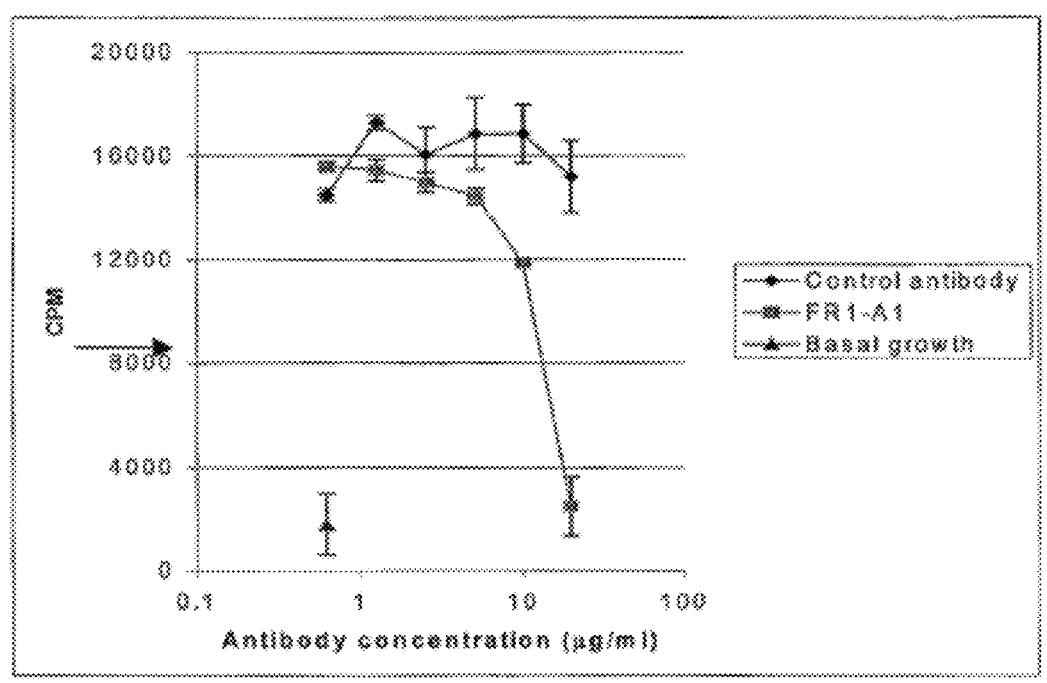
FIG. 23 shows mitogenesis of G18 cells in vitro in presence of antibodies. Each data point is an average of triplicates. Error bars are standard deviations.

Auto-phosphorylation of the FGFR-1 receptors frequently leads to the mitogenic response of the cells through mitogen activated protein kinase (MAPK) cascade in cytoplasma. Therefore, inhibition of receptor phosphorylation by FR1-A1 leads to inhibition of cell mitogenesis. Using flow cytometry analysis, it was found that G18 cells express FGFR-1 (IIIc) receptors on the cell surface. FIG. 23 shows that the addition of 20 ng/ml FGF-2 increased the level of DNA synthesis by approximately 5 folds compared to the control, and the antibody decreased this stimulation in a dose-dependant manner.

Example 16

Induction of Weight Loss (FR1-A1)

Figure 24:
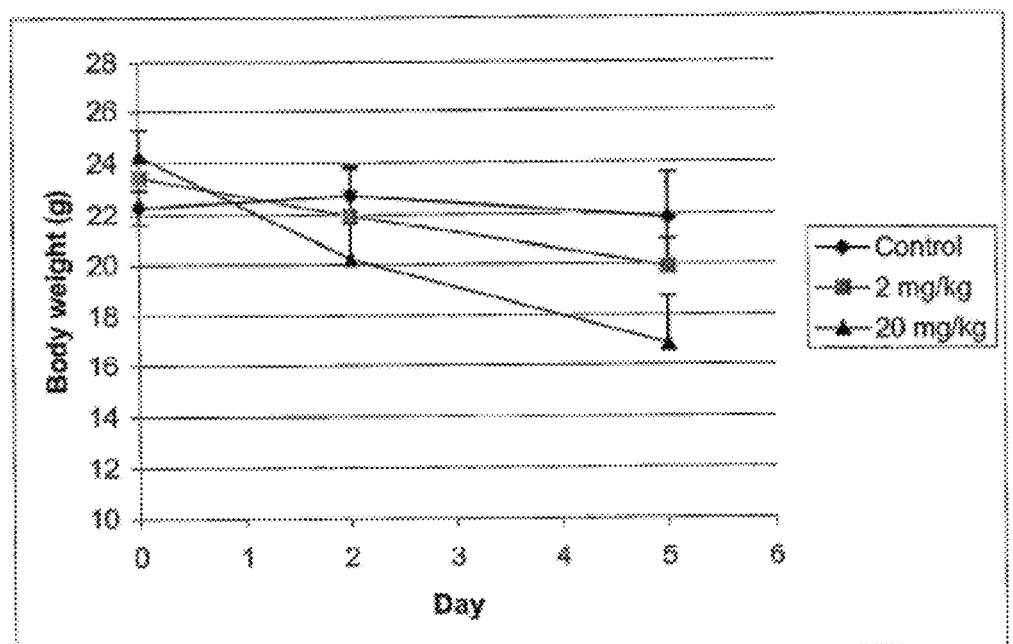
FIG. 24 shows the effect of FR1-A1 on body weights in nu/nu female mice (Mean+/−SEM).
Figure 25:
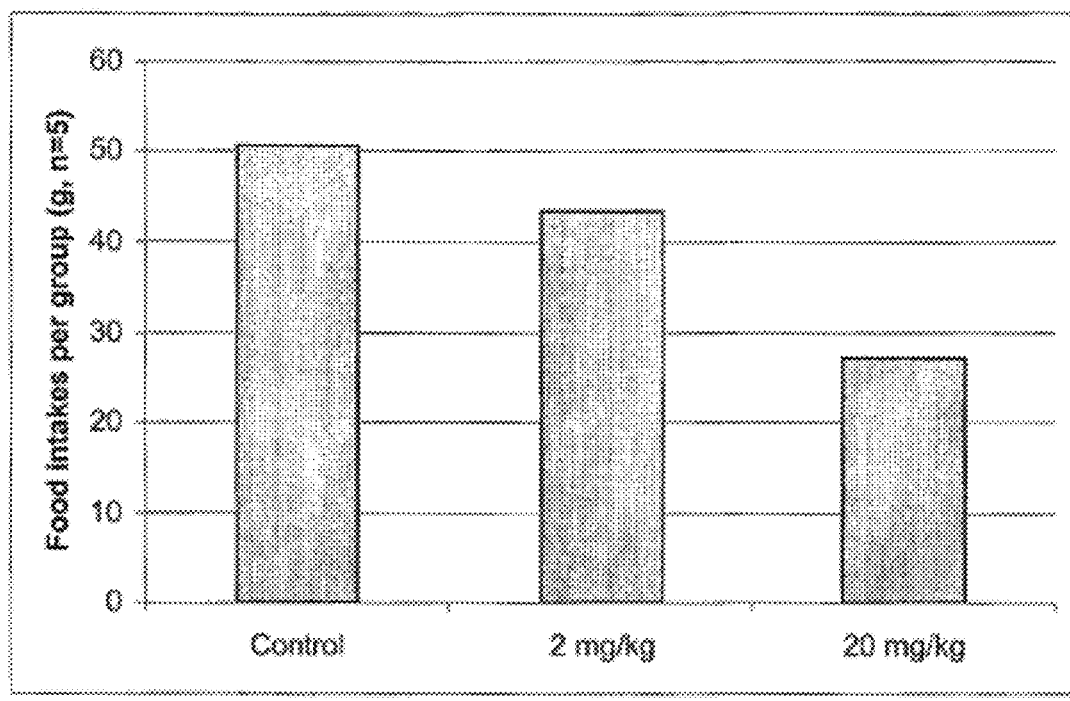
FIG. 25 shows the effect of FR1-A1 on food intakes in nu/nu female mice.
Figure 26A:
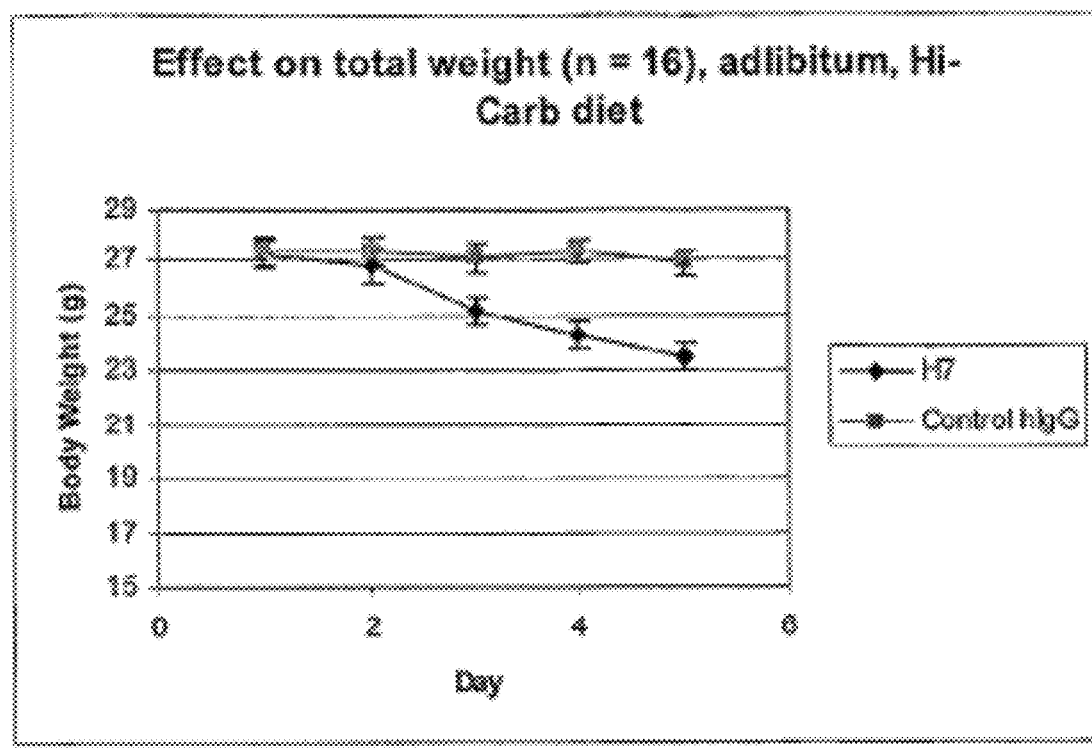
FIG. 26A shows decrease in daily body weight with FR1-H7 treatment as compared to control.
Figure 26B:
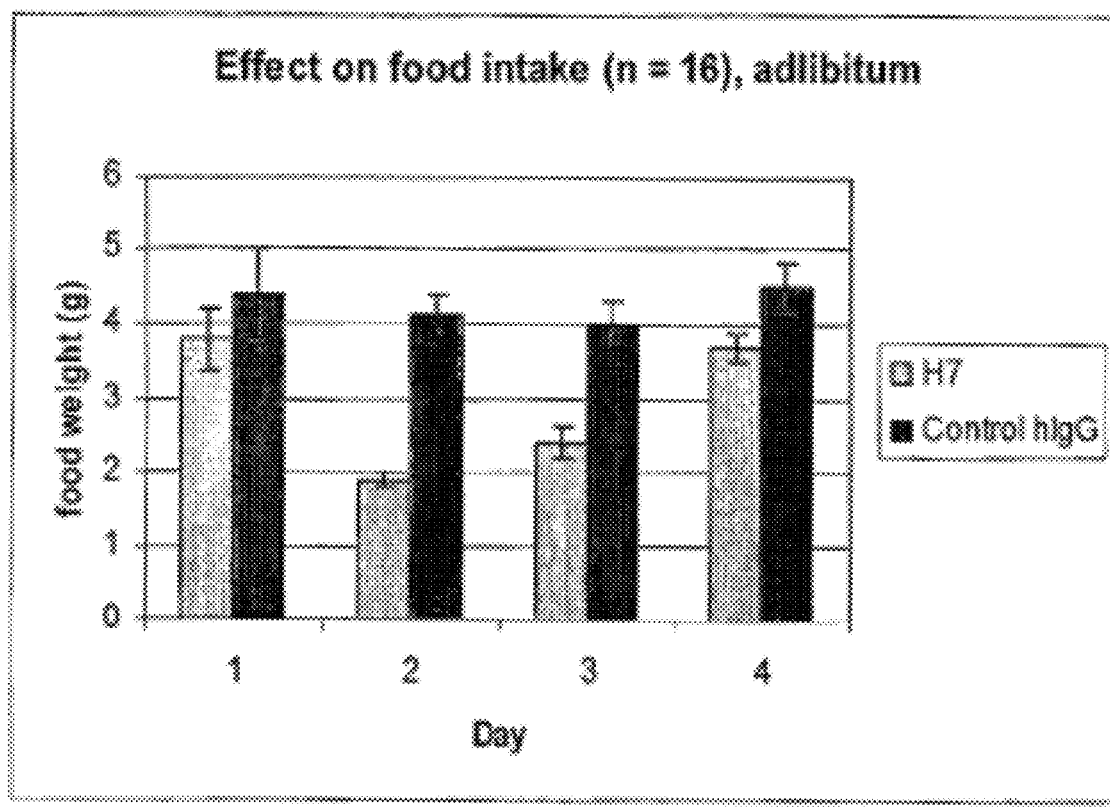
FIG. 26B shows decrease in daily food intake with FR1-H7 treatment as compared to control.
Figure 26C:
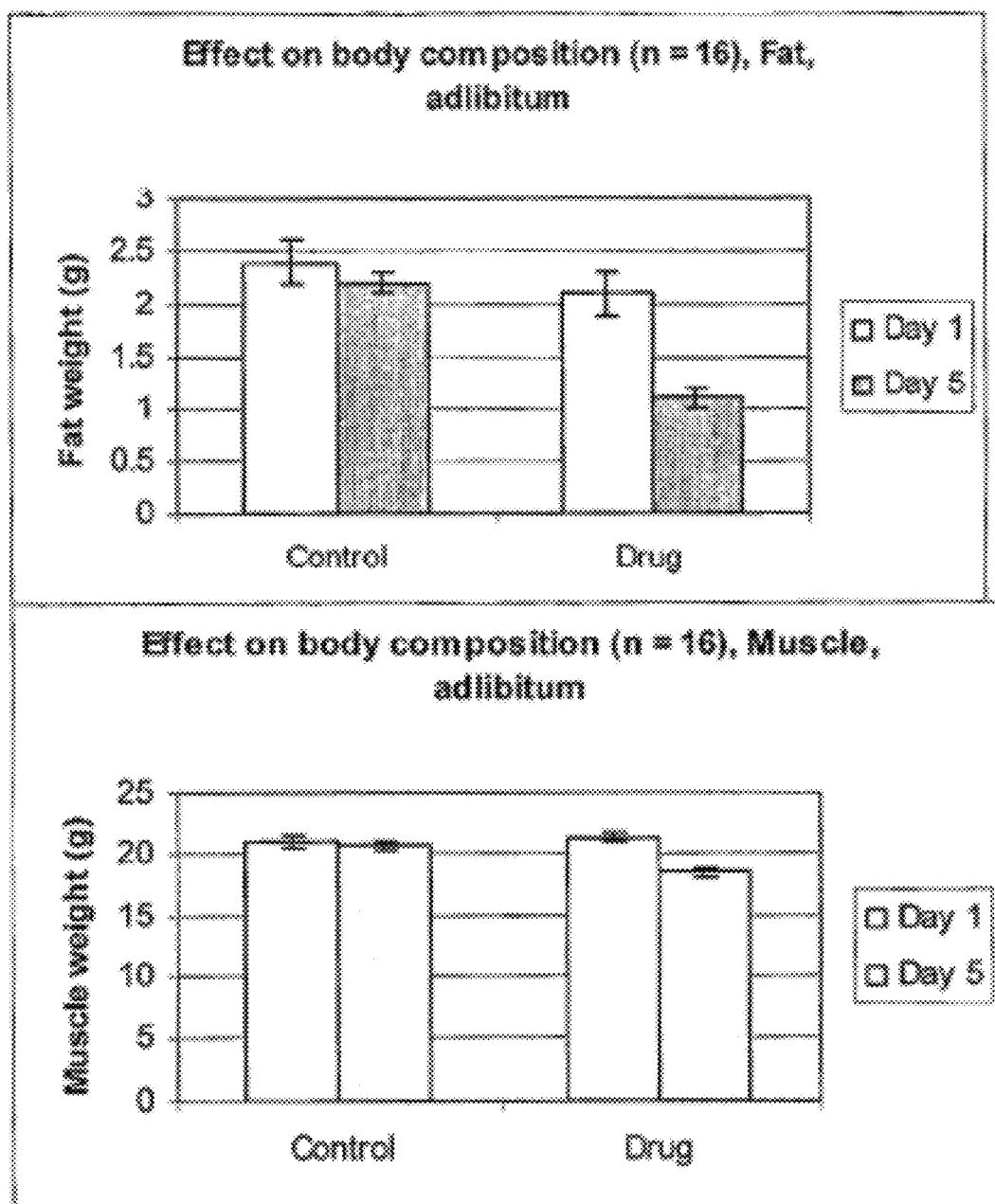
FIG. 26C shows decrease in fat and muscle weights with FR1-H7 treatment as compared to control.
Figure 26D:
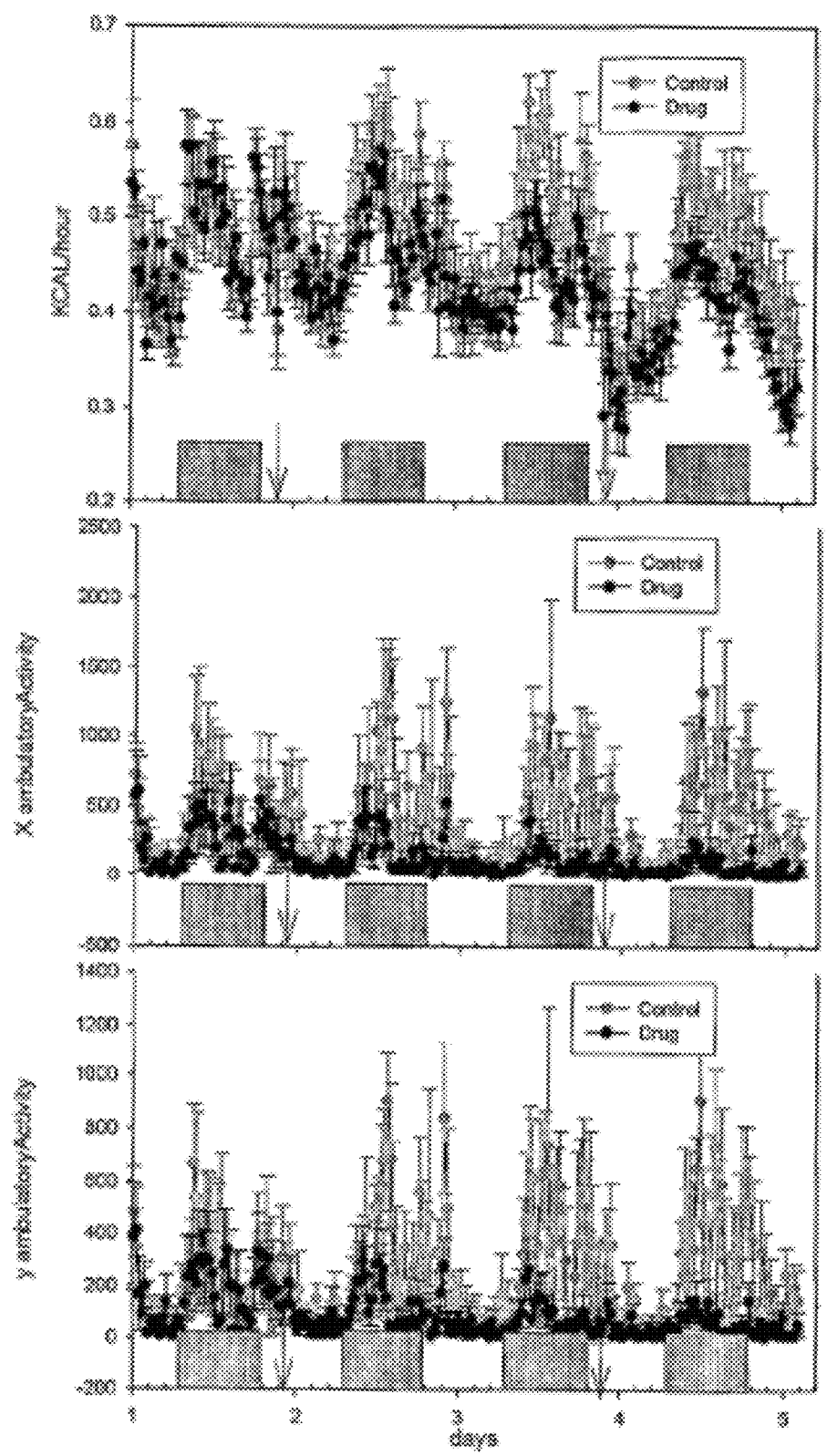
FIG. 26D shows decrease in energy expenditure and ambulatory activities with FR1-H7 treatment as compared to control.
Figure 26B:
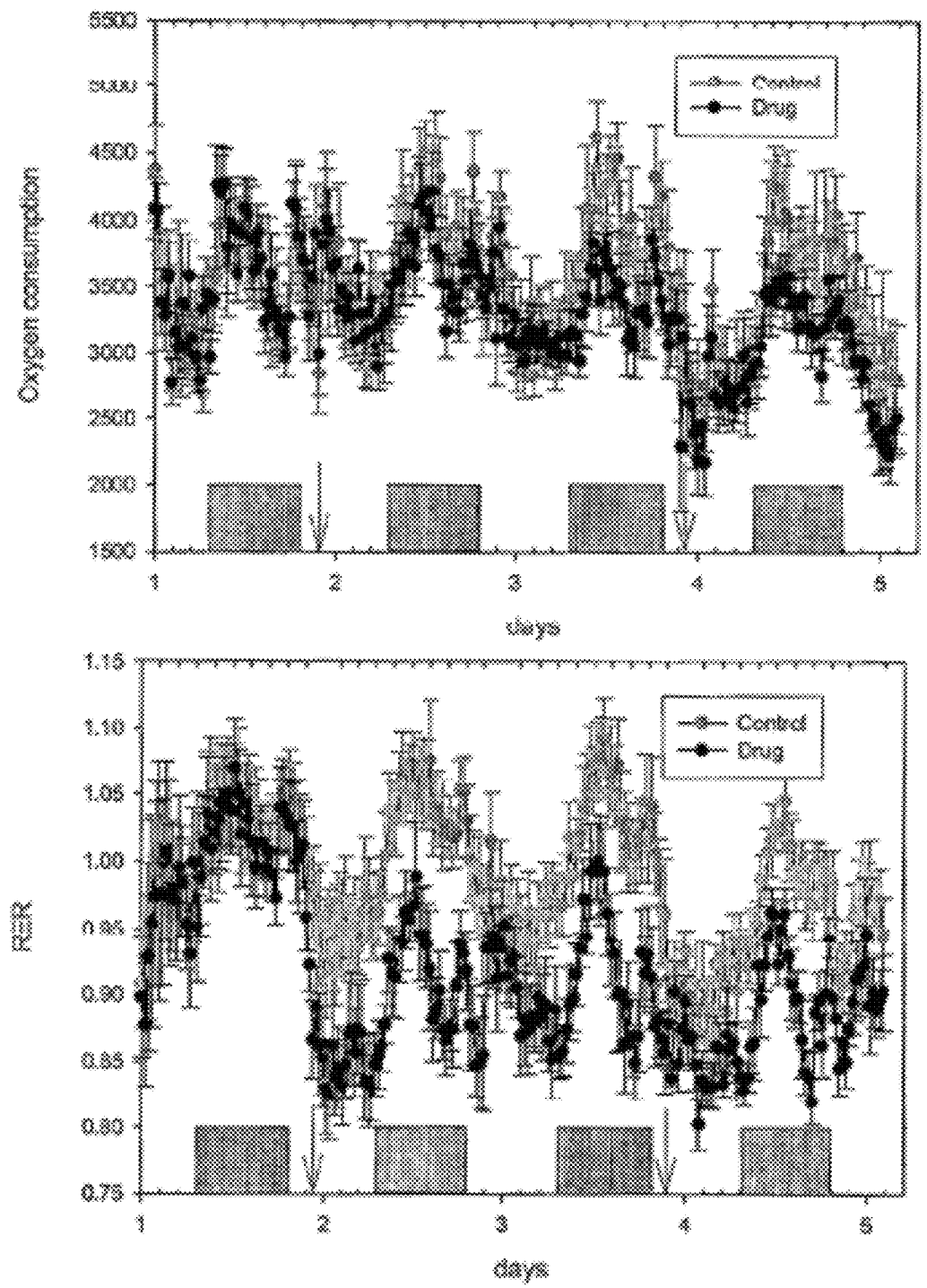

Similar to what was observed with FR1-H7 antibody, FR1-A1 caused rapid weight loss to female athymic nude mice. As shown in FIG. 24, on day 5, after two treatments, mice in 2 mg/kg dosage group lost an average of ~9% of the body weight compared to the control. Mice in 20 mg/kg group lost ~23%. Non-fast food intake, measured over the period between the first and second treatments, was reduced by ~14% and ~44% in 2 mg/kg and 20 mg/kg groups, respectively (FIG. 25).

Example 17

Isolation of Monoclonal Antibody (FR1-4H)

Figure 29:
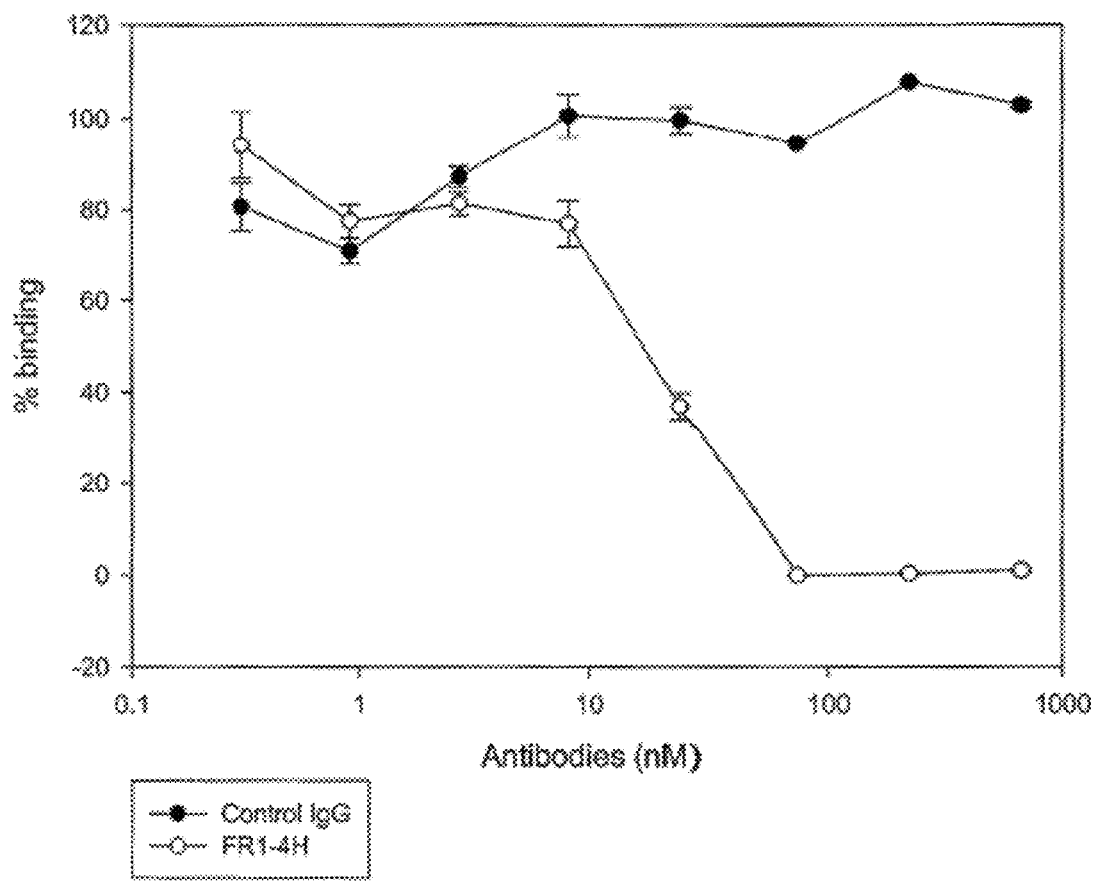
FIG. 29 shows that FR1-4H inhibited the binding of FGFR-1(IIIb) to FGF ligand. Percent binding was determined using the ELISA blocking assay. Each data point is an average of duplicates. Error bars are standard deviations.

In addition to FR1-A1 and FR1-H7, yet another FGFR-1 specific antibody FR1-4H (FIG. 28) was clones. Through BiaCore® analyses, the KDa of this antibody to FGFR-1 (IIIb) was determined to be 1.1 nM. In comparison, the KDa to FGFR-1(IIIc) was greater than 10 μM. Therefore, FR1-4H is considered to be specific to only the b-splicing form of FGFR-1. Like FR1-A1 and FR1-H7, FR1-4H is a neutralizing antibody, which blocks the receptor from binding to the ligand (FIG. 29). It was therefore deduced that FR1-4H would afford many similar effects displayed by the other two FGFR-1 antibodies as described previously.

FR1-A1 and FR1-H7 exhibited high affinity binding towards FGFR-1, and low affinity binding towards FGFR-4. Both antibodies could inhibit the ligand-induced activation of FGFR-1 potently. In animals, the two antibodies produced almost identical weight-loss phenomena, accompanied by significant food intake reduction. From the commonalities of these two antibodies it may be concluded that other FGFR antagonists are capable of inducing weight reduction through a FGFR-1 or FGFR-4 pathway related anorexic effect.

The procedures to isolate and clone FR1-4H is identical to those of FR1-A1 and FR1-H7 as described in Examples 2 and 12, except that phage candidates during the screening process were selected for specific binding to the FGFR-1(IIIb) instead of FGFR-1(IIIc).

Example 18

ELISA Blocking Assays for FR1-4H

This experiment was thoroughly described in Examples 6 and 14, except that FGFR-1(IIIb) recombinant protein was used instead of FGFR-1(IIIc) in all occasions. FR1-4H inhibited the binding of FGFR-(IIIb) to FGF Ligand (FIG. 29). Percent binding was determined using the ELISA blocking assay described in Examples 6 and 14. Percent binding was statistically reduced by treatment with FR1-4H over control above 1 nM.

Example 19

FGFR Small Molecule Inhibitors

Many small molecules inhibit FGFR kinase activity; a few examples are given in FIG. 30. The two pyrimido-pyridine derivatives were tested.

PolyE-Y peptide (Sigma, St. Louis, Mo.) was coated to a 96-well Immulon® 2B microtiter plates (ThermoLab Systems, Franklin, Mass.) by incubating 50 μl/well of the solution (5 μg/ml in PBS) for 12 hours at 4° C. The solution was then disposed, and the plate was washed twice with 200 μl washing buffer (PBS, 0.1% Tween-20). The following solutions were then mixed in each well: 25 μl Reaction buffer (100 mM Hepes, 10 mM $MgCl_2$, 10 mM $MnCl_2$ and 1 mM DTT, pH7.5), 2 μl compound solution (various concentrations in DMSO) and 20 μl FGFR kinase domain recombinant protein solution (100 ng/μl). After 5 mM incubation, 4.5 μl/well ATP solution (40 μM) was added and the reaction was allowed to proceed for 20 mM at 28° C. The reaction was stopped by washing the plate 3 times with the washing buffer. The plate was then blocked with 3% of BSA in PBS for 1 hr. Phosphorylation of polyE-Y peptides was detected using PY-20-HRP antibody (Santa Cruz Biotechnology, Santa Cruz, Calif.) as described by the manufacturer of the antibody. Raw data were processed using a custom-made arithmetic to generate an $IC_{50}$ value for each compound.

Both pyrimido-pyridines derivatives inhibited the kinase activities of all FGFRs in an enzymatic assay (Table 1). In cell-based assay, these two compounds were found to potently inhibit the ligand-induced phosphorylation of FGFR-1c receptor (FIG. 31). Because these compounds showed antagonistic activity toward FGFR-1, and to a lesser extend, FGFR-4, they should share the same weight-loss inducing properties in animals with FR1-A1 and FR1-H7 antibodies.

TABLE 1

FGFR small molecule inhibitors inhibited the kinase enzymatic activities in vitro. Values are IC50s determined using the enzymatic assay described in Methods.

|  | Pryimido-pyridines derivative A | Pryimido-pyridines derivative B |
| --- | --- | --- |
| FGFR-1 | 18 nM | 20 nM |
| FGFR-2 | 60 nM | N/A |
| FGFR-3 | 20 nM | 3 nM |
| FGFR-4 | 440 nM | 360 nM |

Example 20

Phosphorylation Assay for Small Molecule Inhibitors

The phosphorylation assay for small molecules is essentially the same as the phosphorylation assay described in Examples 7 and 15 and Phosphorylation Assay, except that small molecule compounds was used instead of FGFR-1 antibodies in all occasions. FGFR small molecule inhibitors inhibited the auto-phosphorylation of FGFR-1(IIIc) in a cell-based phosphorylation assay (FIG. 31). Equal amount of cell lysates were applied to each sample lane. Receptor auto-phosphorylation was probed using anti-phospho-tyrosine antibody as described in the original patent.

---

What is claimed is:

1. An antibody, or Fv (fragment variable) thereof, comprising a heavy chain variable region ($V_H$) and a light chain variable region ($V_L$), wherein the $V_H$ comprises complementarity determining regions (CDRs) $V_H$ CDR1, $V_H$ CDR2, and $V_H$ CDR3 and wherein the $V_L$ comprises CDRs $V_L$ CDR1, $V_L$ CDR2, and $V_L$ CDR3, wherein $V_H$ CDR1 is SEQ ID NO:1, $V_H$ CDR2 is SEQ ID NO: 2, $V_H$ CDR3 is SEQ ID NO: 3, $V_L$ CDR1 is SEQ ID NO: 4, $V_L$ CDR2 is SEQ ID NO: 5, and $V_L$ CDR3 is SEQ ID NO: 6, wherein the antibody or Fv thereof binds to FGFR1(IIIc).

2. The antibody of claim 1 comprising two heavy chain variable regions ($V_H$) and two light chain variable regions ($V_L$), wherein each $V_H$ comprises complementarity determining regions (CDRs) $V_H$ CDR1, $V_H$ CDR2, and $V_H$ CDR3 and wherein each $V_L$ comprises CDRs $V_L$ CDR1, $V_L$ CDR2, and $V_L$ CDR3, wherein $V_H$ CDR1 is SEQ ID NO:1, $V_H$ CDR2 is SEQ ID NO: 2, $V_H$ CDR3 is SEQ ID NO: 3, $V_L$ CDR1 is SEQ ID NO: 4, $V_L$ CDR2 is SEQ ID NO: 5, and $V_L$ CDR3 is SEQ ID NO: 6.

3. The antibody or Fv of claim 1 comprising a heavy chain variable region (HCVR) and a light chain variable region (LCVR), wherein the HCVR comprises the amino acid sequence of SEQ ID NO: 7 and the LCVR comprises the amino acid sequence of SEQ ID NO: 8.

4. A pharmaceutical composition comprising the antibody or Fv (fragment variable) thereof of claim 1 and a pharmaceutically acceptable carrier.

5. A method of treating obesity in a mammal comprising administering the antibody or Fv of claim 1 to the mammal, wherein food intake is reduced to treat obesity.

6. A method of reducing food intake in a mammal comprising administering the antibody or Fv of claim 1 to the mammal.

* * * * *